(12) United States Patent
Burgon et al.

(10) Patent No.: US 8,143,377 B2
(45) Date of Patent: Mar. 27, 2012

(54) MUSCLE LAMIN A/C INTERACTING PROTEIN, GENE ENCODING SAME, AND USES THEREFOR

(75) Inventors: Patrick G. Burgon, Ottawa (CA); Elmira Ahmady, Ottawa (CA)

(73) Assignee: Ottawa Heart Institute Research Corporation, Ottawa, Ontario (CA)

( * ) Notice: Subject to any disclaimer, the term of this patent is extended or adjusted under 35 U.S.C. 154(b) by 773 days.

(21) Appl. No.: 12/193,366

(22) Filed: Aug. 18, 2008

(65) Prior Publication Data

US 2009/0100534 A1  Apr. 16, 2009

Related U.S. Application Data

(60) Provisional application No. 60/956,533, filed on Aug. 17, 2007.

(51) Int. Cl.
*C07K 5/00* (2006.01)
*C07K 1/00* (2006.01)
(52) U.S. Cl. .................................... 530/350; 530/395
(58) Field of Classification Search ................... None
See application file for complete search history.

(56) References Cited

OTHER PUBLICATIONS

Somech R. et al., Nuclear Envelopathies—Raising the Nuclear Veil, Apr. 2005, 8R-15R, 57 (5 Pt2), E Pub.
Ostlund C. et al., Intracellular Trafficking of Emerin, The Emery-Dreifuss Muscular Dystrophy Protein, Journal of Cell Science, 1999, pp. 1709-1719, vol. 112 Issue 11, Company of Biologists, New York.
Charniot J.C. et al., Functional Consequences of an LMNA Mutation Associated with a New Cardiac and Non-Cardiac phenotype, Human Mutation, 2003, pp. 473-481, vol. 21 Issue 5, Wiley-Liss Inc.
Muchir A. et al., Identification of Mutations in the Gene Encoding Lamins A/C in Autosomal Dominant Limb Girdle Muscular Dystrophy with Atrioventricular Conduction Disturbances (LGMD1B), Hum Mol Genet, 2000, pp. 1453-1459, vol. 9 Issue 9, Oxford University Press.
Taylor M.R. et al., Natural History of Dilated Cardiomyopathy due to lamin A/C Gene Mutations, Journal of the American College of Cardiology, Mar. 2003, pp. 771-780, vol. 41 Issue 5, Elsevier Science Inc.
Bonne G. et al., Clinical and Molecular Genetic Spectrum of Autosomal Dominant Emery-Dreifuss Muscular Dystrophy due to Mutations of the Lamin A/C Gene, Annals of Neurology, 2000, pp. 170-180, vol. 48 Issue 2, American Neurological Association.
Brodsky G.L. et al., Lamin A/C Gene Mutation Associated with Dilated Cardiomyopathy with Variable Skeletal Muscle Involvement, Circulation, 2000, pp. 473-476, vol. 101 Issue 5, American Heart Association Inc.
Hegele R., LMNA Mutation Position Predicts Organ System Involvement in Laminopathies, Clinical Genetics, Jul. 2005, pp. 31-34, vol. 68 Issue 1, Blackwell Publishing Ltd.
Arimura T. et al., Mouse Model Carrying H222P-LMNA Mutation Develops Muscular Dystrophy and Dilated Cardiomyopathy Similar to Human Striated Muscular Laminopathies, Human Molecular Genetics, Janaury 2005, pp. 155-169 vol. 14 Issue 1, Oxford University Press.
Kitaguchi T. et al., A Missense Mutation in the Exon 8 of Lamin A/C gene in a Japanese Case of Autosomal Dominant Limb-Girdle Muscular Dystrophy and Cardiac Conduction Block, Neuromuscular Disorders, Sep. 2001, pp. 542-546, vol. 11 Issues 6-7, Elsevier Science B.V.
Hong J.S. et al., Cardiac Dysrhythmias, Cardiomyopathy and Muscular Dystrophy in Patients with Emery-Dreifuss Muscular Dystrophyand Limb-Gridle Muscular Dystrophy Type 1B, J Korean Med. Sci, 2005, pp. 283-290, vol. 20 Issue 2.
Van Der Kooi A.J. et al., A Newly Recognized Autosomal Dominant Limb Girdle Muscular Dystrophy With Cardiac Involvement, Annals of Neurology, 1996, pp. 636-642, vol. 39 Issue 5, Willey-Liss.
Arbustini E. et al., Autosomal Dominant Dilated Cardiomyopathy with Atrioventricular Block: A Lamin A/C Defect Related Disease, Journal of the American College of Cardiology, Mar. 2002, pp. 981-990, vol. 39 Issue 6, Elsevier Science Inc.
Brown C.A. et al., Novel and Recurrent Mutations in Lamin A/C in Patients with Emery-Dreifuss Muscular Dystrophy, American Journal of Medical Genetics Part A, 2001, pp. 359-367, vol. 102 Issue 4, Wiley-Liss, Inc.
Fatkin D. et al., Missense Mutations in the Rod Domain of the Lamin A/C Gene as Causes of Dilated Cardiomyopathy and Conduction-system Disease, New England Journal of Medicine, 1999, pp. 1715-1724, vol. 341 Issue 23, Massachusetts Medical Society.
Otomo J. et al., Electrophysiological and Histopathological Characteristics of Progressive Atrioventricular Block Accompanied by Familial Dilated Cardiomyopathy Caused by a Novel Mutation of Lamin A/C Gene, Journal of Cardiovascular Electrophysiology, 2005, pp. 137-145, vol. 16 Issue 2, Wiley Periodicals Inc.
Pethig K. et al., LMNA Mutations in Cardiac Transplant Recipients, International Journal of Cardiovascular Medicine, 2005, pp. 57-62, vol. 103 Issue 2, S. Karger AG, Basel.
Sebillion P. et al. Expanding the Phenotype of LMNA Mutations in Dilated Cardiomyopathy and Functional Consequences of these Mutations, Journal of Medical Genetics, 2003, pp. 560-567, vol. 40 Issue 8, BMJ Publishing Group.
Emery A.E., Emery-Dreifuss Syndrome, Journal of Medical Genetics, 1989, pp. 637-641, vol. 26 Issue 10, BMJ Publishing Group Ltd.
Jakobs P.M. et al., Novel Lamin A/C Mutations in two Families with Dilated Cardiomyopathy and Conduction System Disease, Journal of Cardiac Failure, 2001, vol. 7 Issue 3, Churchill Livingstone.
Funakoshi M. et al., Emerin and Cardiomyopathy in Emery-Dreifuss Muscular Dystrophy, Neuromuscular Disorders, 1999, pp. 108-114, vol. 9 Issue 2, Elsevier Science B.V.
Sullivan T. et al., Loss of A-Type Lamin Expression Comprises Nuclear Envelope Integrity Leading to Muscular Dystrophy, The Journal of Cell Biology, 1999, pp. 913-920, vol. 147 Issue 5, The Rockefeller University Press.
Cockell M. et al., Nuclear Compartments and Gene Regulation, Current Opinion in Genetics & Development, 1999, pp. 199-205, vol. 9 Issue 2, Elsevier Ltd.

(Continued)

*Primary Examiner* — Suzanne M Noakes
*Assistant Examiner* — Jae W Lee
(74) *Attorney, Agent, or Firm* — Kathleen E. Marsman; Borden Ladner Gervais LLP

(57) ABSTRACT

Peptide sequences of human and murine muscle lamin A/C interacting protein and nucleotide sequences encoding same and are provided. Uses of the muscle lamin A/C interacting protein are also provided herein.

1 Claim, 60 Drawing Sheets

OTHER PUBLICATIONS

Gianakopoulos P.J. et al., Hedgehog Signaling Induces Cardiomyogenesis in P19 Cells, J. Biol. Chem., 2005, vol. 280 Issue 22, American Society for Biochemistry and Molecular Biology.

Pandolfi P.P. et al., Targeted Disruption of the GATA3 Gene Causes Severe Abnormalities in the Nervous System and in Fetal Liver Haematopoisis, Nat Genet, 1995, pp. 40-44, vol. 11 Issue 1.

Ausubel F. et al., Current Protocols in Molecular Biology, 2004, John Wiley & Sons Inc., New York.

Sibony M. et al., Enhancement of mRNA in Situ Hybridization Signal by Microwave Heating, Lab Invest, 1995, pp. 586-591, vol. 73 Issue 4.

Fatkin D. et al., An Abnormal Ca(2+) Response in Mutant Sarcomere Protein-Mediated Familial Hypertrophic Cardiomyopathy, J Clin Invest, 2000, pp. 1351-1359, vol. 106 Issue 11, American Society for Clinical Investigation.

Mounkes L.C. et al., Expression of an LMNA-N195K Variant of A-Type Lamins Results in Cardiac Conduction Defects and Death in Mice, Human Molecular Genetics, 2005, pp. 2167-2180, vol. 14 Issue 15, Oxford University Press.

Seidman J.G. et al., The Genetic Basis for Cardiomyopathy: From Mutation Identification to Mechanistic Paradigms, Cell, 2001, pp. 557-567, vol. 104 Issue 4, Cell Press.

Flashman E. et al., Cardiac Myosin Binding Protein C: Its Role in Physiology and Disease, Circ Res, 2004, pp. 1279-1289, vol. 94 Issue 10, American Heart Association, Inc.

Fougerousse F. et al., Cardiac Myosin Binding Protein C Gene is Specifically Expressed in Heart During Murine and Human Development, Circ Res, 1998, pp. 130-133, vol. 82 Issue 1, American Heart Association, Inc.

Gautel M. et al., Isoform Transitions of the Myosin Binding Protein C Family in Developing Human and Mouse Muscles: Lack of Isoform Transcomplementation in Cardiac Muscles, Circ Res, 1998, pp. 124-129, vol. 82 Issue 1, American Heart Association, Inc.

Alyonycheva T.N. et al., Isoform-Specific Interaction of the Myosin-Binding Proteins (MyBPs) with Skeletal and Cardiac myosin is a property of the C-Terminal Immunoglobulin Domain, J Biol Chem, 1997, pp. 20866-20872, vol. 272 Issue 33, The American Society for Biochemistry and Molecular Biology, Inc.

Freiburg A. et al., A Molecular Map of the Interactions Between Titin and Myosin-Binding Protein C. Implications for Sarcomeric Assembly in Familial Hypertrophic Cardiomyopathy, Eur J Biochem, 1996, pp. 20866-20872, vol. 272 Issue 33, The American Society for Biochemistry and Molecular Biology, Inc.

Kulikovskaya I. et al., Effect of MyBP-C Binding to Actin on Contractility in Heart Muscle, J Gen Physiol, 2003, pp. 761-774, vol. 122 Issue 6, Rockefeller University Press.

Watkins H., Genetic Clues to Disease Pathways in Hypertrophic and Dilated Cardiomyopathies, Circulation, 2003, pp. 1344-1346, vol. 107 Issue 10, American Heart Association, Inc.

Bonne G. et al., Familial Hypertrophic Cardiomyopathy: From Mutations to Functional Defects, Circ Res, 1998, pp. 580-593, vol. 83 Issue 6, American Heart Association, Inc.

Carrier L. et al., Asymmetric Septal Hypertrophy in Heterozygous Myosin-Binding Protein-C Mutant Mice, Journal of Clinical Investigation, 1999, pp. 1235-1244, vol. 104 Issue 9, American Society for Clinical Investigation.

Harris S.P. et al., Hypertrophic Cardiomyopathy in Cardiac Myosin Binding Protein-C Knockout Mice, Circulation Research, 2002, pp. 594-601, vol. 90 Issue 5, American Heart Association, Inc.

McOnnell B.K. et al., Dilated Cardiomyopathy in Homozygous Myosin-Binding Protein-C Mutant Mice, Journal of Clinical Investigation, 1999, pp. 1235-1244, vol. 104 Issue 9, American Society for Clinical Investigation.

a
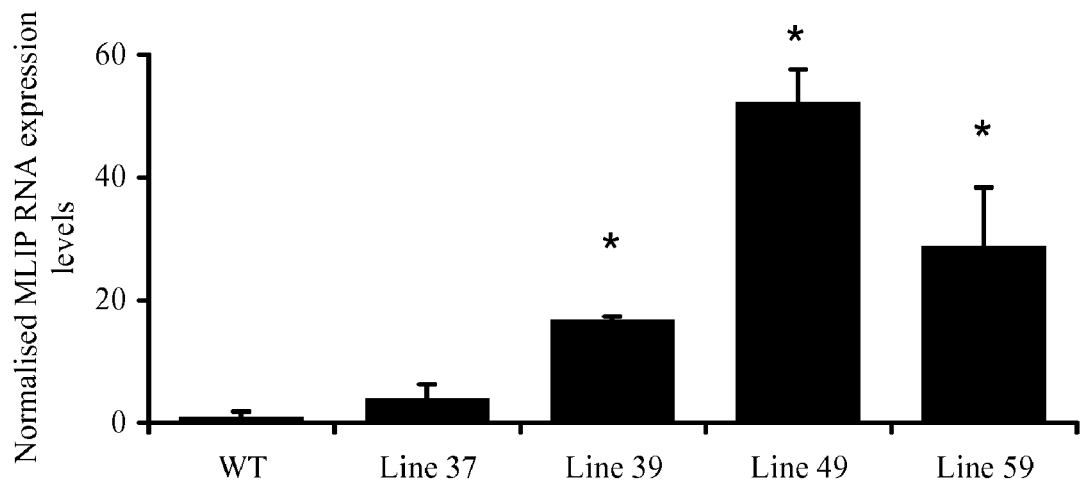
b
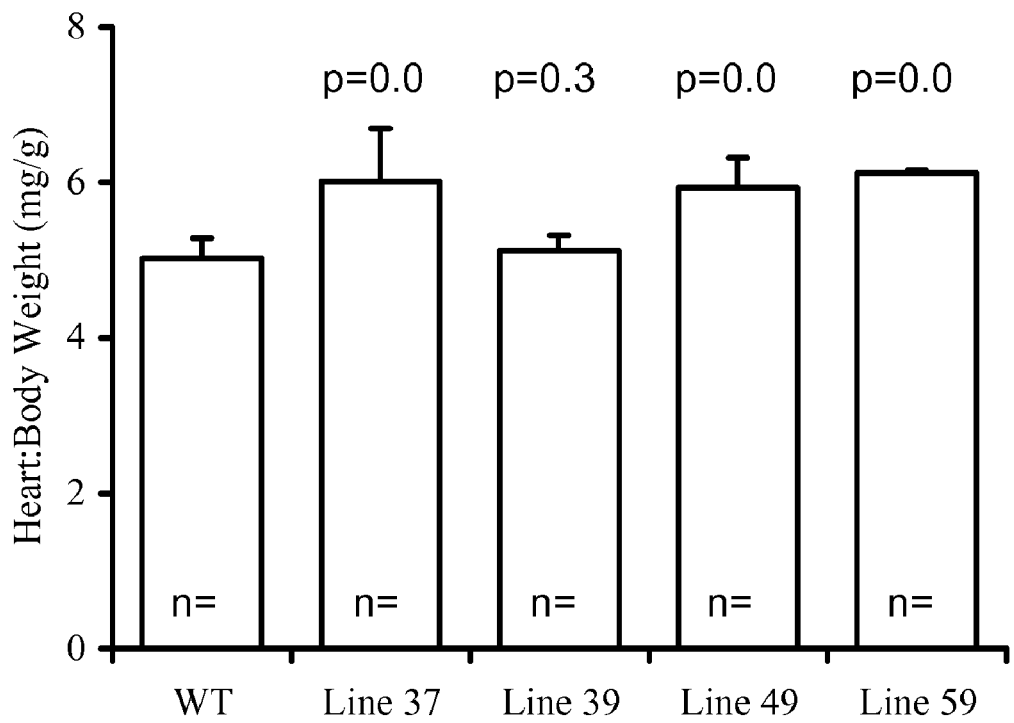
Figures 1a-b a) αMHC-MLIP-line39
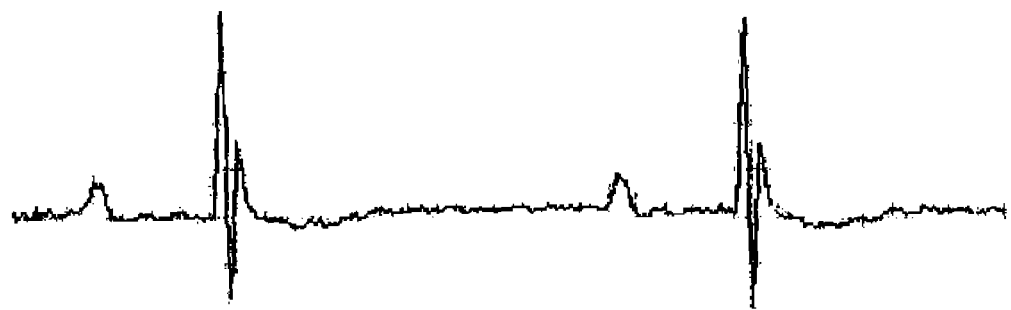
b) αMHC-MLIP-line49
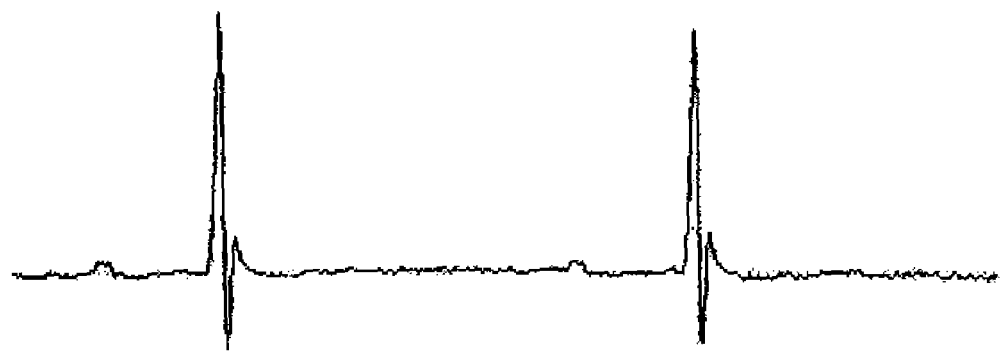
c) Control
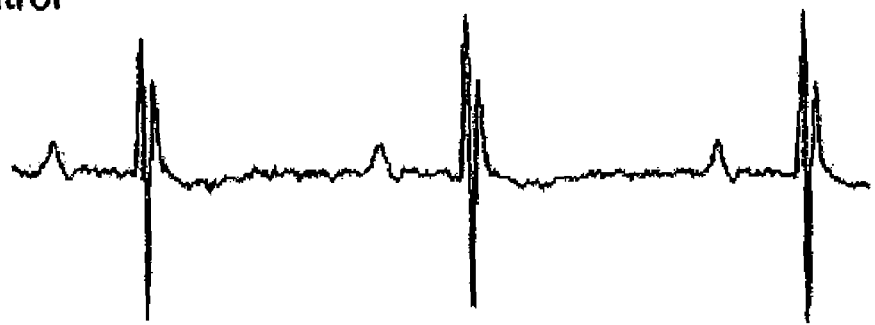
Figures 2a-c

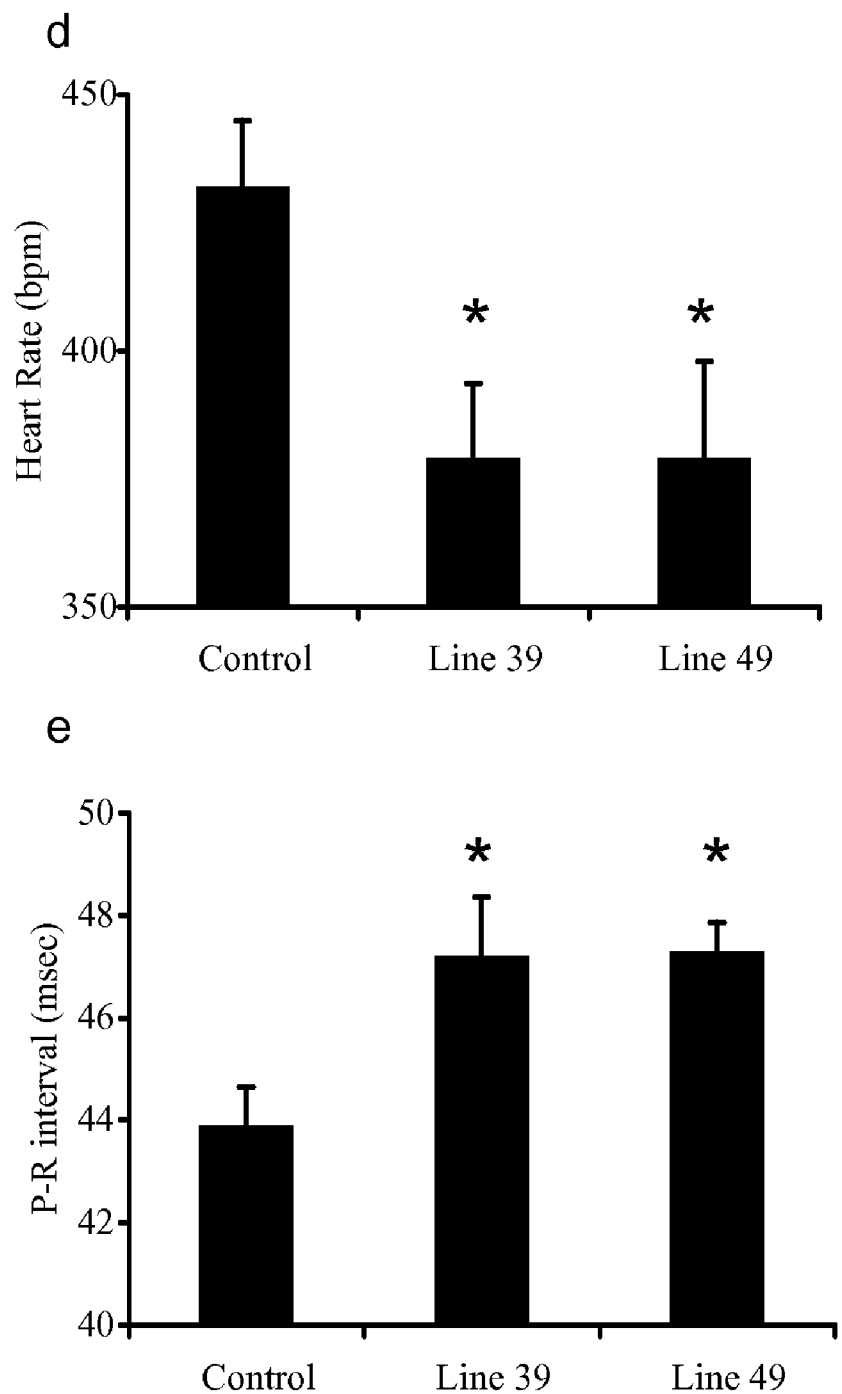
Figures 2d-e

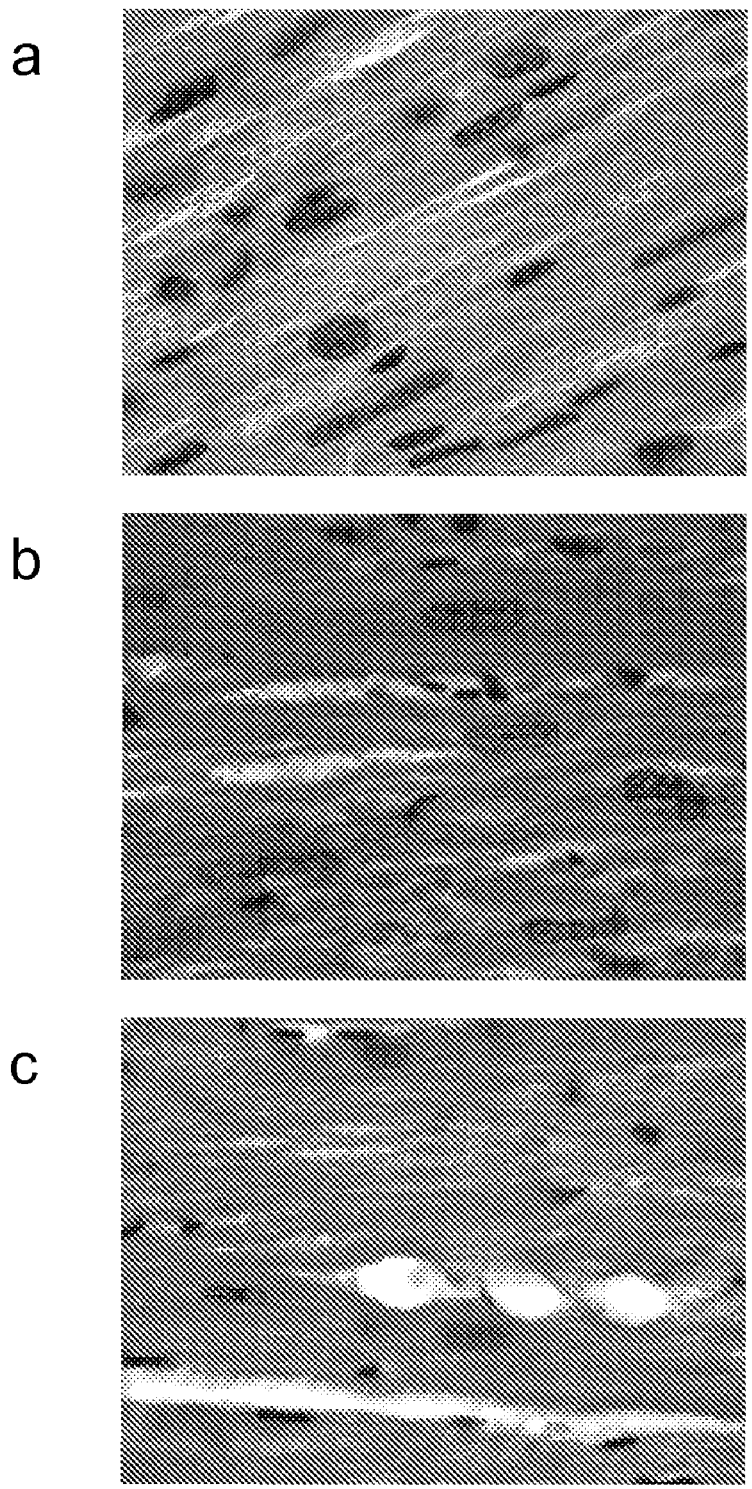
Figures 3a-c

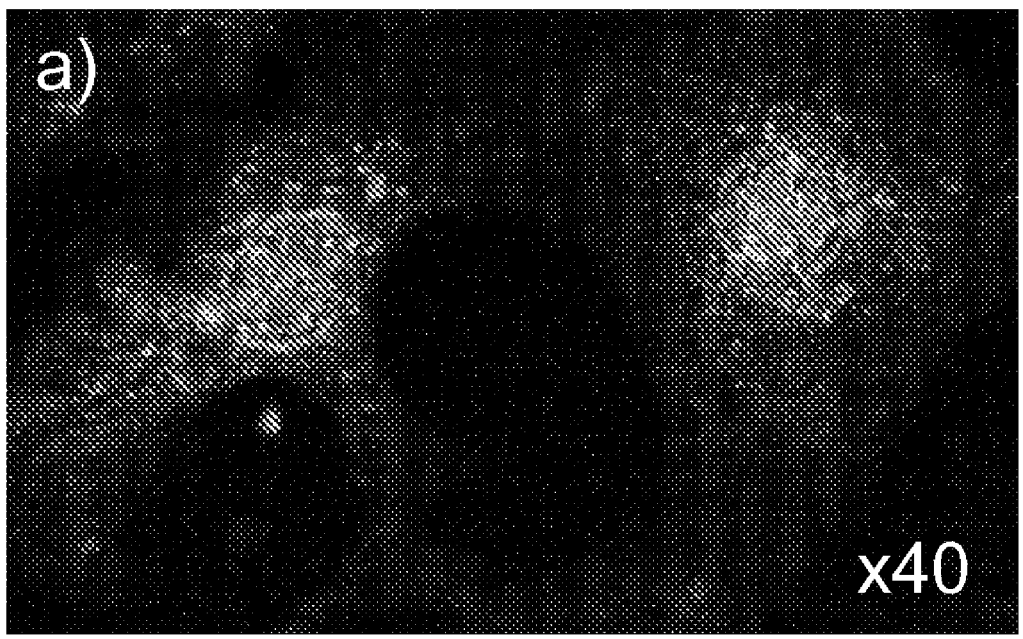
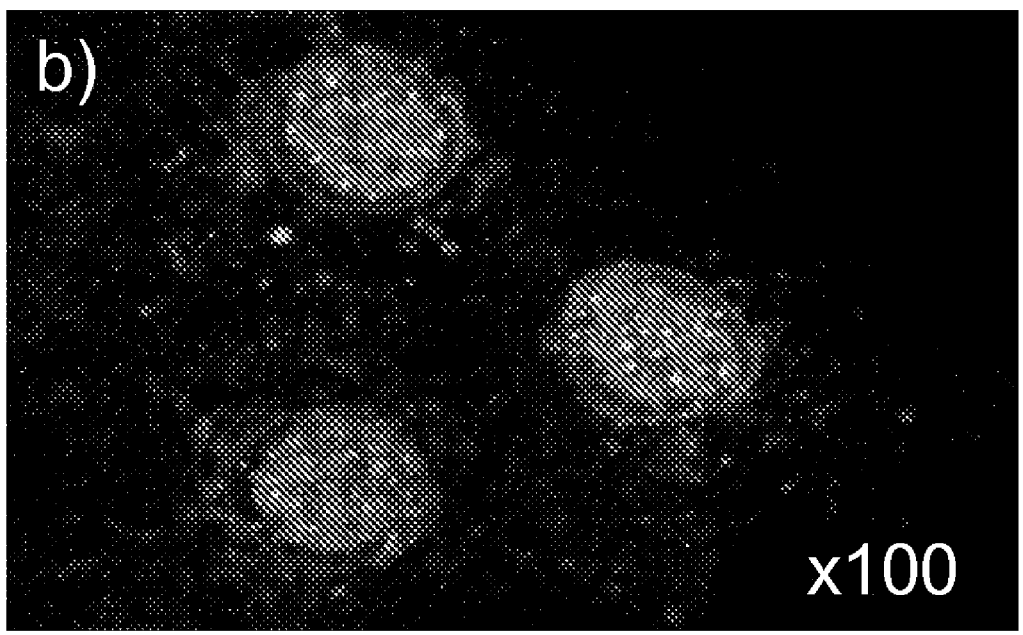
Figures 4a-b

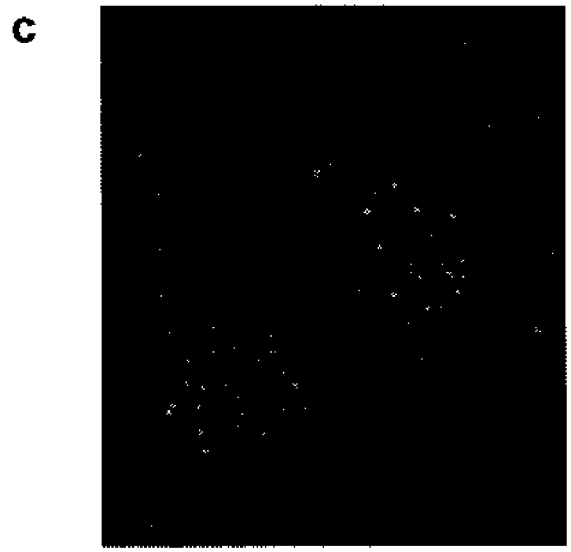
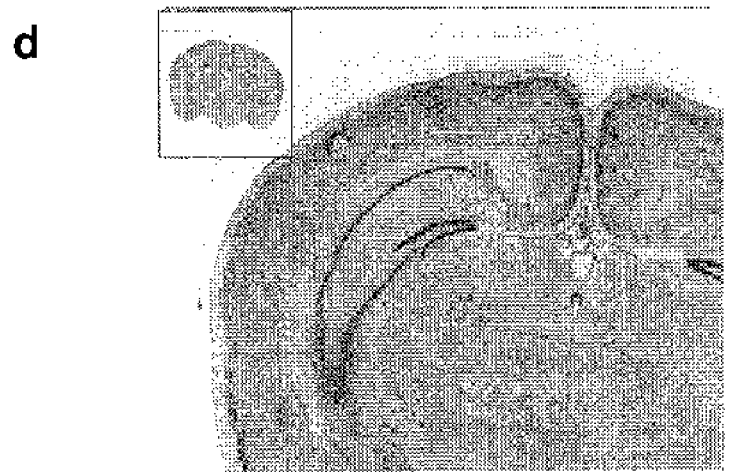
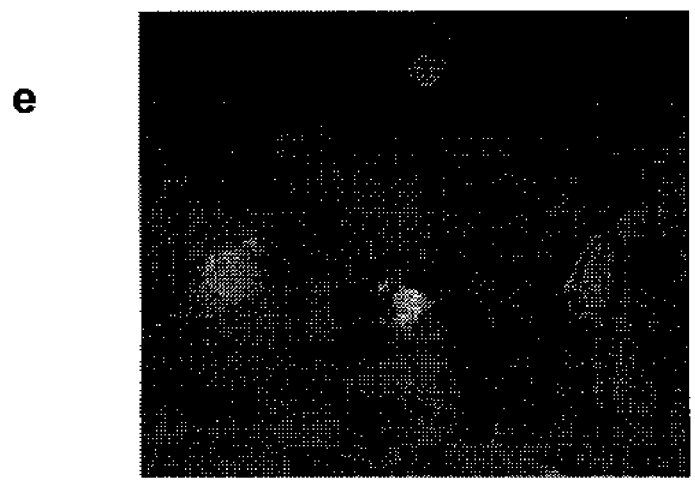
Figures 4c-e a
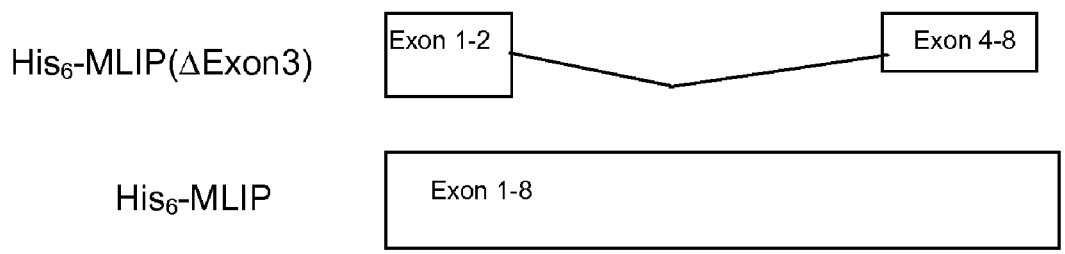
b
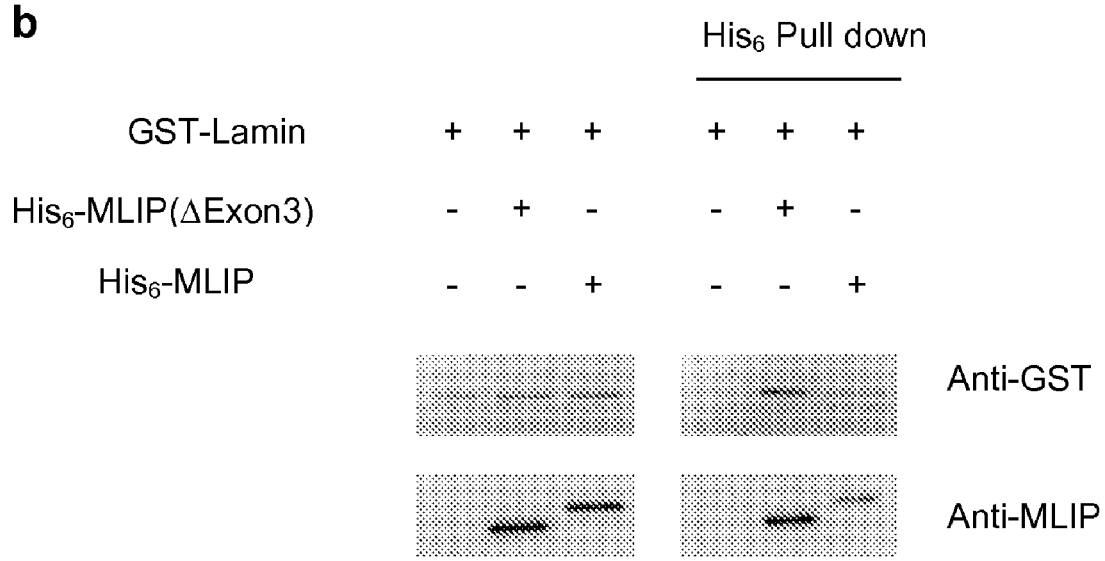
Figures 5a-b

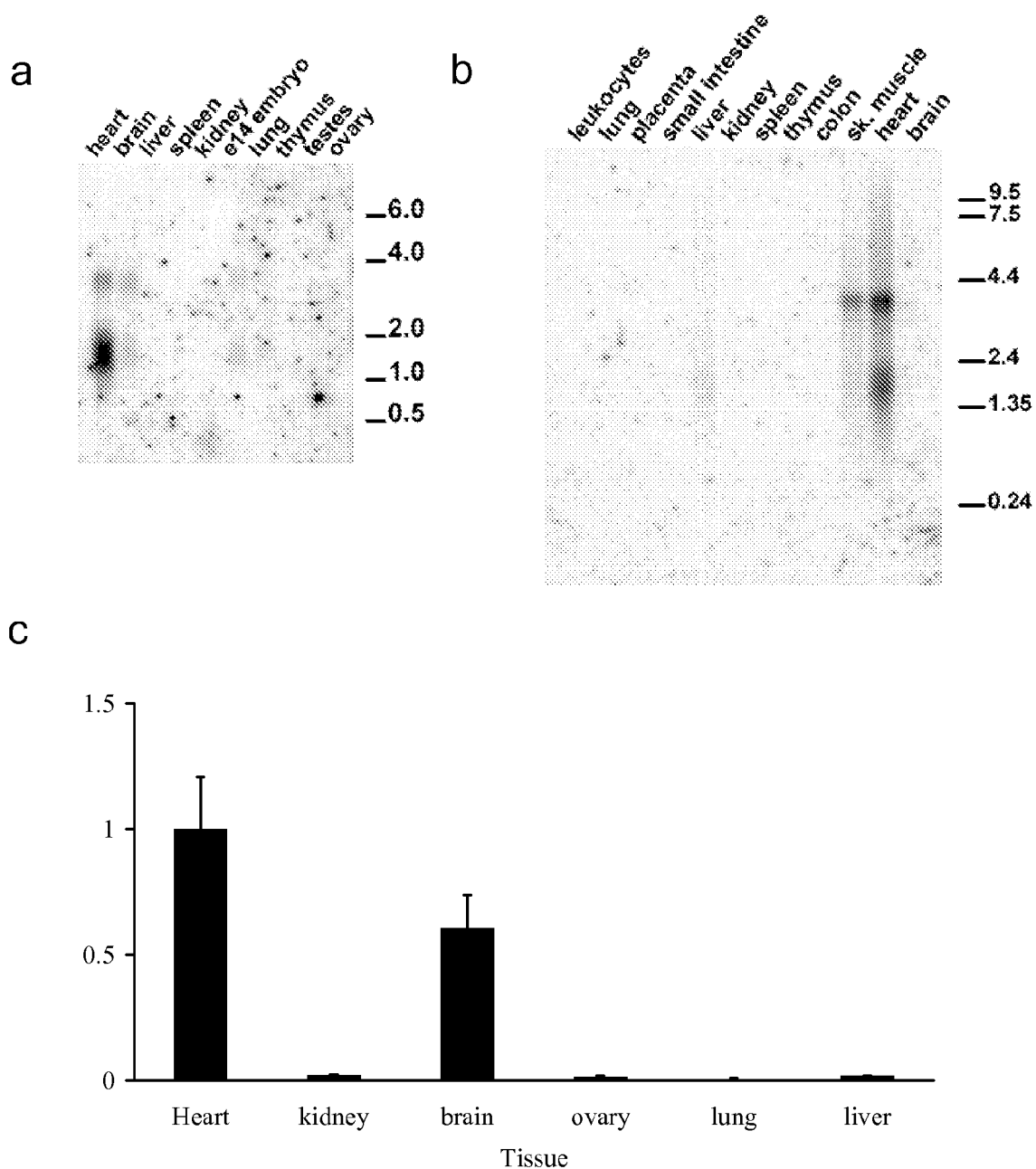
Figures 6a-c a
Day: 0 1 2 3 4 5 6 7 8 9
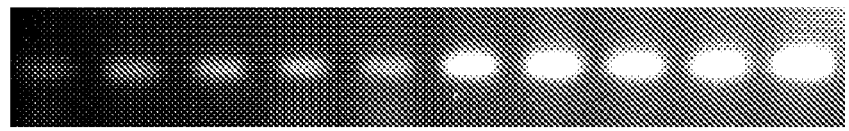
MLIP
GAPDH
b
Day: 0 3 5 9
Figures 7a-b a
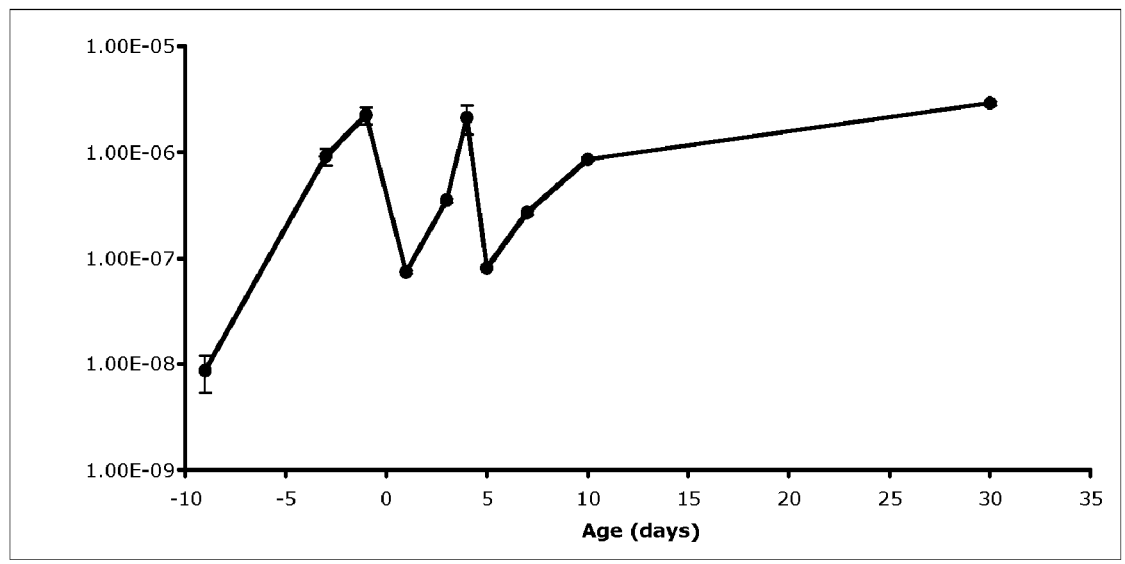
b
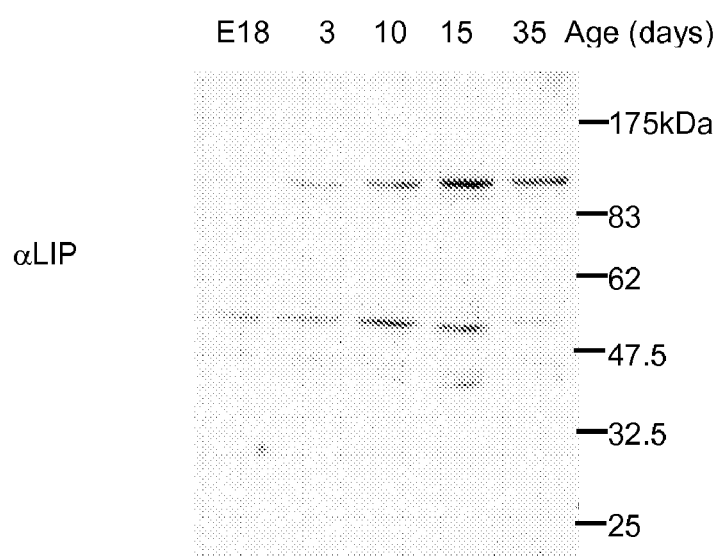
Figure 8

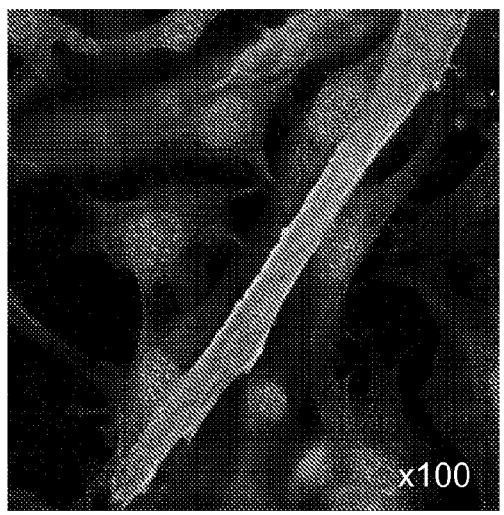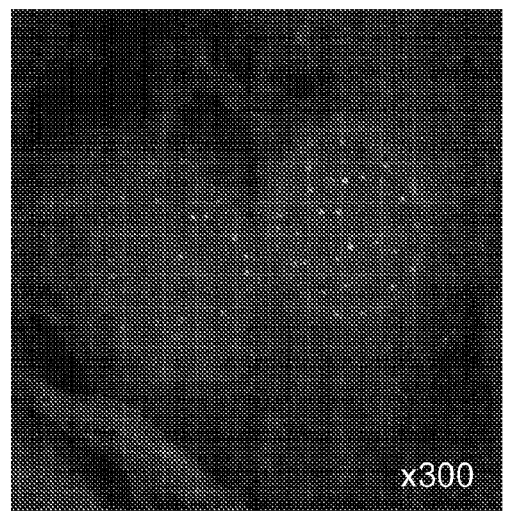
Green = MLIP
Red = MyHC
Blue = Nucleus
Figure 12

MLIP = Green

PML = Red

a
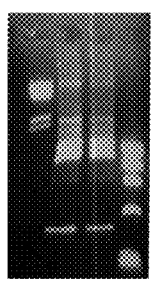  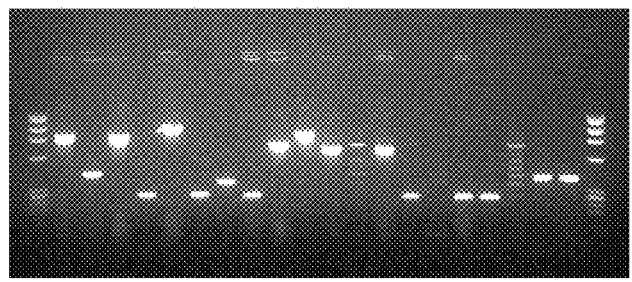
b
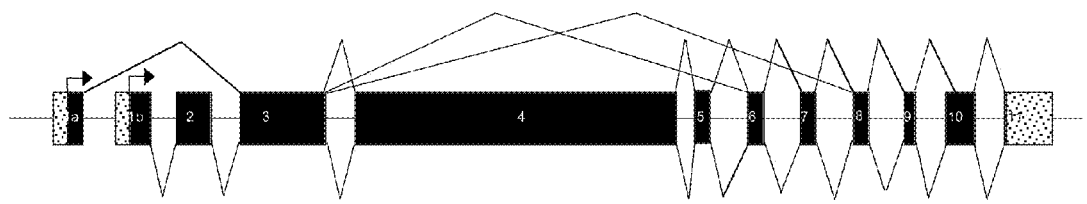
Figure 18

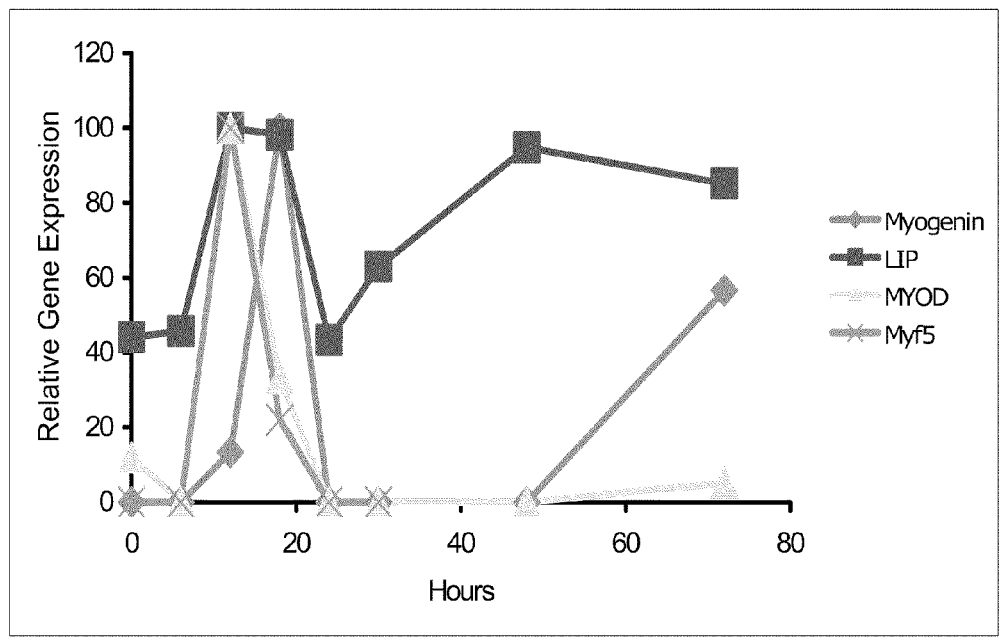
a
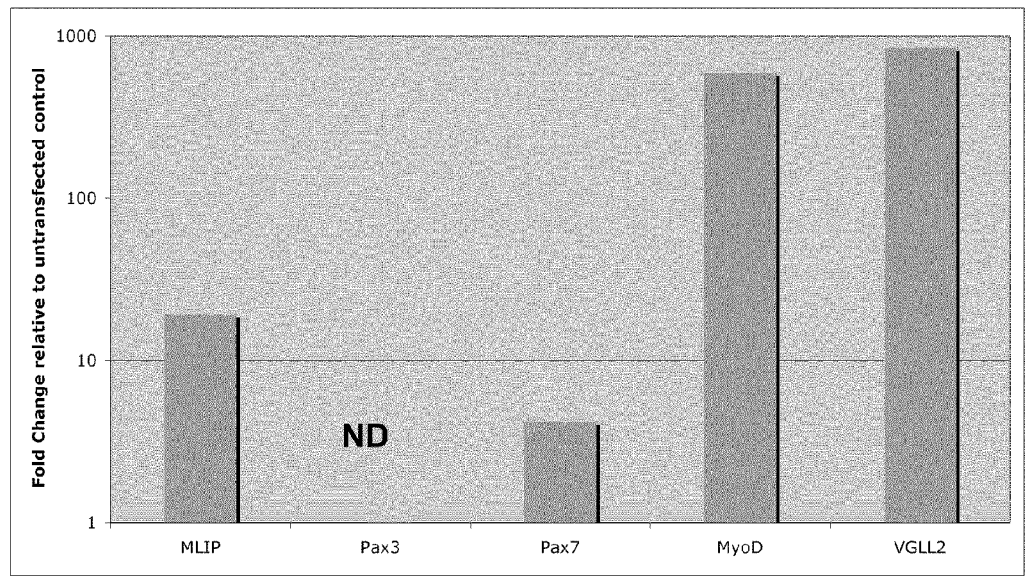
b
Figures 19a-b a
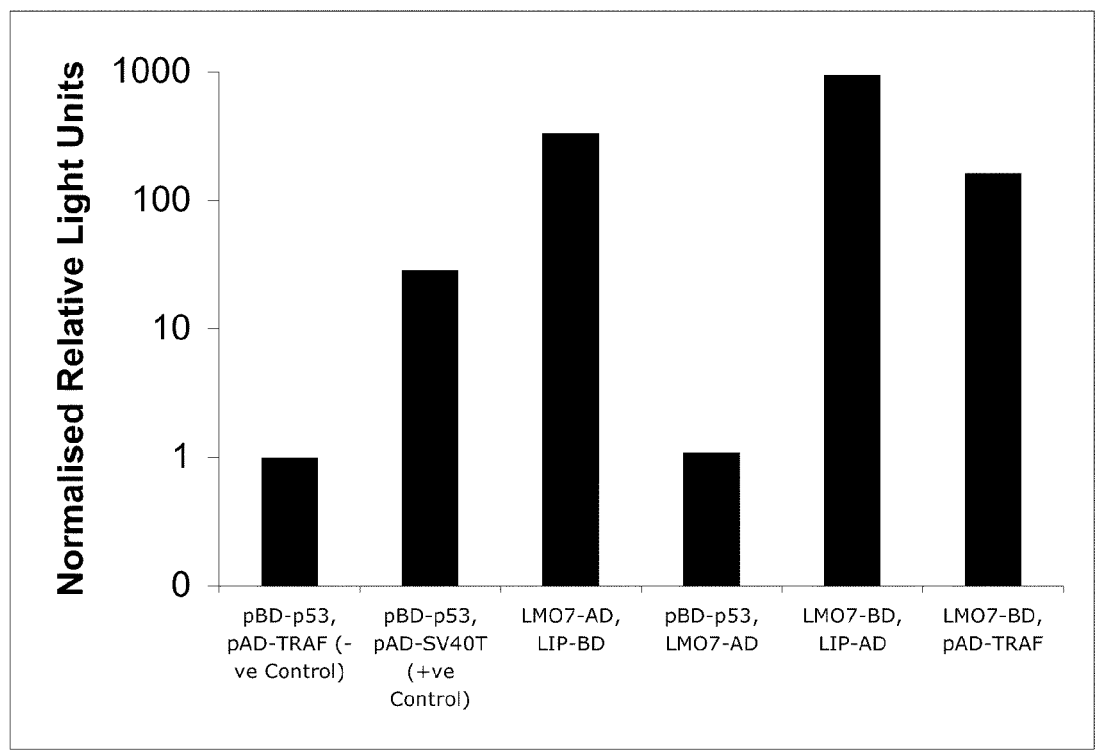
b
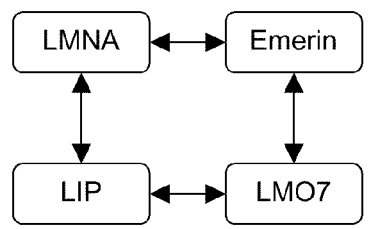
Figures 20a-b

MUSCLE LAMIN A/C INTERACTING PROTEIN, GENE ENCODING SAME, AND USES THEREFOR

CROSS REFERENCE TO RELATED APPLICATIONS

The present application claims the benefit of priority from U.S. provisional patent application Ser. No. 60/956,533, filed Aug. 17, 2007, the entire contents of which are herein incorporated by reference.

FIELD OF THE INVENTION

The present invention relates generally to muscle/brain gene expression in development and disease. More particularly, the present invention relates to muscle lamins and, specifically, a striated muscle and cardiac lamin A/C interacting protein, referred to herein as MLIP, and nucleotide sequences thereof.

BACKGROUND OF THE INVENTION

Lamins are intermediate filament proteins found only in the nuclei of all multicellular eukaryotes. They form stable filaments at the nuclear inner membrane and are fundamentally important for nuclear architecture, chromatin organization and transcriptional regulation of gene expression. Mammalian cells encode both A-type (LMNA) and B-type (LMNB) lamins, which are highly related but can be distinguished on a biochemical and functional basis. LMNA has 12 exons, is localized to human chromosome 1q21.2-q21.3 and generates two protein isoforms, Lamin A and Lamin C through alternative splicing of LMNA2. Together with the outer nuclear membrane and nuclear pore complexes, the inner nuclear membrane forms the nuclear envelope that separates the chromosomes from cytoplasm in eukaryotic cells [2]. Furthermore, Lamin A/C interacts with numerous other proteins, including tissue-specific transcription factors [7].

Laminopathies belong to a heterogeneous group of disorders caused by mutations in the lamin A/C gene (LMNA) that affects a specific combination of tissues, such as heart, skeletal muscle, tendons, neurons, adipocytes and bone. Over 180 different mutations in the LMNA gene have been described. The wide clinical heterogeneity caused by mutations in the LMNA gene supports the hypothesis that Lamin A/C protein performs multiple functions in different tissues. The diseases caused by the wide spectrum of LMNA gene mutations are characterized by the extreme variability of the clinical phenotypes, ranging from cardiac and skeletal myopathies to partial lipodystrophy, peripheral neuropathy, and premature aging. No clear genotype-phenotype correlation has been clarified, since the same mutation can cause different diseases in unrelated families [8-10] and even amongst family members [11, 12]. A recent study, using hierarchical cluster analysis for assembling laminopathies into classes based on organ system involvement, uncovered a non-random relationship between the class of laminopathy and the mutation. These positions were strongly associated (p<0.0001) with the nuclear localization signal sequence of Lamin A/C [13].

One of the seven known laminopathies results in dilated cardiomyopathy (DCM) and is associated with at least eight different clustered missense in the rod 1 domain of Lamin A/C. Alteration of lamin A/C interaction(s) with heart specific factor(s) may be responsible for the pathogenesis of DCM laminopathies. However, the molecular pathogenesis from mutations in the LMNA gene to dilated cardiomyopathy with conduction disease is relatively unknown. Further, the molecular mechanisms for the relationship between tissue specificity of laminopathies and mutations in the LMNA gene are not understood. There remains a need to understand how these different pathologies arise from alterations in the same gene (LMNA) that is almost ubiquitously expressed in adult cells.

The diagnosis of the DCM type of laminopathy is particularly important because of the severity of the cardiac symptoms, which are characterized by conduction system defects, arrhythmias, left ventricular dysfunction, and dilation causing heart failure and subsequent death [14]. Conduction system disease may be observed in the absence of cardiomyopathy [9, 19, 20] or it may proceed cardiac dilation [21]. Severe progression of conduction system disease in laminopathies is typically characterized by sinus node dysfunction, progressive atrioventricular blockage, paroxysmal atrial fibrillation, and frequent premature ventricular beats [8, 9, 17, 20, 22-27]. About half of affected patients suffer sudden cardiac death due to lethal ventricular tachyarrhythmias, despite pacemaker implantation [8, 17, 25, 27-29]. Fibrofatty infiltration of the sinoatrial and the atrioventricular node, as well as the atrioventricular bundle have been described in humans with LMNA mutations as histopathological correlation to their cardiac conduction system disease [22, 24, 25, 30].

Several hypotheses have been proposed for the pathogenesis of laminopathies and most research has been focused on the 'mechanical stress' and 'altered gene regulation' hypotheses. The structural integrity of the nucleus may be affected by the expression of mutant A-type lamins. The fragility of the nuclear envelope is believed to contribute (in part) to pathologies in tissues subject to mechanical stresses, such as skeletal and cardiac muscle. The complete loss of A-type lamins supports this hypothesis.

Many of the proteins that are involved in chromatin organization, transcription and binding to DNA are either directly or indirectly associated with the nuclear envelope. Chromatin organization and transcriptional regulation of gene expression is, therefore, affected in specific ways due to the disruption of the nuclear envelope [34].

The mechanisms by which specific tissue are dramatically affected in laminopathies are not yet known. Knowledge of novel cardiac specific proteins that specifically interacts with lamin A/C would provide a means for diagnosing and treating the pathogenesis of cardiovascular disease and, more particularly, dilated cardiomyopathy with conduction disease.

SUMMARY OF THE INVENTION

It is an object of the present invention to provide a novel muscle specific protein involved in muscular, brain and/or cardiovascular disease or development, and a nucleotide sequence thereof.

In a first aspect of the present invention there is provided nucleotide sequences encoding human or murine muscle lamin A/C interacting protein (hMLIP, mMLIP).

In embodiments of the present invention, the nucleotide sequences comprise a) a nucleotide sequence selected from the group consisting of SEQ ID NOs: 47 to 74; b) a nucleotide sequence which is substantially similar to a sequence selected from the group consisting of SEQ ID NOs: 47 to 74; c) a nucleotide sequence which is homologous to a sequence selected from the group consisting of SEQ ID NOs. 47 to 74; d) a nucleotide sequence which hybridizes to the complement of a sequence selected from the group consisting of SEQ ID NO: 47 to 74; e) a nucleotide sequence which encodes a peptide sequence selected from the group consisting of SEQ ID NOs: 7 to 16; f) a nucleotide sequence selected from the group consisting of SEQ ID NOs: 80 to 106; g) a nucleotide sequence which is substantially similar to a sequence selected from the group consisting of SEQ ID NOs: 80 to 106; h) a nucleotide sequence which is homologous to a sequence selected from the group consisting of SEQ ID NOs. 80 to 106; i) a nucleotide sequence which hybridizes to the complement of a sequence selected from the group consisting of SEQ ID NO: 80 to 106; or j) a nucleotide sequence which encodes a peptide sequence selected from the group consisting of SEQ ID NOs: 75 to 79.

According to the present invention, MLIP can interact with the rod 1 domain of lamin A/C. Preliminary experiments confirmed specific expression of MLIP in the hearts of E11.5 mouse embryos, neonatal and adult mouse hearts, striated muscles and brains. The full length human and mouse MLIP cDNAs have been cloned and at least four MLIP splice variants are evident in both human and mouse. MLIP is located at 6p12.1 of the human chromosome.

In another aspect of the present invention there is provided a transgenic animal comprising a gene sequence encoding cardiac lamin A/C interacting protein. The transgenic animal can comprise a DNA sequence selected from the group consisting of SEQ ID NOs: 1 to 6, 47 to 74 or 80 to 106.

In a further aspect of the present invention there is provided an antibody directed to a muscle lamin A/C interacting protein. The antibody may be directed to the muscle lamin A/C interacting protein encoded by: a) a nucleotide sequence selected from the group consisting of SEQ ID NOs: 47 to 74; b) a nucleotide sequence which is substantially similar to a sequence selected from the group consisting of SEQ ID NOs: 47 to 74; c) a nucleotide sequence which is homologous to a sequence selected from the group consisting of SEQ ID NOs. 47 to 74; d) a nucleotide sequence which hybridizes to the complement of a sequence selected from the group consisting of SEQ ID NO: 47 to 74; e) a nucleotide sequence which encodes a peptide sequence selected from the group consisting of SEQ ID NOs: 7 to 16; f) a nucleotide sequence selected from the group consisting of SEQ ID NOs: 80 to 106; g) a nucleotide sequence which is substantially similar to a sequence selected from the group consisting of SEQ ID NOs: 80 to 106; h) a nucleotide sequence which is homologous to a sequence selected from the group consisting of SEQ ID NOs. 80 to 106; i) a nucleotide sequence which hybridizes to the complement of a sequence selected from the group consisting of SEQ ID NO: 80 to 106; or j) a nucleotide sequence which encodes a peptide sequence selected from the group consisting of SEQ ID NOs: 75 to 79.

The present invention also provides a method for detecting the presence or absence of a muscle lamin A/C interacting protein (MLIP) in a biological sample comprising the steps of: obtaining the biological sample from an animal, and providing a labelled antibody to MLIP to the sample, whereby presence or absence of the label indicates the presence or absence of the MLIP.

In yet another aspect of the present invention, there is provided a kit for detecting the presence or absence of a muscle lamin A/C interacting protein (MLIP) in a biological sample, the kit comprising an antibody to MLIP and instructions for use. In one embodiment, the kit is for detecting the presence or absence of a nucleotide sequence encoding muscle lamin A/C interacting protein (MLIP) in a sample and comprises one or more primers selected from the group consisting of SEQ ID NO: 17 to 46 and SEQ ID NOs: 93 to 94, together with instructions for use.

As shown herein, MLIP may be an important genetic modulator in cardiovascular (including brain and heart) and muscle development and disease.

Other aspects and features of the present invention will become apparent to those ordinarily skilled in the art upon review of the following description of specific embodiments of the invention in conjunction with the accompanying figures.

BRIEF DESCRIPTION OF THE DRAWINGS

Embodiments of the present invention will now be described, by way of example only, with reference to the attached Figures, wherein:

FIG. 1a shows relative MLIP RNA expression levels of four established αMHC-MLIP transgenic mouse lines with evidence of mild hypertrophy.

FIG. 1b shows preliminary heart to body weight ratios determined for each of the established αMHC-MLIP transgenic mouse lines.

FIGS. 2a-c show representative electrocardiographic profiles of a) αMHC-MLIP transgenic mouse Line 39 (n=6); b) αMHC-MLIP transgenic mouse Line 49 (n=4); and c) control mice (n=8).

FIG. 2d shows comparative heart rates in the MLIP transgenic mouse lines compared to control mice.

FIG. 2e shows comparative P-R intervals of MLIP transgenic mouse lines compared to control mice.

FIGS. 3a-c shows histological analysis of a) five week old wildtype mouse; b) a first five week old αMHC MLIP transgenic mouse line in accordance with the present invention; and c) a second five week old αMHC-MLIP transgenic mouse line in accordance with the present invention.

FIGS. 4a-b show endogenous MLIP localized to both the nucleus and cytosol of rat neonatal myocytes at a) 40× magnification and b) 100× magnification. FIG. 4c shows C2C12 cells co-stained with specific polyclonal antibodies for MLIP and PML. FIG. 4d shows in situ MLIP in mouse brain localized to the hippocampus and in FIG. 4e, endogenous MLIP (red) was localized to the nuclei and cytosol of rat hippocampal neurons and glial cells.

FIG. 5a illustrates two major splice variants of MLIP were cloned from mouse heart. FIG. 5b shows a western blot analysis of bacterial-expressed $His_6$-MLIP and GST-Lamin recombinant proteins.

FIGS. 6a-b show specific expression of MLIP in a) mouse tissue and b) human tissue, by Northern analysis. FIG. 6c shows normalized tissue distribution of MLIP expression in adult mouse as determined by real time PCR.

FIGS. 7a-b show specific induction of MLIP expression during P19 cardiomyogenesis, illustrating P19 differentiation into a) cardiac cells in the presence of dimethyl sulfoxide (DMSO); and b) neuronal and glial cells in the presence of retinoic acid.

FIG. 8a shows an RT-PCR expression profile of MLIP during the critical phase of the perinatal heart's exit from the cell cycle. FIG. 8b shows a corresponding Western blot.

FIG. 12 shows MLIP expression in C2C12 cells during myotube formation by indirect immunoflorescence staining with a MLIP specific antibody.

FIG. 18 shows the results of direct cloning of MLIP. FIG. 18a shows RT-PCR results. FIG. 18b is an alternative splice map of MLIP.

FIG. 19 shows representative expression profiles a) for muscle specific genes, and b) following overexpression of MLIP.

FIGS. 20a-b show results of yeast-two hybrid of MLIP and LMO7.

DETAILED DESCRIPTION

Figure 6D:
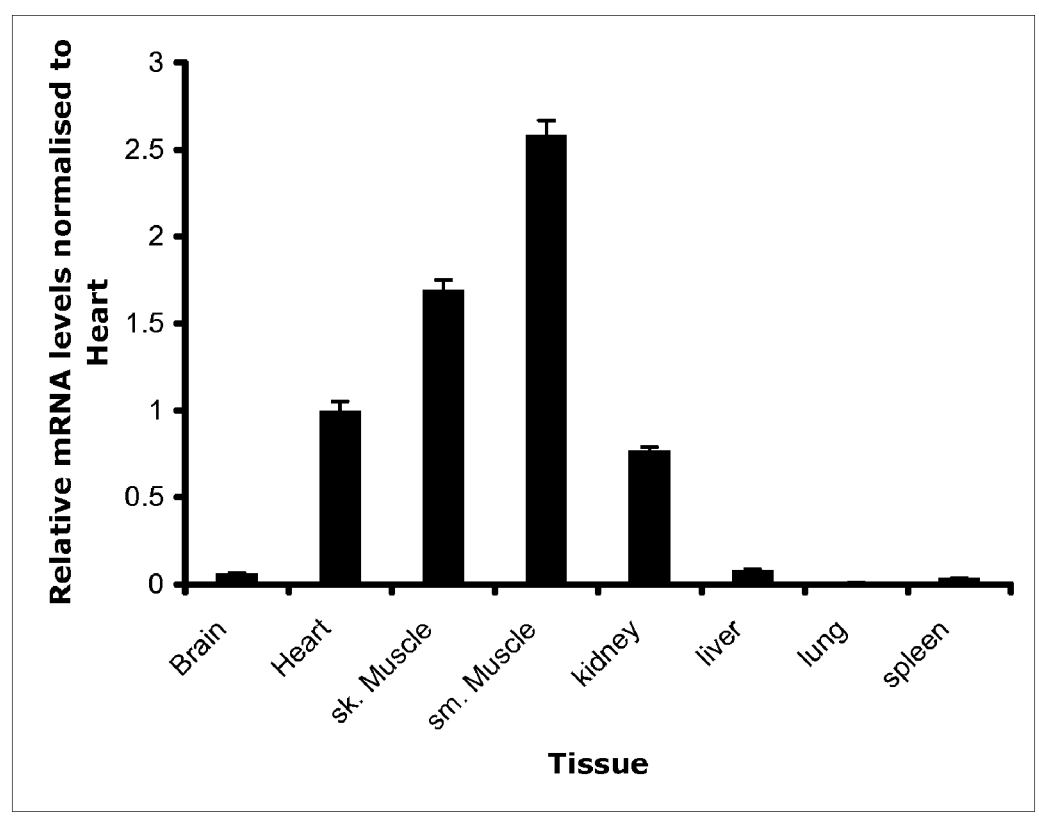
FIG. 6d shows relative mRNA levels of MLIP in different tissues.

Generally, the present invention provides novel human and mouse gene sequences encoding muscle lamin A/C interacting protein (hMLIP and mMLIP). The sequences comprise: a) a nucleotide sequence selected from the group consisting of SEQ ID NOs: 47 to 74; b) a nucleotide sequence which is substantially similar to a sequence selected from the group consisting of SEQ ID NOs: 47 to 74; c) a nucleotide sequence which is homologous to a sequence selected from the group consisting of SEQ ID NOs. 47 to 74; d) a nucleotide sequence which hybridizes to the complement of a sequence selected from the group consisting of SEQ ID NO: 47 to 74; e) a nucleotide sequence which encodes a peptide sequence selected from the group consisting of SEQ ID NOs: 7 to 16; f) a nucleotide sequence selected from the group consisting of SEQ ID NOs: 80 to 106; g) a nucleotide sequence which is substantially similar to a sequence selected from the group consisting of SEQ ID NOs: 80 to 106; h) a nucleotide sequence which is homologous to a sequence selected from the group consisting of SEQ ID NOs. 80 to 106; i) a nucleotide sequence which hybridizes to the complement of a sequence selected from the group consisting of SEQ ID NO: 80 to 106; or j) a nucleotide sequence which encodes a peptide sequence selected from the group consisting of SEQ ID NOs: 75 to 79.

The genes in accordance with the present invention, and the proteins expressed therefrom, are useful for studies of regulation of myocyte development, proliferation, regeneration and/or disease and for identification of regulatory substances having impact on developmental or disease-associated outcomes, particularly in the cardiovascular sciences. Furthermore, transgenic animals comprising the gene can be used as a model to examine regulation of myocyte development, proliferation, regeneration or disease and identification of novel drug targets muscle and cardiovascular disease, and muscle regeneration. Loss or mis-regulation of MLIP may contribute to alterations in cardiac development. Further, loss or mis-regulation of MLIP may contribute to the onset and development of dilated cardiomyopathy with conduction disease. This is suggested by data obtained from investigating the effects of altered gene expression of MLIP in murine models as described herein. Preliminary investigation suggests that MLIP may be associated with the simultaneous development of both Dunnigans-type familial partial lipodystrophy (non-striated muscle laminopathy) and dilated cardiomyopathy. MLIP may also be involved in other muscular dystrophies, not necessarily cardiac related. Furthermore, MLIP expression in terminally differentiated cells of brain, muscle and heart may play a role in normal development, disease and regeneration.

Identification and initial characterization of a novel Lamin A/C interacting protein, MLIP: To identify heart specific proteins that interact with the rod 1 domain of lamin A/C, a yeast two-hybrid interaction screen was utilized. Proteins encoded by a human heart complementary DNA library (Clontech) were screened for their ability to interact with the rod 1 domain of Lamin A/C. Of the $3.5 \times 10^6$ independent clones screened, 232 clones were positive in the presence of the rod 1 domain of lamin A/C; thus, the DNA sequence of the 232 positive clones were determined. The MLIP clone, which was represented by 6 independent clones out of the 232, was found to be homologous to 49 expressed sequence tags (ESTs) present within GenBank™ online database. The clone was mapped to human chromosome 6p12.1 and subsequently identified as a putative open reading frame (C6orf142, GenBank accession number: NM_138569). The mouse homologue is mapped to mouse chromosome 9E.

The MLIP cDNA clone contains 13 exons that span over 247 kilobases and is predicted to translate a 458 amino-acid protein. Comparisons of the deduced 458-amino-acid protein, or the nucleic acid sequence with the GenBank database, revealed no substantial similarities with any other protein other than homologous forms in non-human genomes or EST databases. Initially, no structural or functional domain was identified within the primary amino acid sequence or the nucleic acid sequence of MLIP.

Mouse MLIP DNA shRNAi sequences are provided (SEQ ID NO: 1 to 6). Putative amino acid sequences corresponding to mouse MLIP DNA sequence fragments were determined (SEQ ID NOs: 7 to 16). PCR primers for mouse MLIP (SEQ ID NOs: 17 to 46) were constructed to generate PCR products forming contigs (SEQ ID NOs: 47 to 56 and 58 to 74) to construct the entire mouse MLIP gene (SEQ ID NO: 57). PCR primers for human MLIP (SEQ ID NOs: 93-94) were used to generate PCR products forming contigs of the various splice variants (SEQ ID NOs: 80 to 87 and 89 to 106) of the full length sequence of the human MLIP gene (SEQ ID NO: 88). Putative human peptide sequences were obtained (SEQ ID NOs: 75 to 79).

Figure 14:
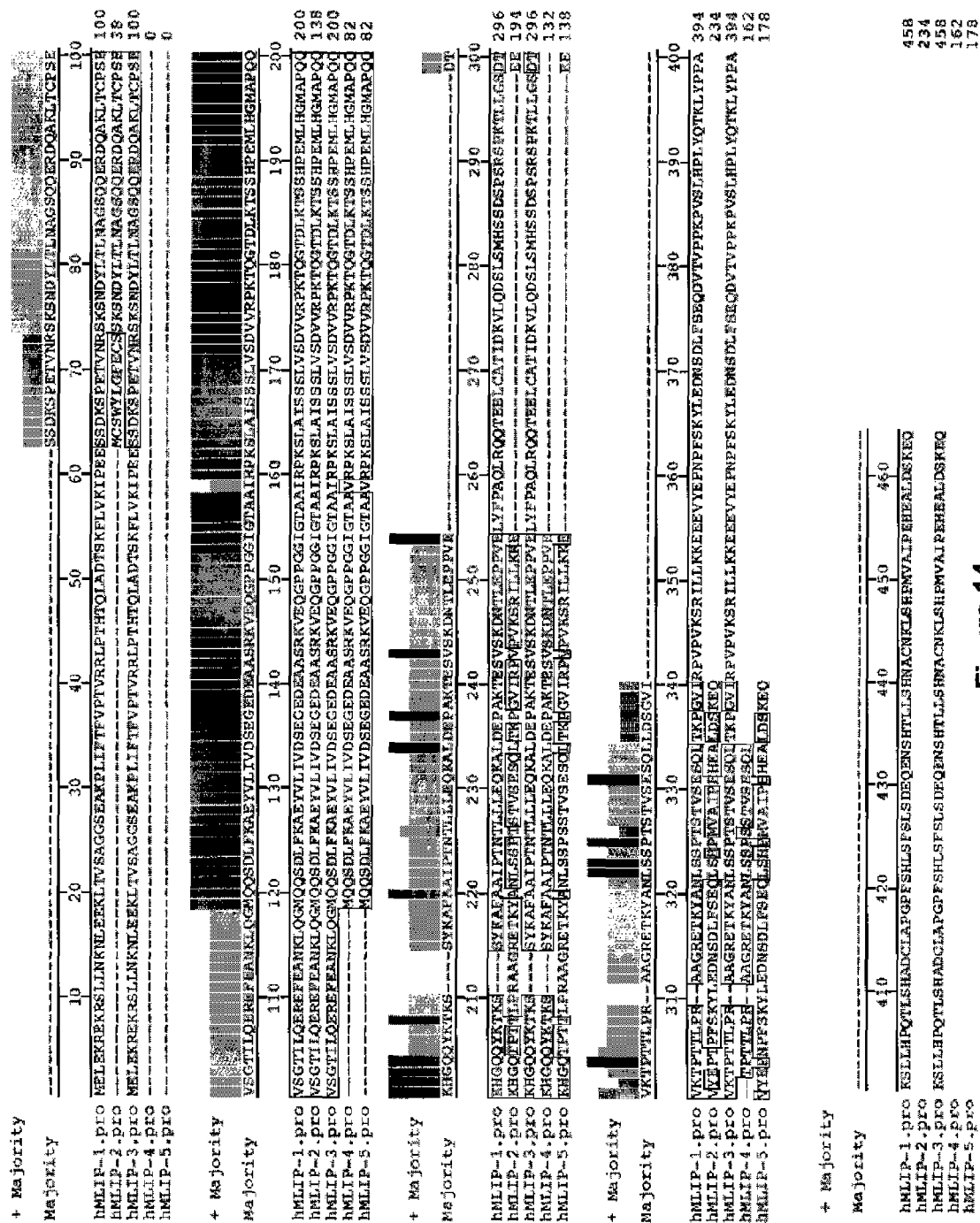
FIG. 14 shows an amino acid sequence alignment of human MLIP proteins hMLIP-1, hMLIP-2, hMLIP-3, hMLIP-4 and hMLIP-5. The amino acid sequences were translated from the five different human MLIP nucleotide sequences cloned (SEQ ID NOs: 80 to 106) from a pooled human cDNA library.
Figure 15:
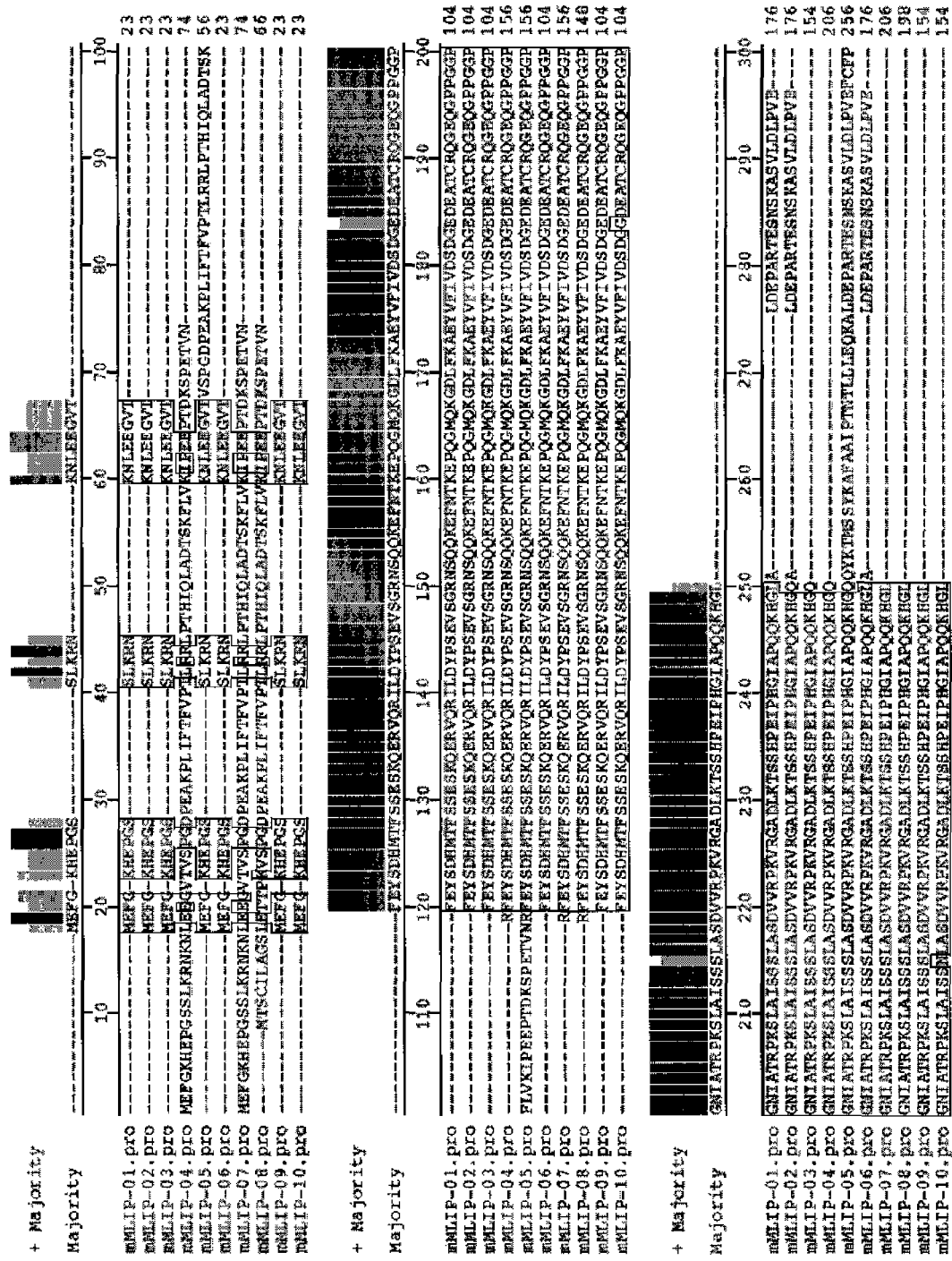
FIG. 15 shows an amino acid sequence alignment of mouse MLIP proteins mMLIP-01, mMLIP-02, mMLIP-03, mMLIP-04, mMLIP-05, mMLIP-06, mMLIP-07, mMLIP-08, mMLIP-09 and mMLIP-10. The amino acid sequences were translated from the ten different mouse MLIP nucleotide sequences cloned (SEQ ID NOs: 47 to 74) from a pooled mouse heart cDNA library
Figure 15:
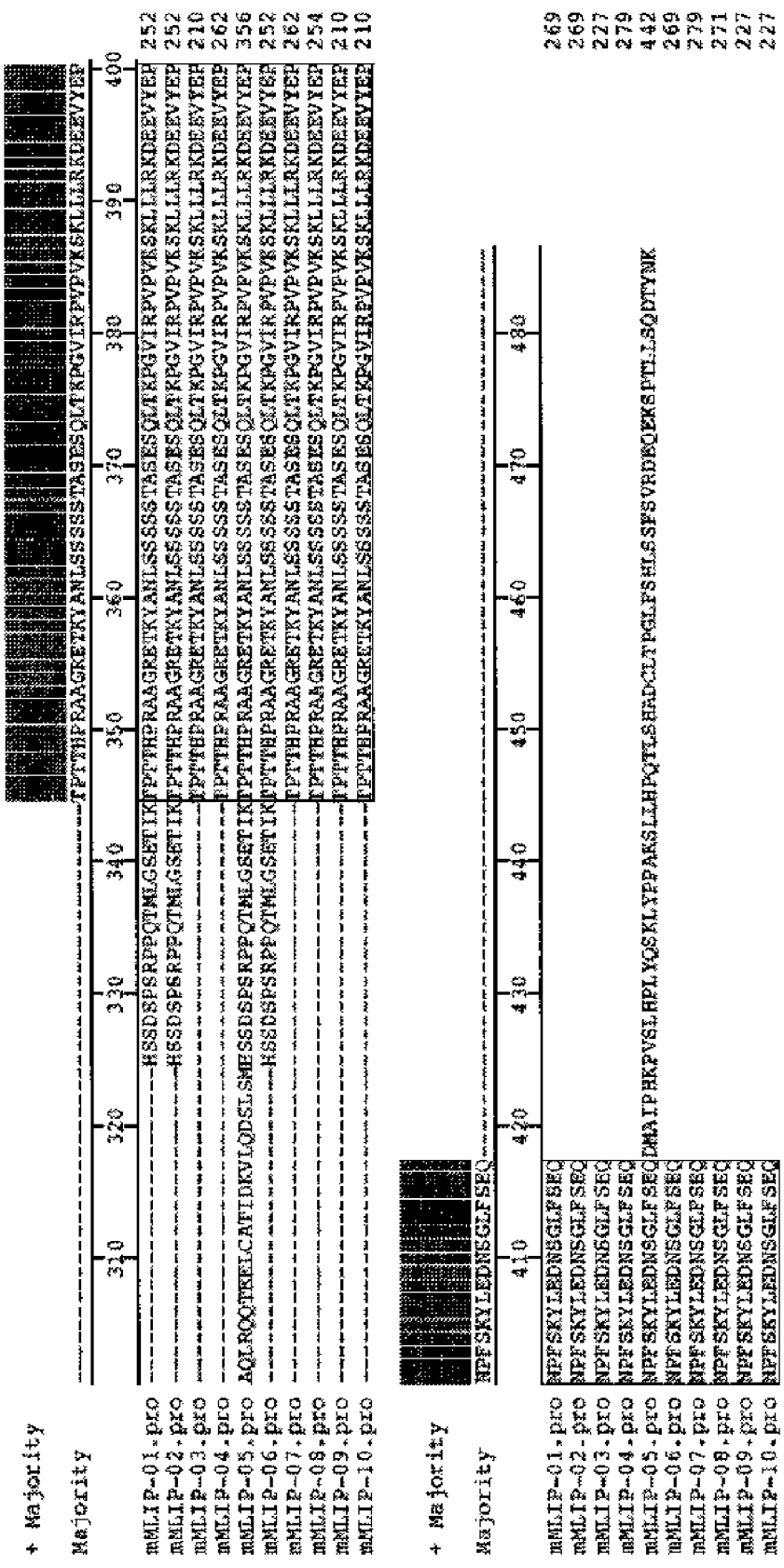
Figure 16:
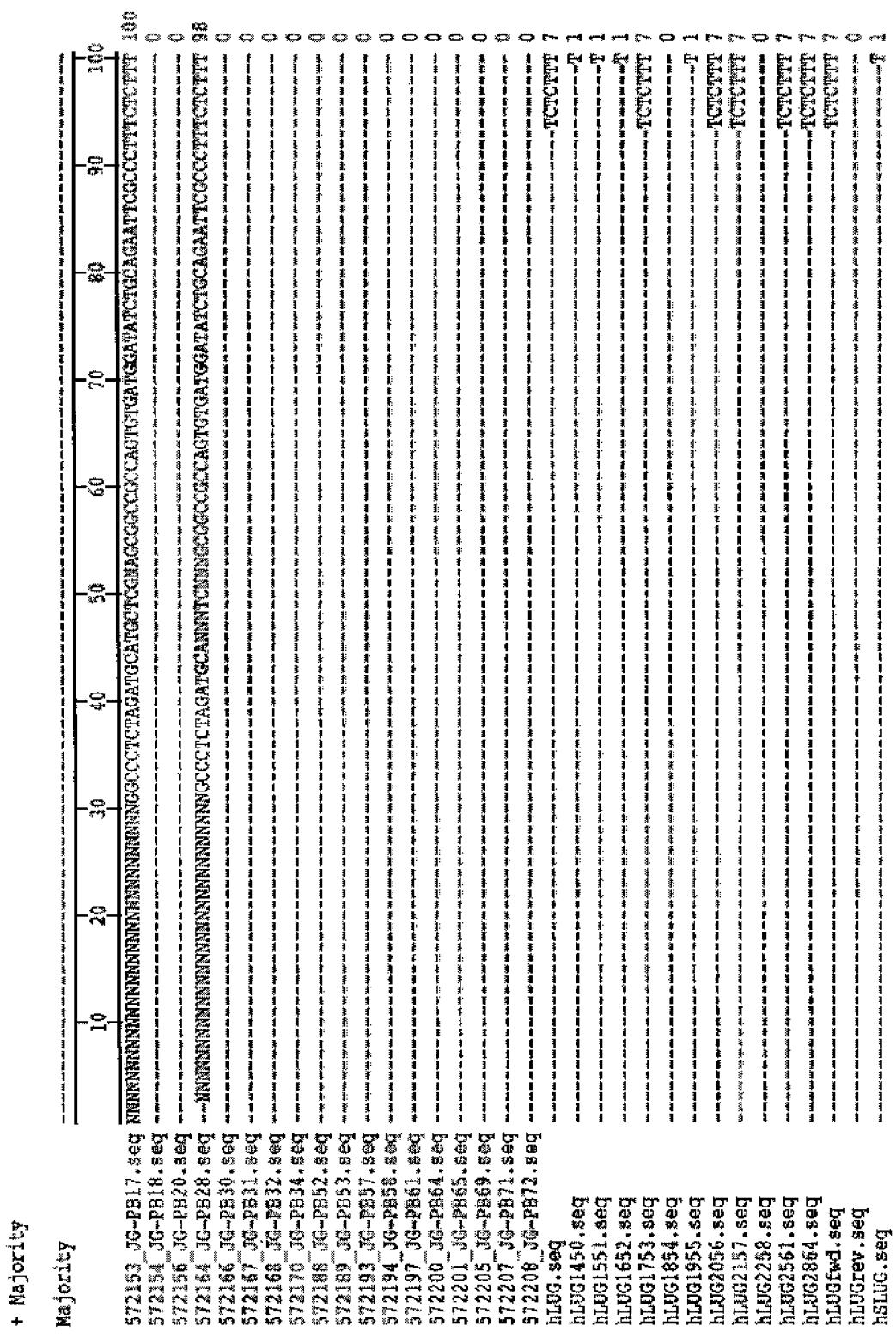
FIG. 16 shows a nucleotide sequence alignment of human MLIP nucleotide sequences cloned (SEQ ID NOs: 80 to 106) from a pooled human cDNA library.
Figure 16:
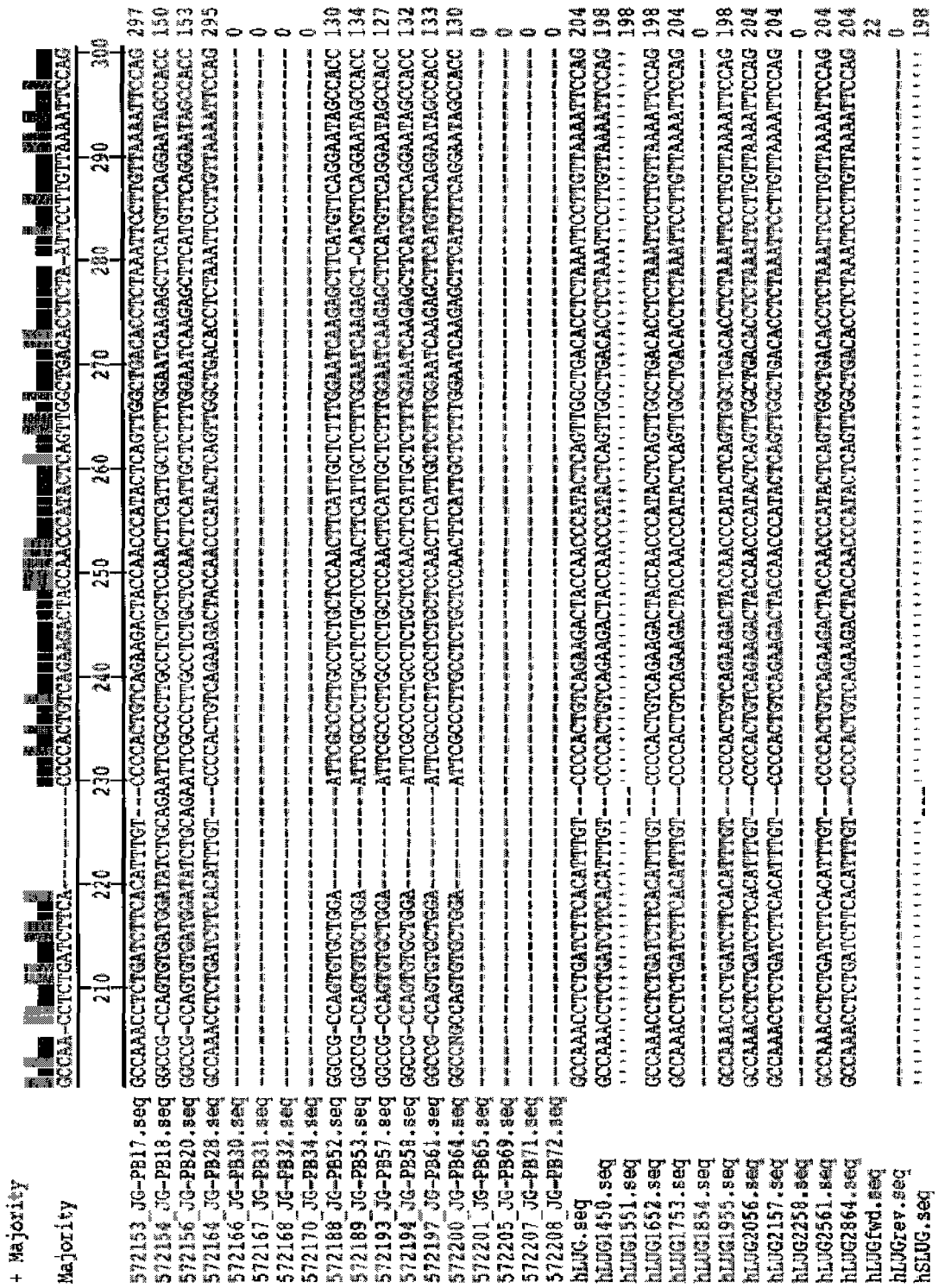
Figure 16:
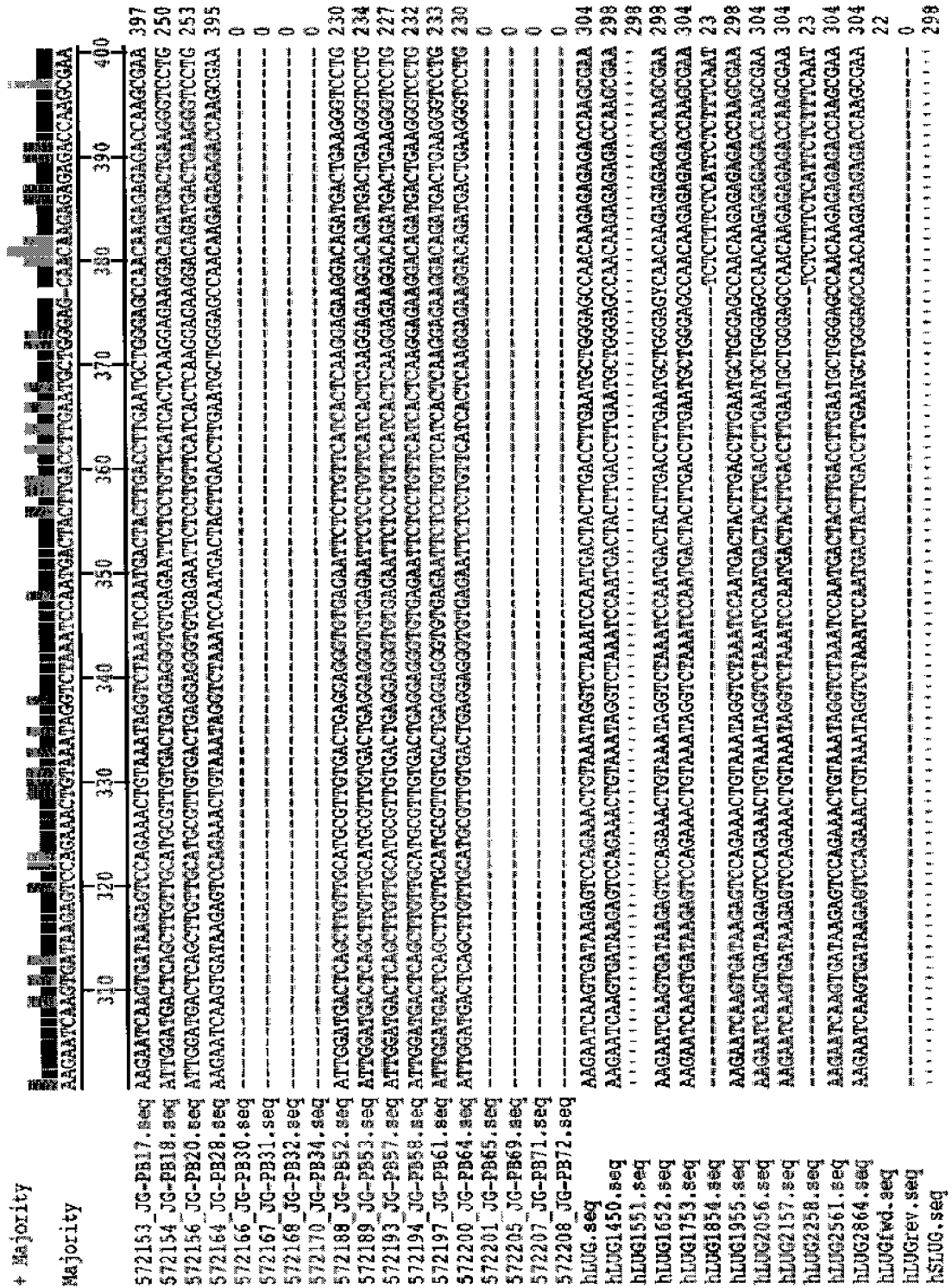
Figure 16:
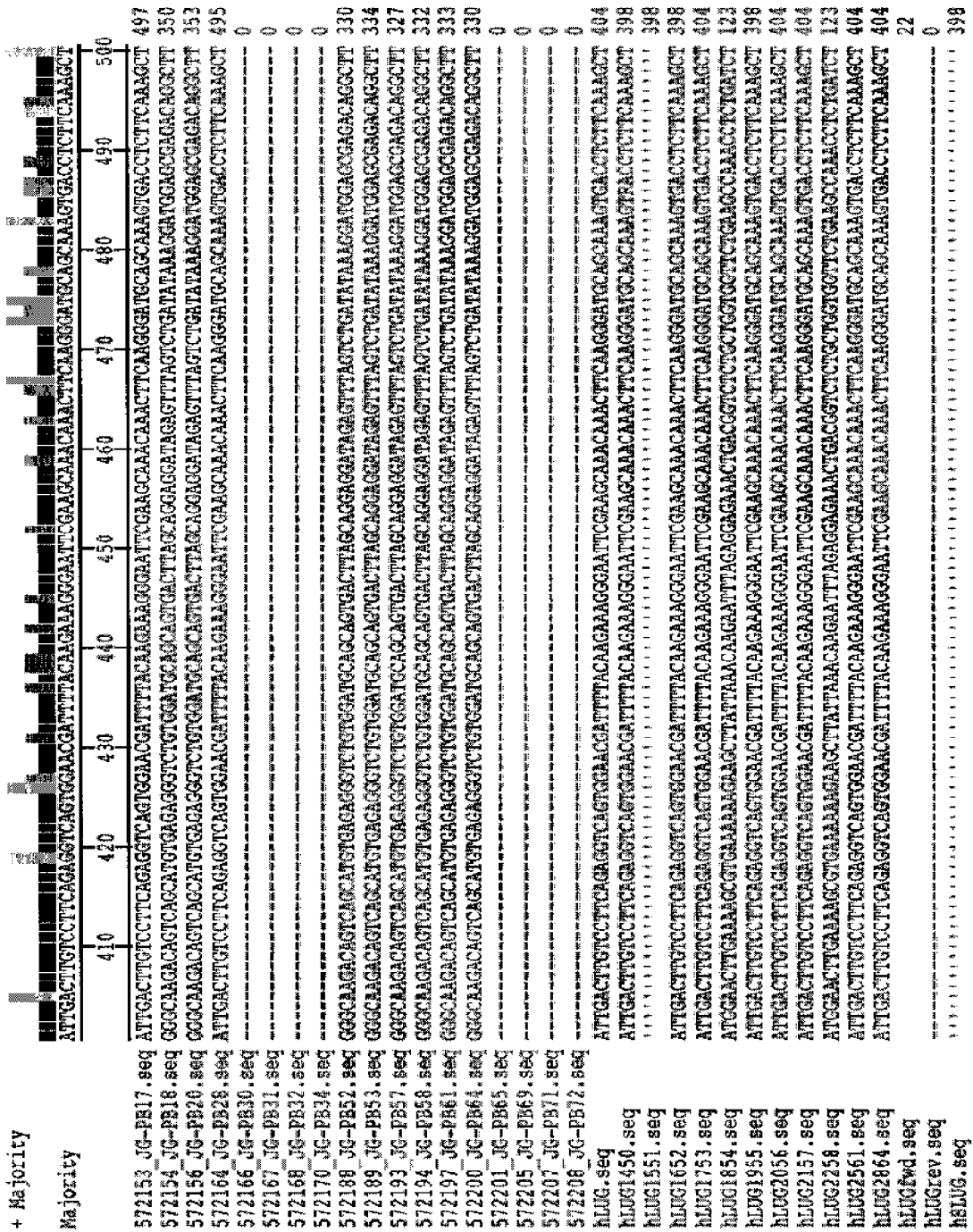
Figure 16:
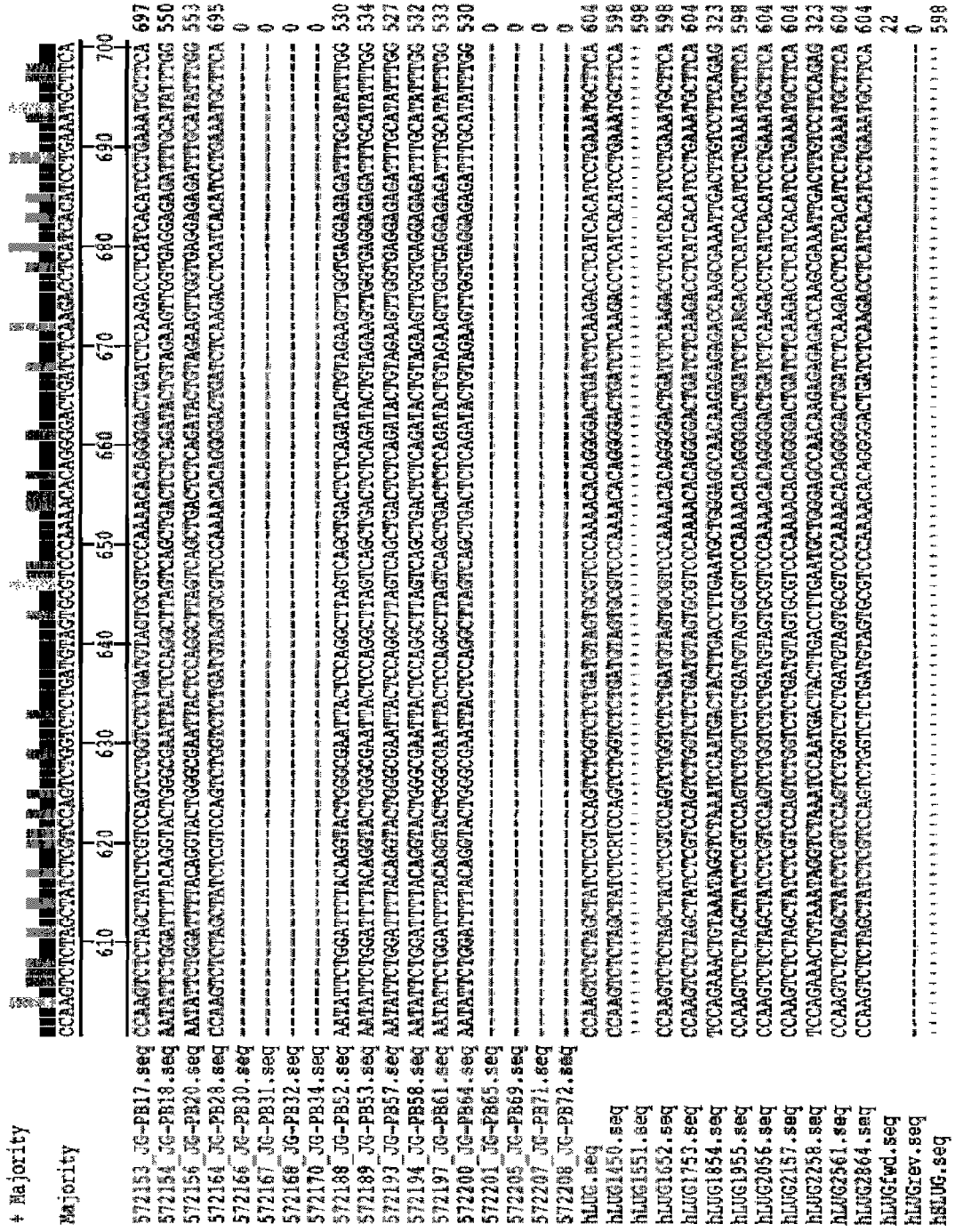
Figure 16:
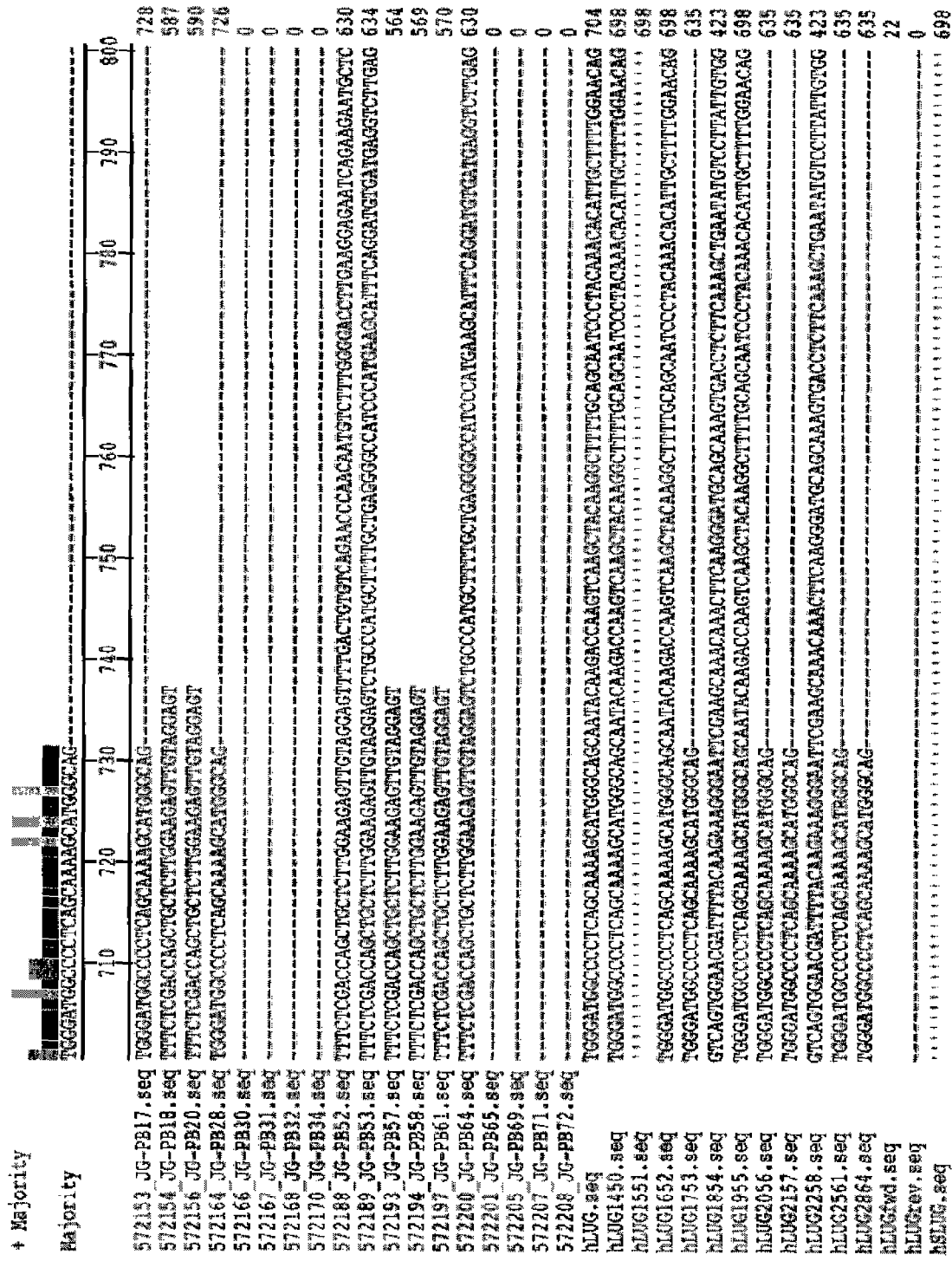
Figure 16:
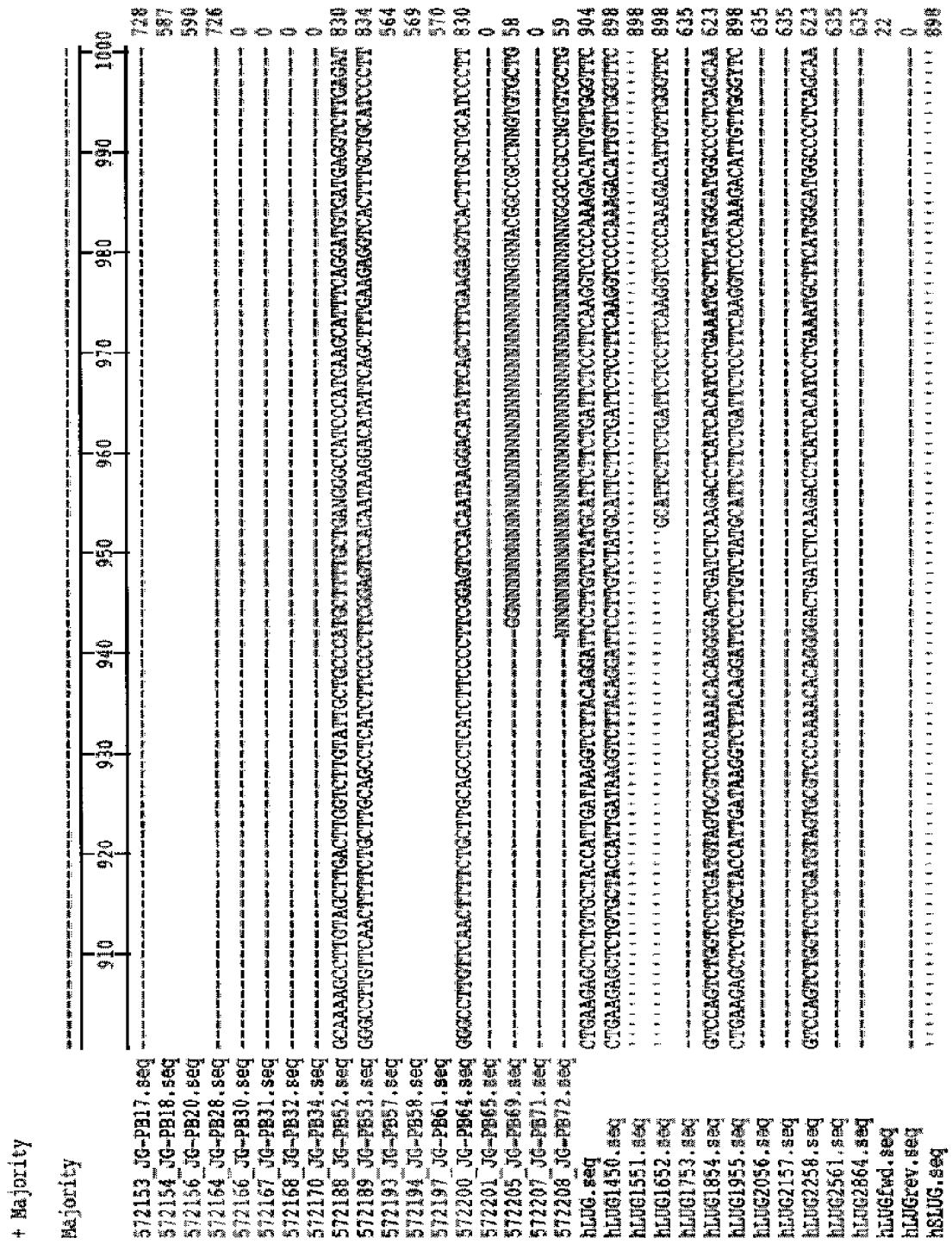
Figure 16:
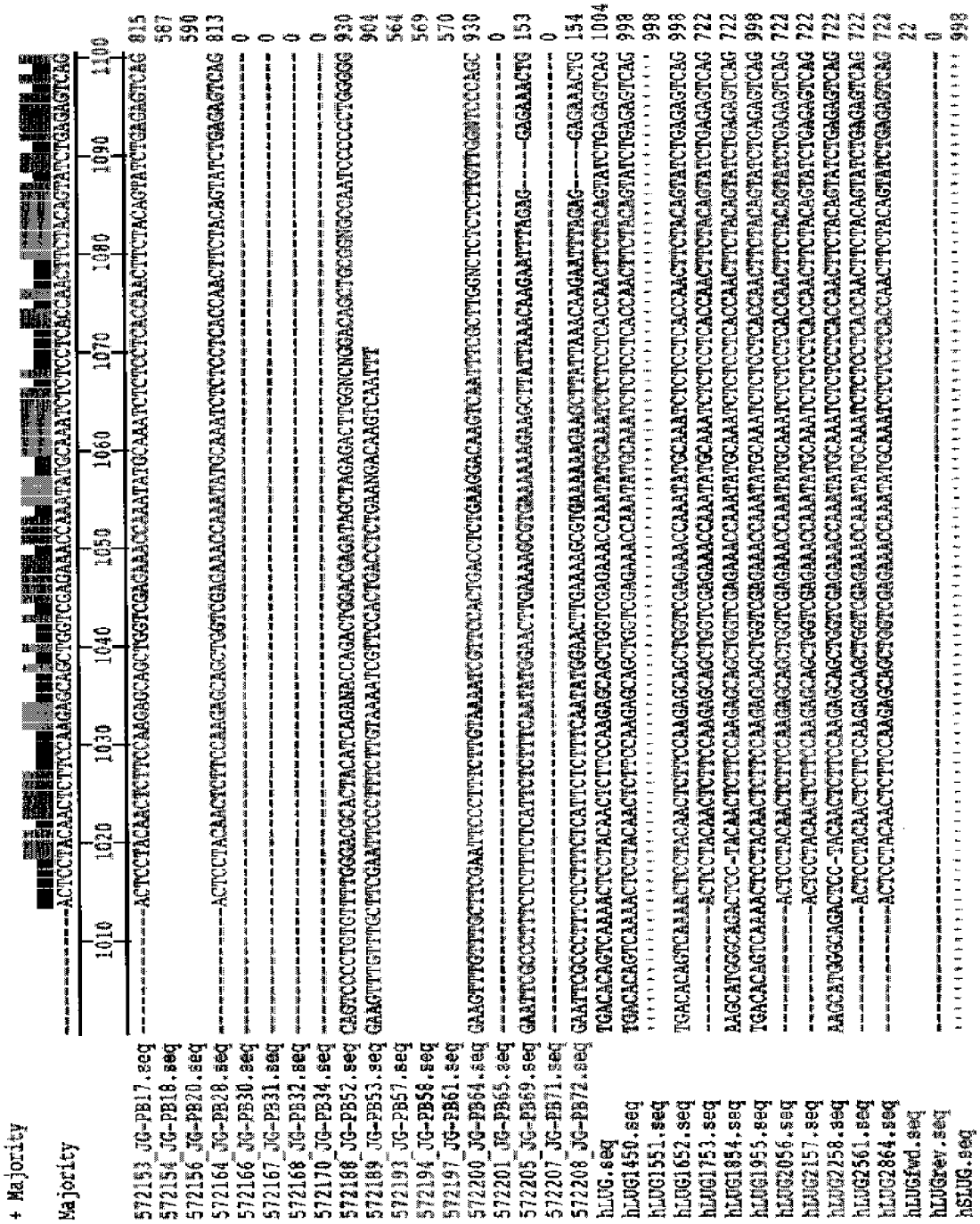
Figure 16:
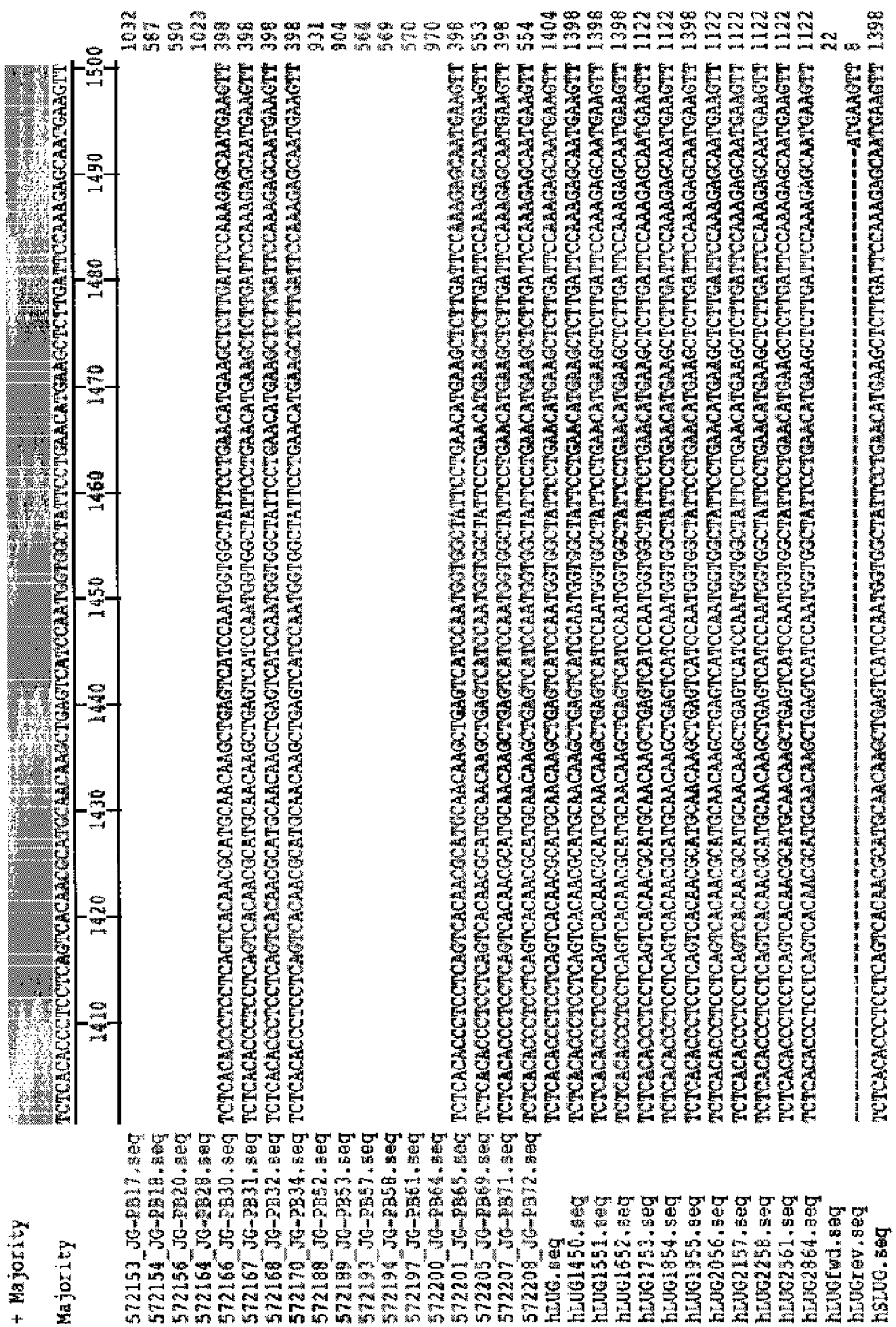
Figure 16:
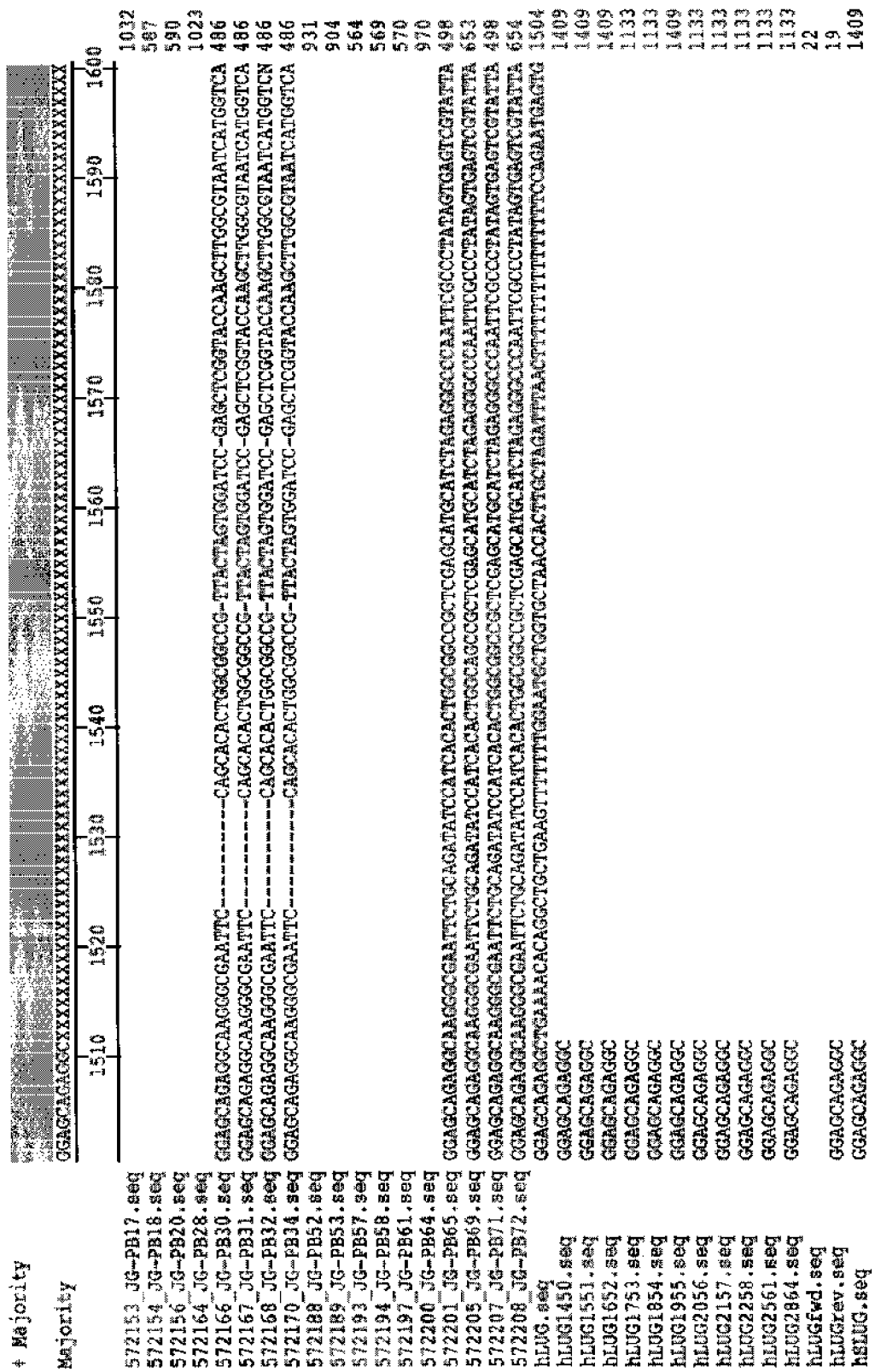
Figure 16:
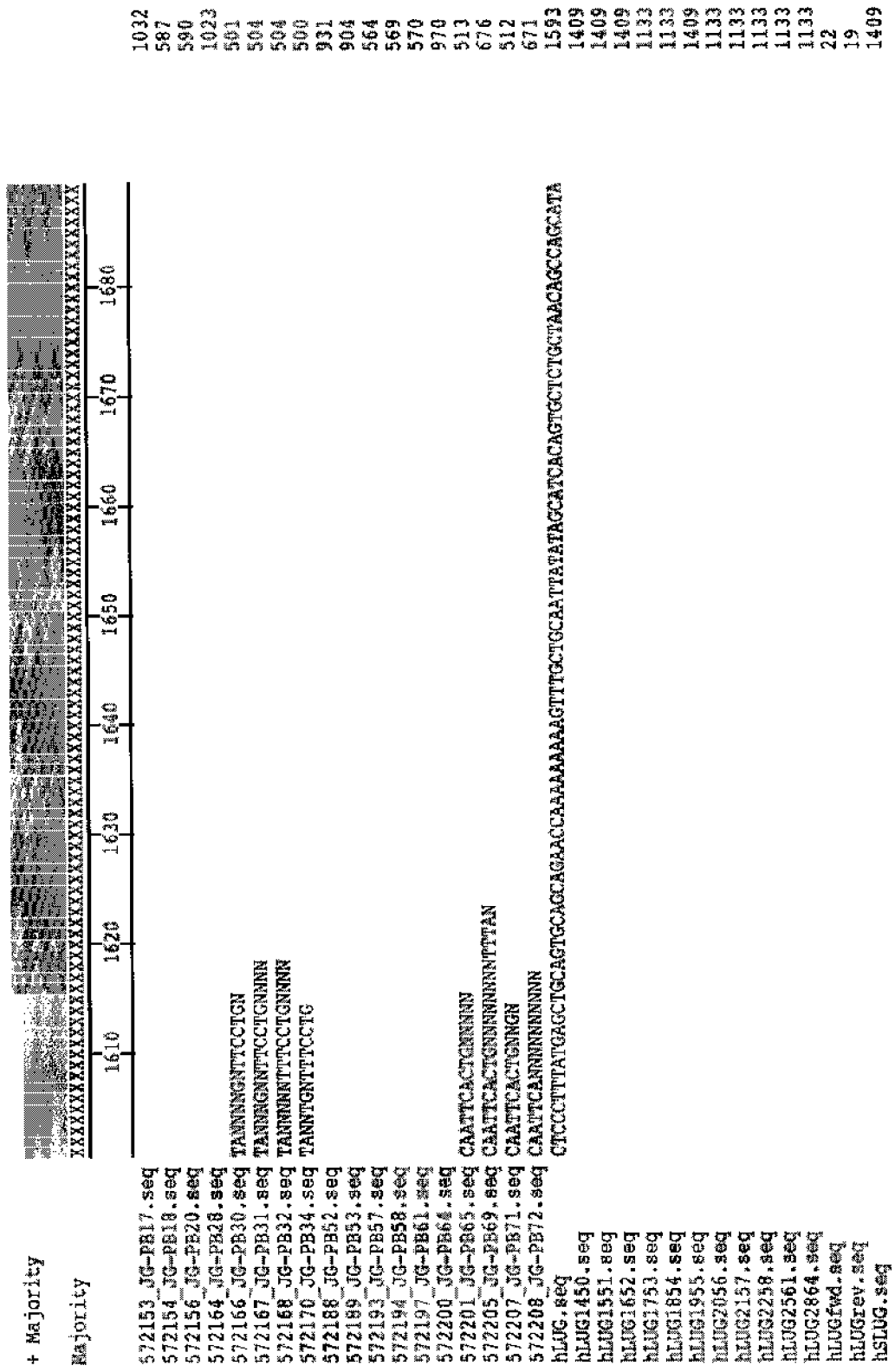
Figure 17:
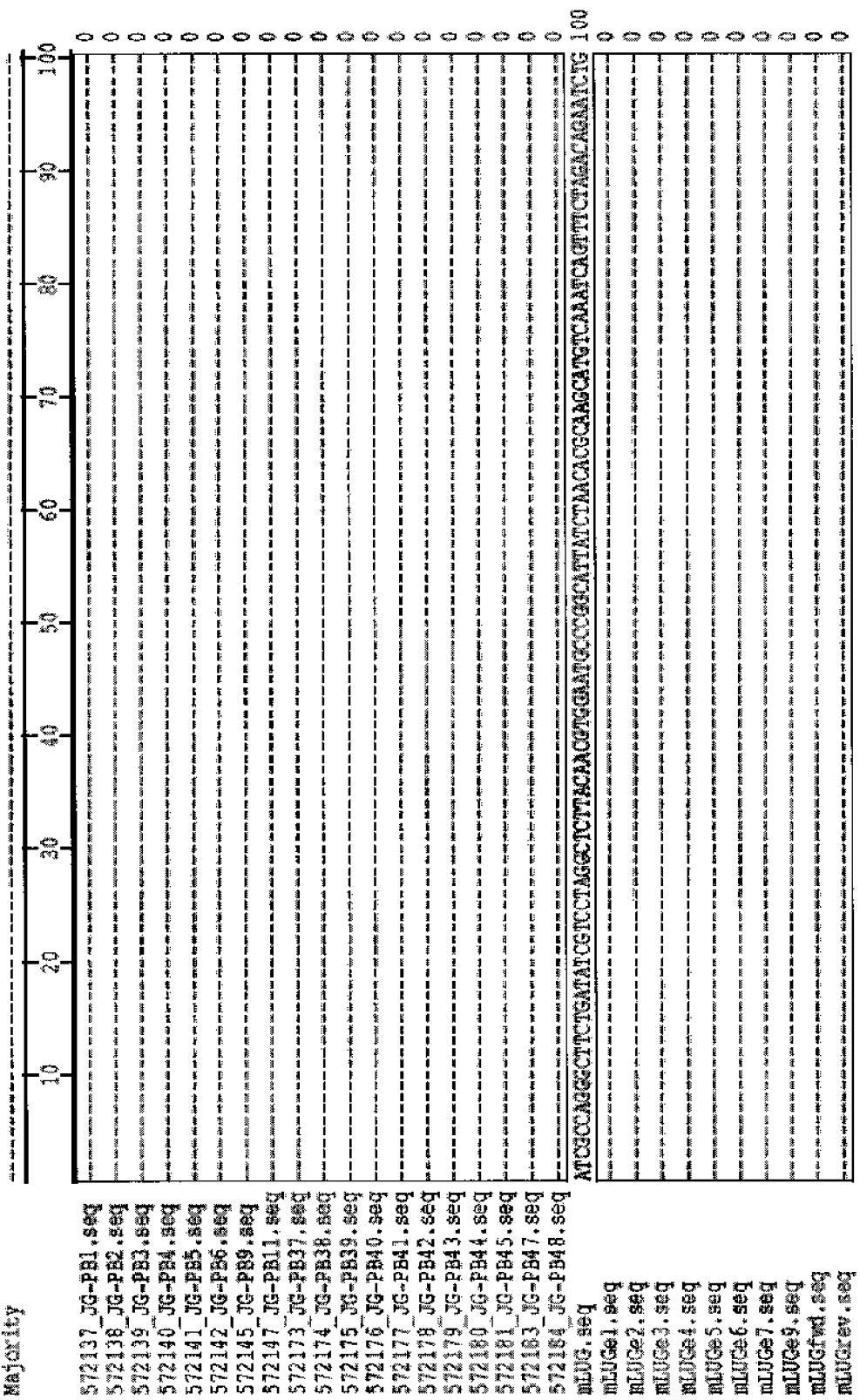
FIG. 17 shows a nucleotide sequence alignment of mouse MLIP nucleotide sequences cloned (SEQ ID NOs: 47 to 74) from a pooled mouse heart cDNA library.
Figure 17:
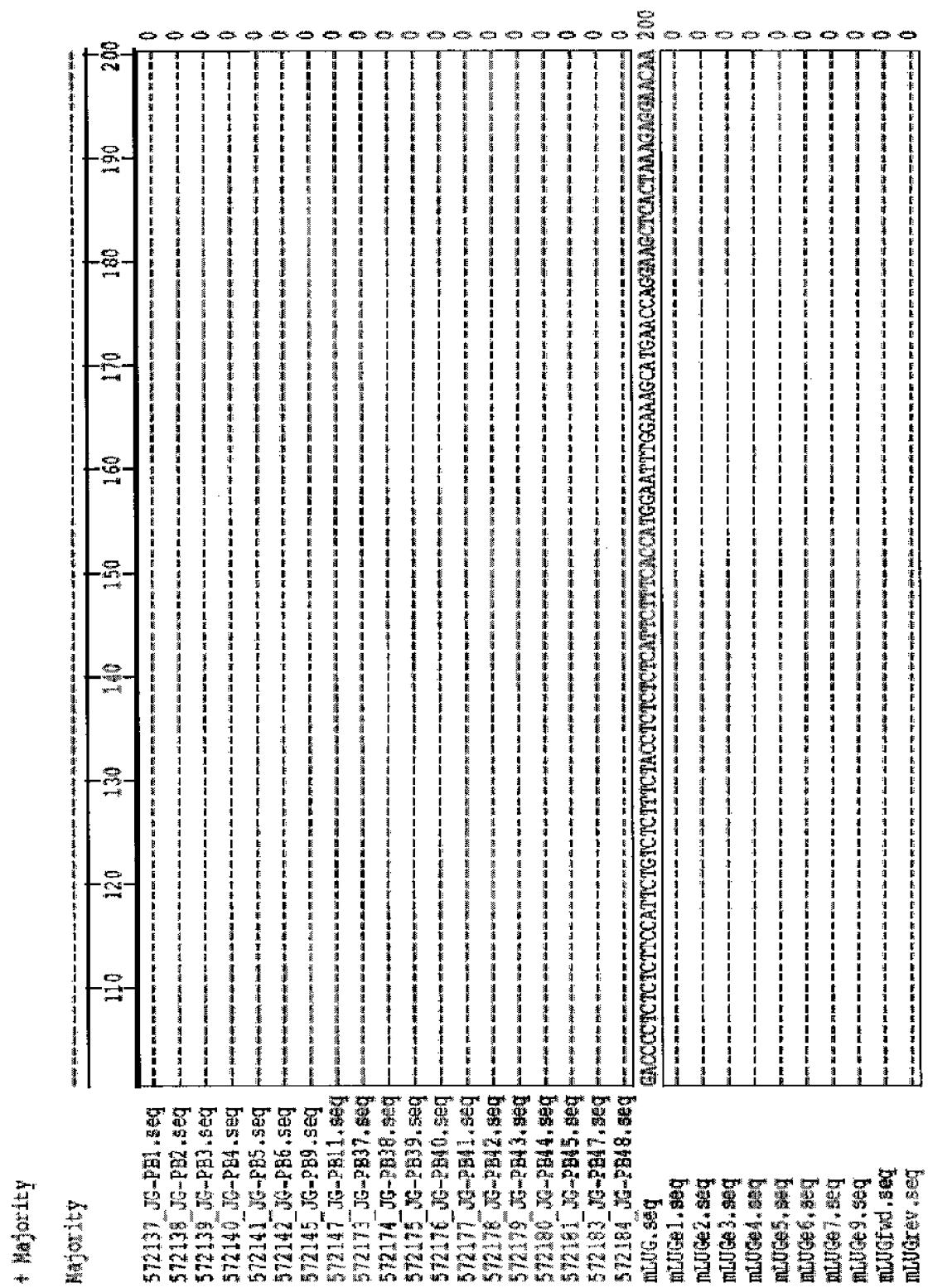
Figure 17:
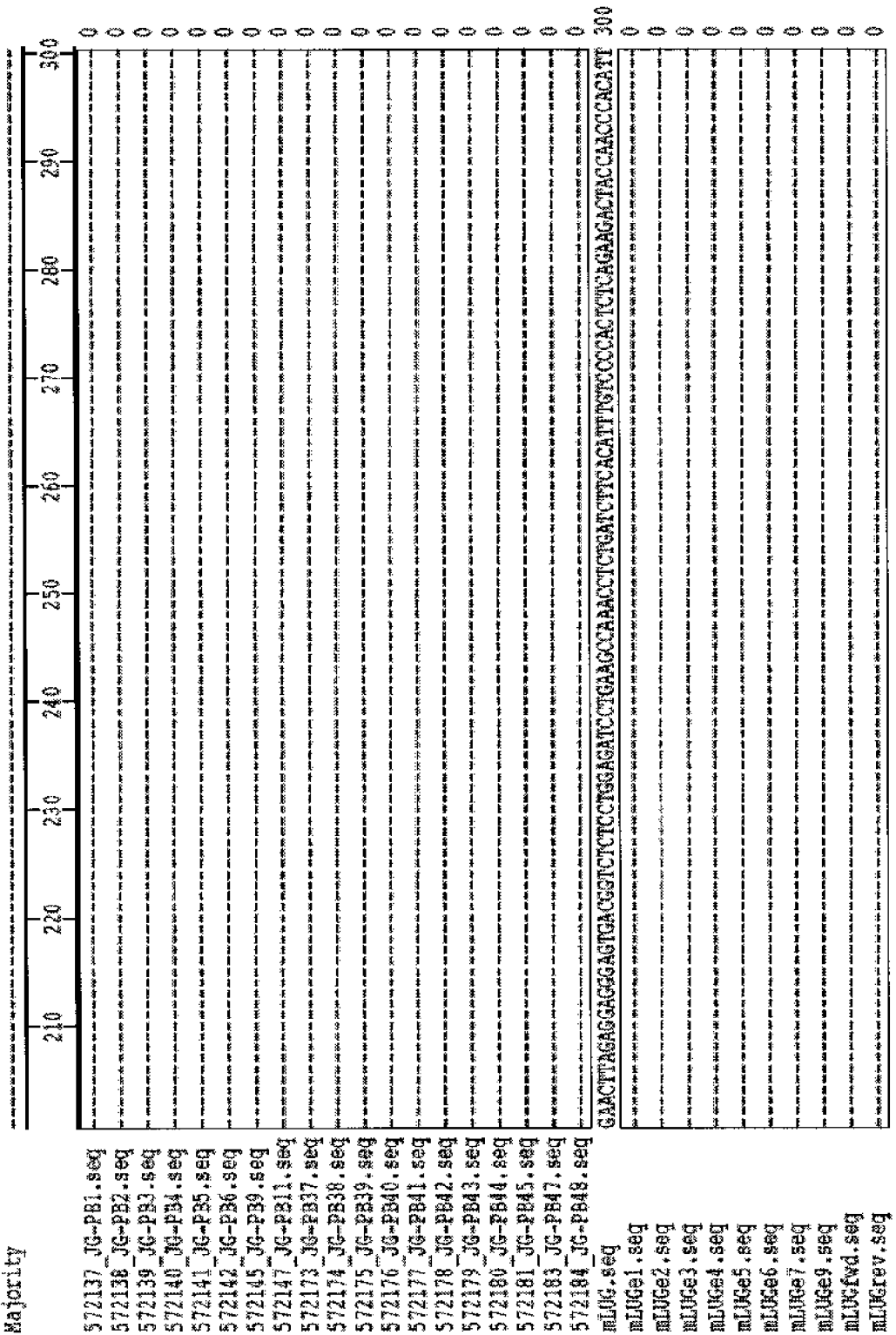
Figure 17:
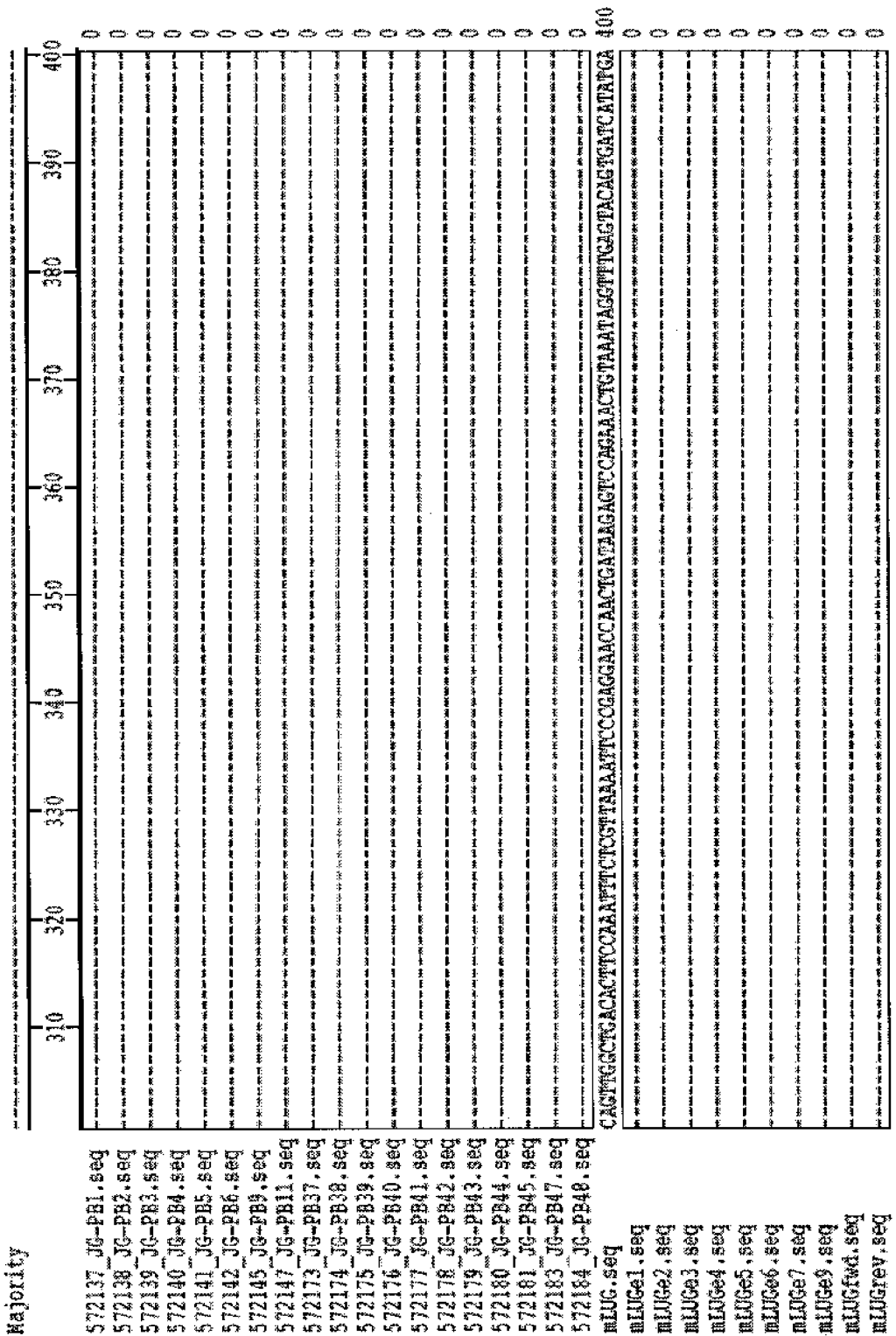
Figure 17:
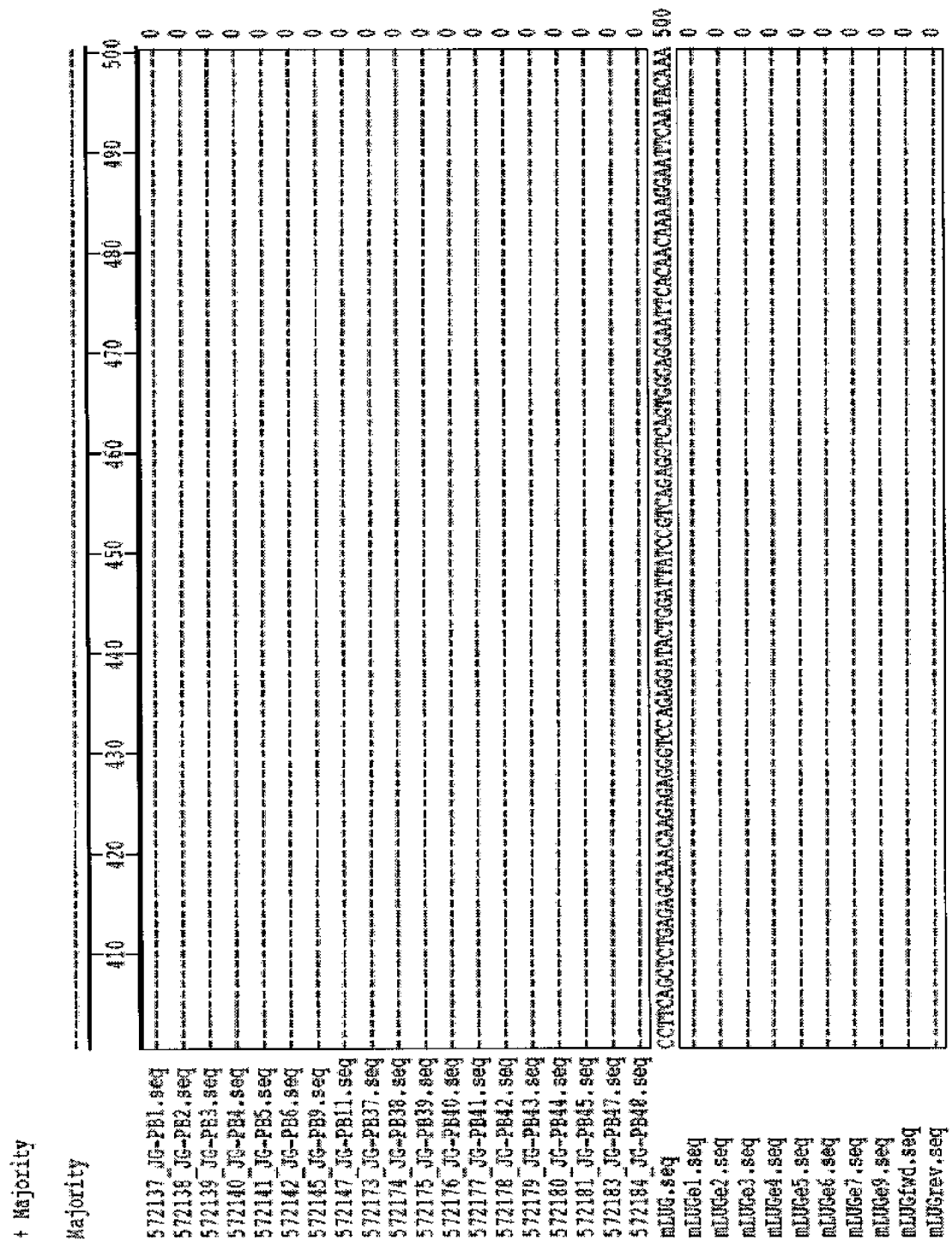
Figure 17:
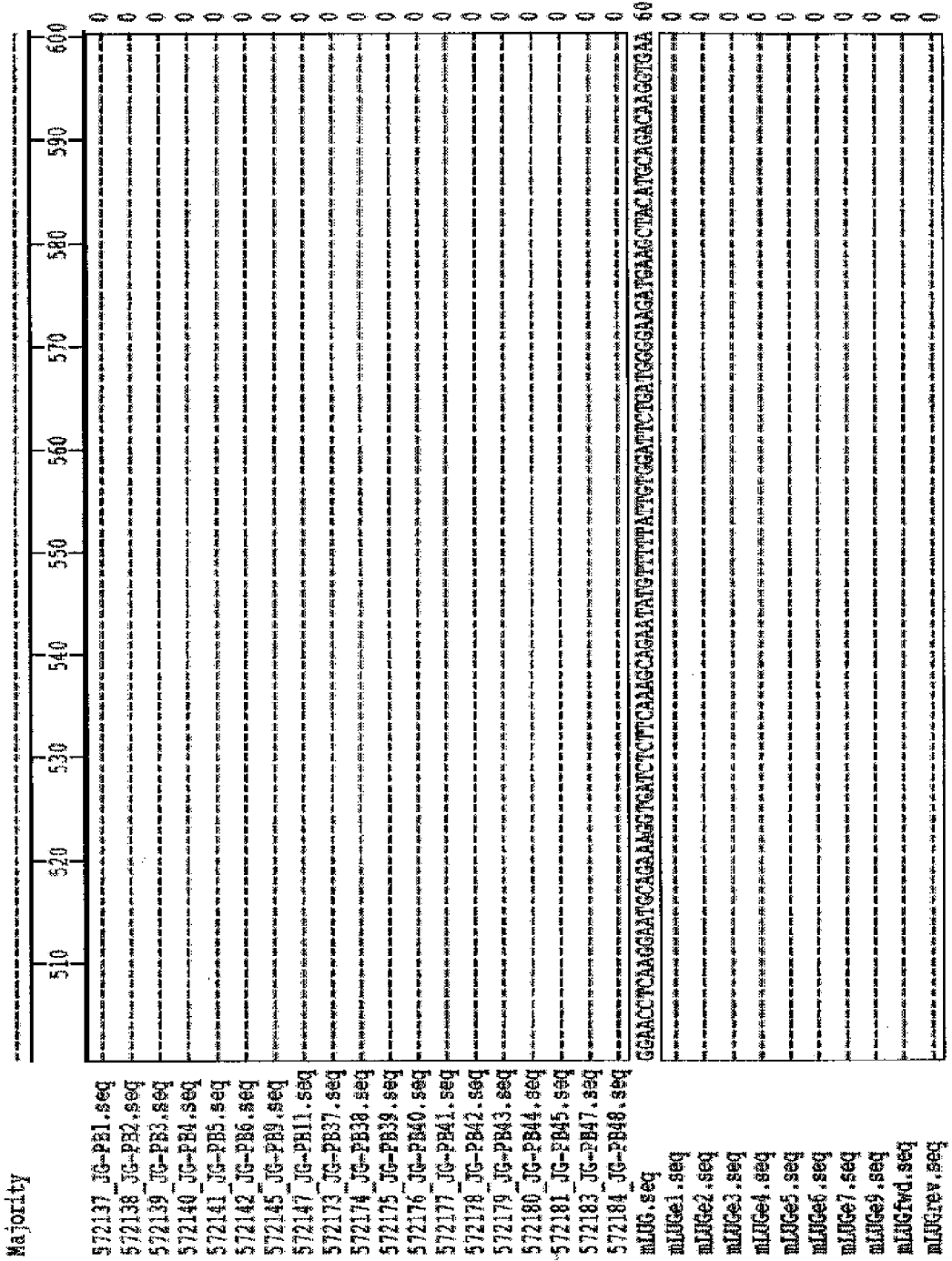
Figure 17:
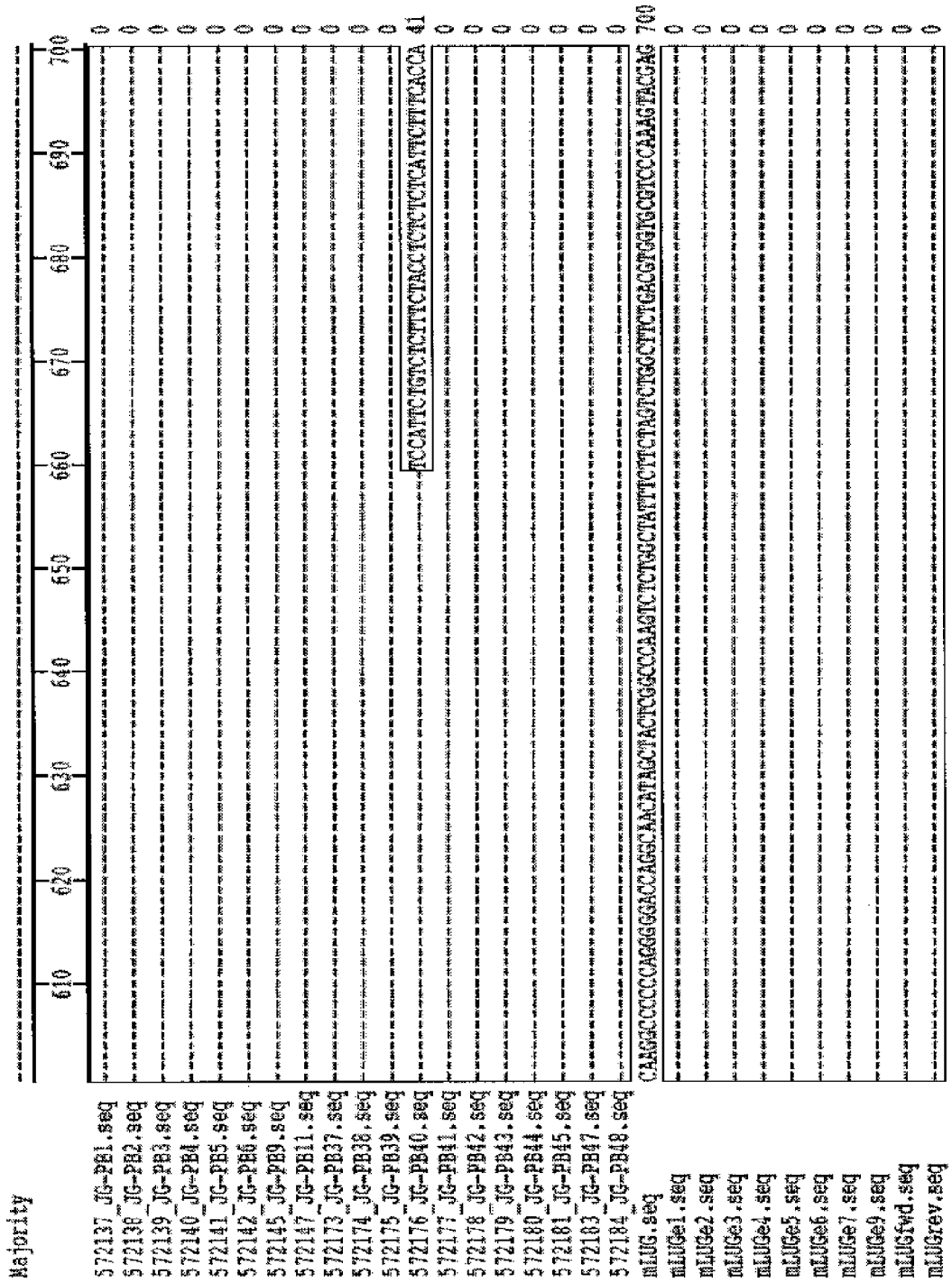
Figure 17:
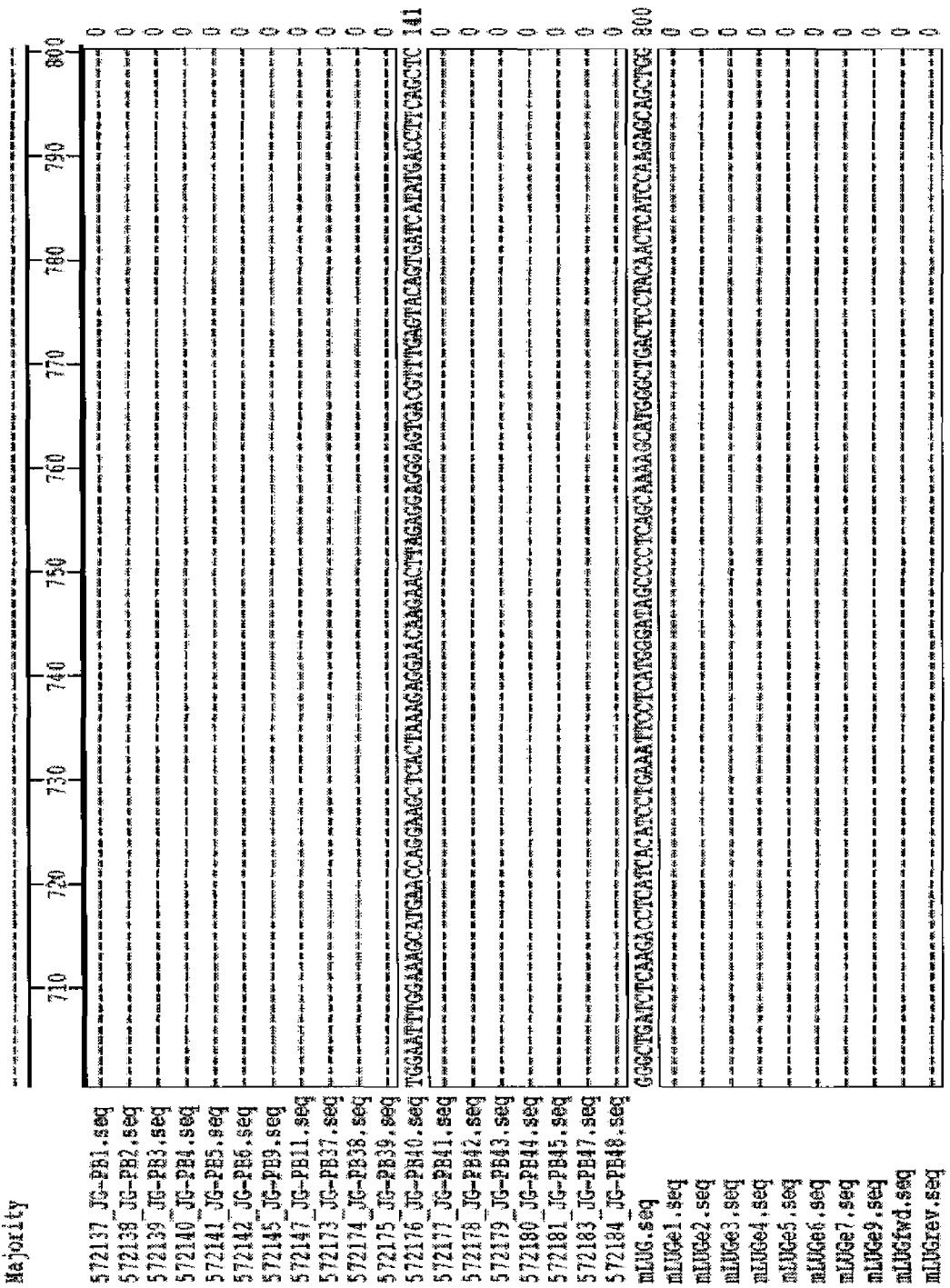
Figure 17:
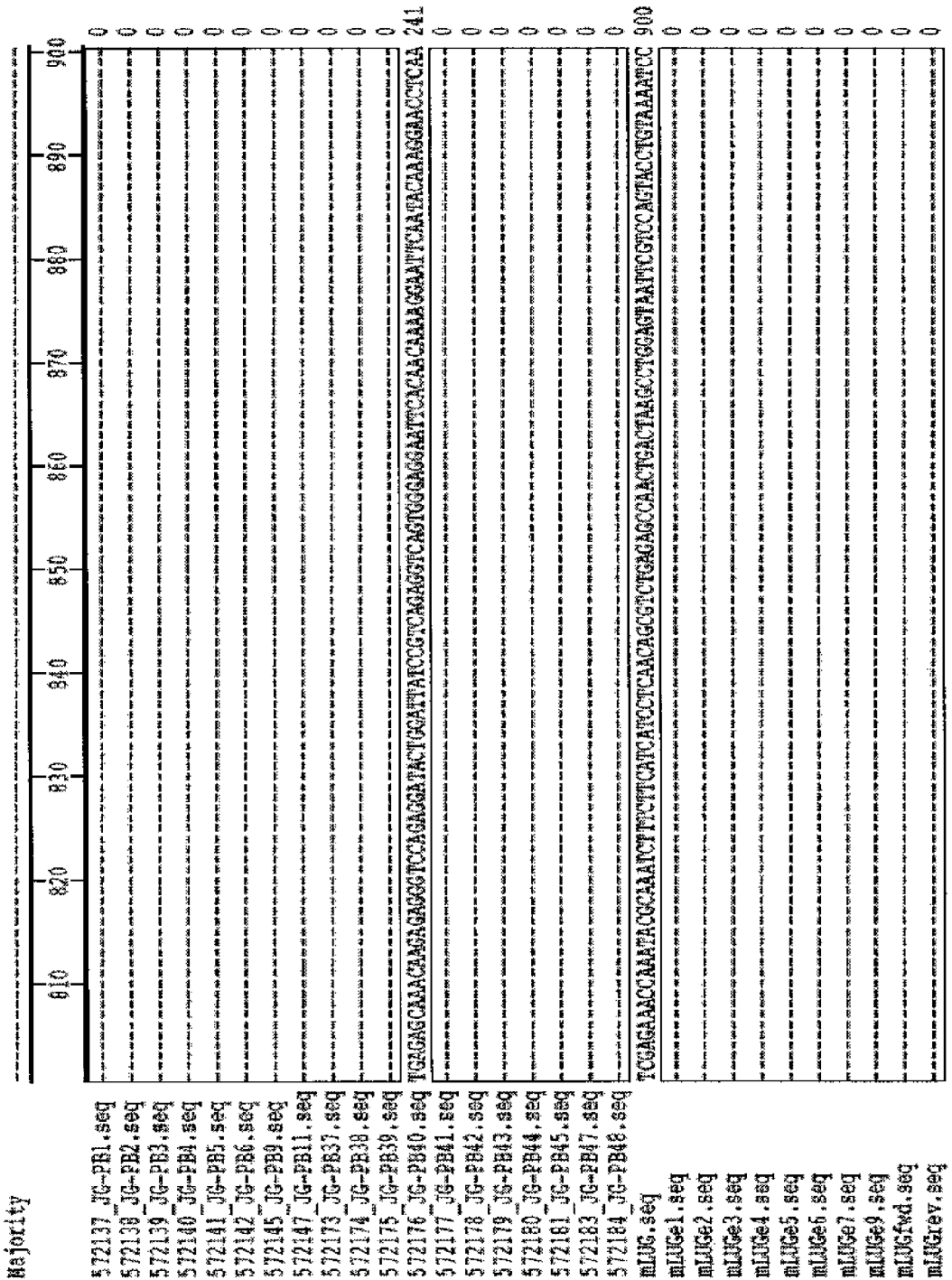
Figure 17:
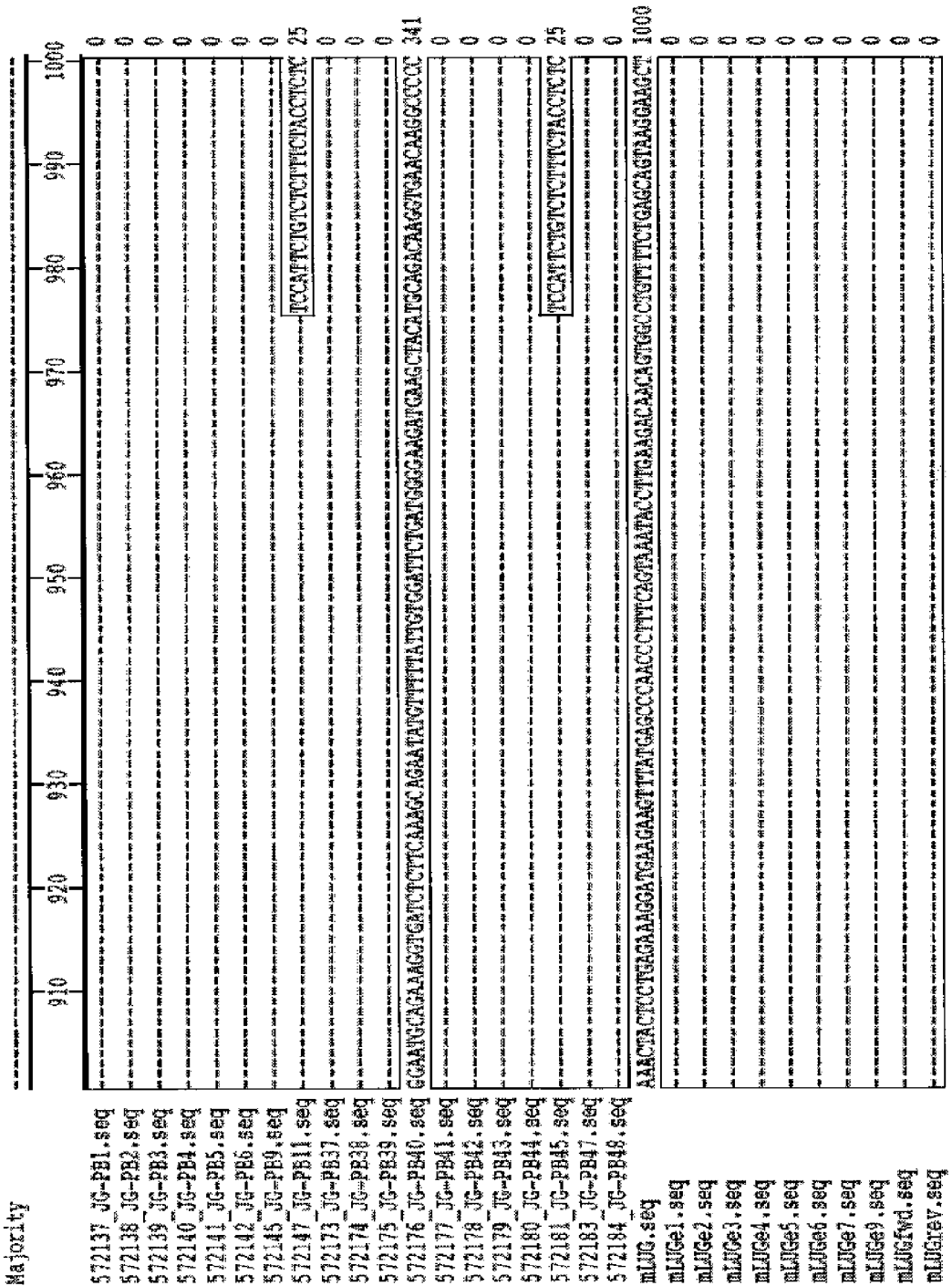
Figure 17:
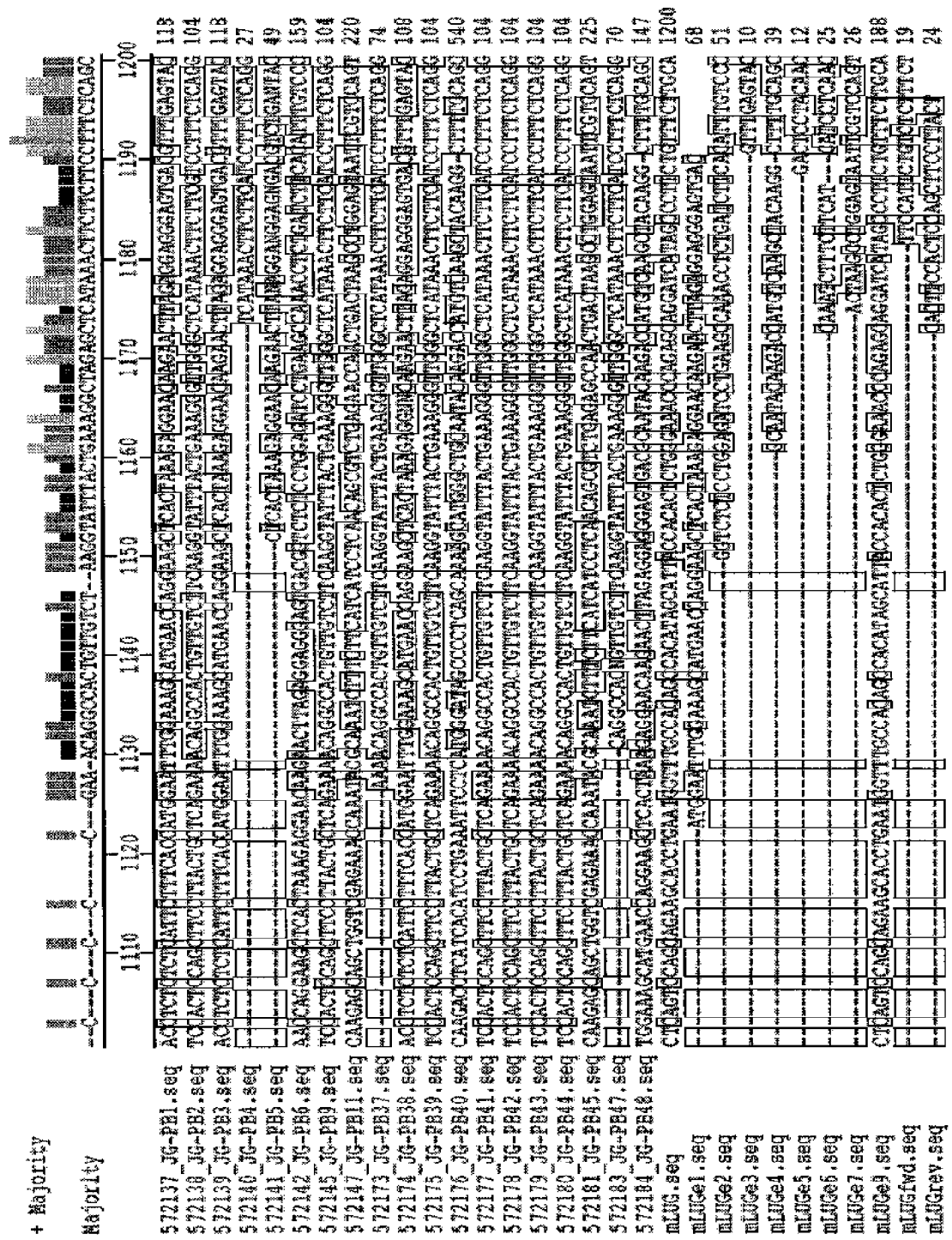
Figure 17:
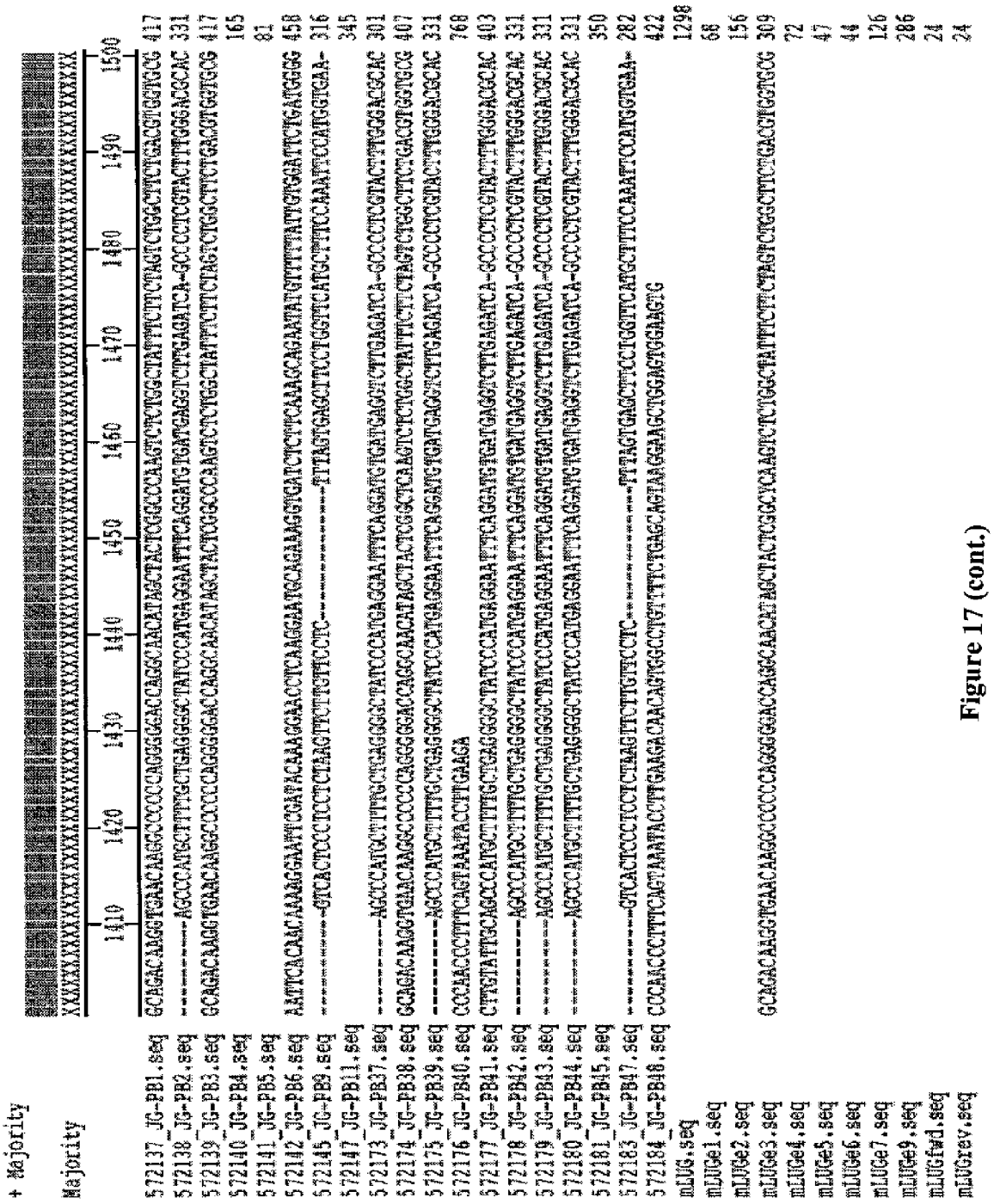
Figure 17:
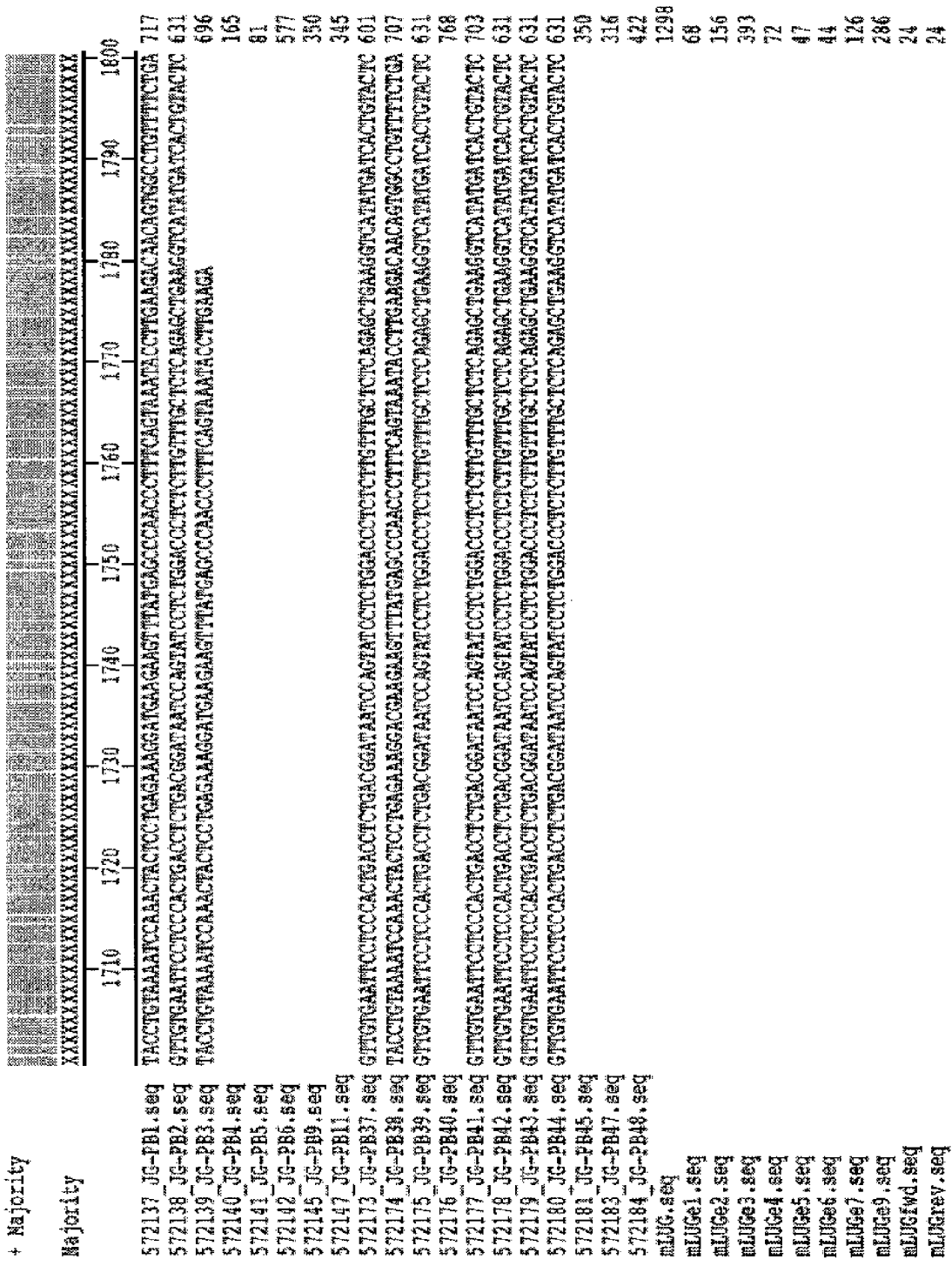
Figure 17:
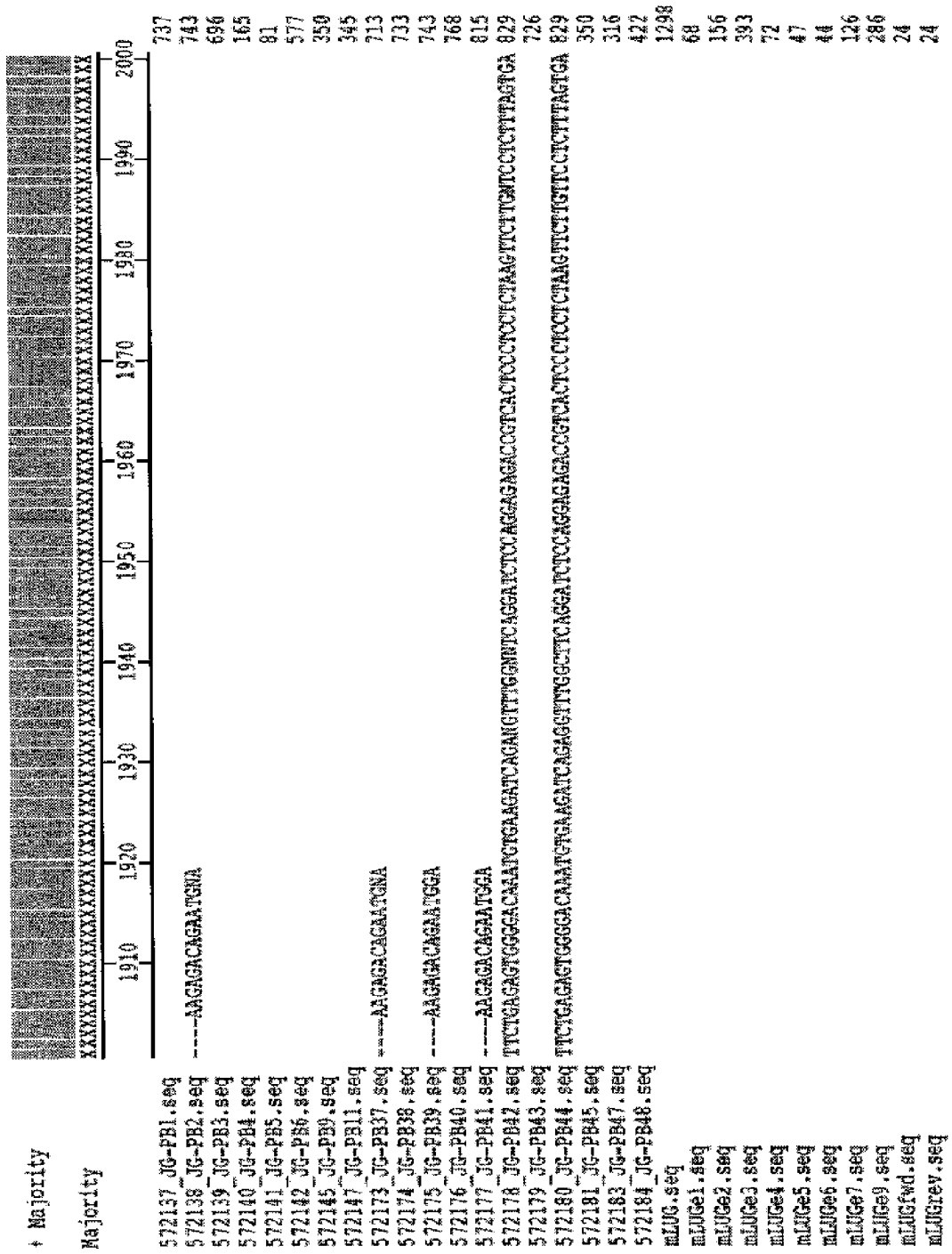
Figure 17:
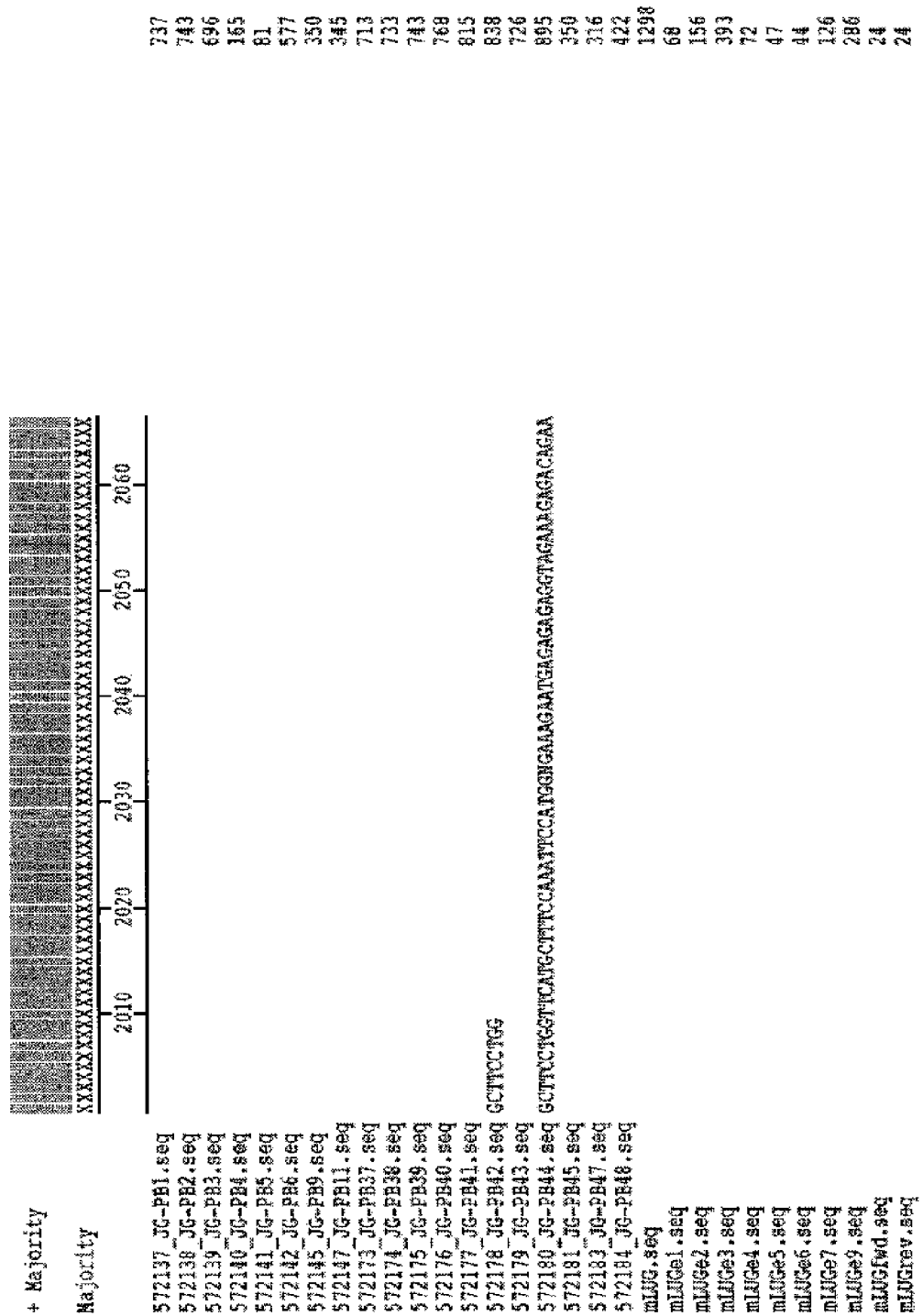

Alignments of the sequences are shown in FIGS. 14 to 17. FIG. 14 shows an amino acid sequence alignment of human MLIP proteins hMLIP-1, hMLIP-2, hMLIP-3, hMLIP-4 and hMLIP-5. The amino acid sequences were translated from the five different human MLIP nucleotide sequences cloned (SEQ ID NOs: 80 to 106) from a pooled human cDNA library. FIG. 15 shows an amino acid sequence alignment of mouse MLIP proteins mMLIP-01, mMLIP-02, mMLIP-03, mMLIP-04, mMLIP-05, mMLIP-06, mMLIP-07, mMLIP-08, mMLIP-09 and mMLIP-10. The amino acid sequences were translated from the ten different mouse MLIP nucleotide sequences cloned (SEQ ID NOs: 47 to 74) from a pooled mouse heart cDNA library. FIG. 16 shows a nucleotide sequence alignment of human MLIP nucleotide sequences cloned (SEQ ID NOs: 80 to 106) from a pooled human cDNA library. FIG. 17 shows a nucleotide sequence alignment of mouse MLIP nucleotide sequences cloned (SEQ ID NOs: 47 to 74) from a pooled mouse heart cDNA library.

The present invention also provides a method for detecting the presence or absence of a muscle lamin A/C interacting protein (MLIP) in a biological sample comprising the steps of: obtaining the biological sample from an animal, and providing a labelled antibody to MLIP to the sample, whereby presence or absence of the label indicates the presence or absence of the MLIP. The sequences can be detected using a kit according to another aspect of the present invention. For example, the present invention provides a kit for detecting the presence or absence of a muscle lamin A/C interacting protein (MLIP) in a biological sample, the kit comprising an antibody to MLIP and instructions for use. In another embodiment, the kit is for detecting the presence or absence of a nucleotide sequence encoding muscle lamin A/C interacting protein (MLIP) in a sample, the kit comprising one or more primers selected from the group consisting of SEQ ID NO: 17 to 46 and SEQ ID NOs: 93 to 94, together with instructions for use.

MLIP transgenic mice develop bradycardia with a prolonged P-R interval with abnormal myocardial morphology: Lamin A/C linked cardiomyopathies are known to develop cardiac conduction disease with dilation. Loss or mis-regulation of MLIP may contribute to alterations in cardiac development. Further, loss or mis-regulation of MLIP may contribute to the onset and development of dilated cardiomyopathy with conduction disease. To investigate this concept, four αMHC-MLIP transgenic mouse lines were generated. These mice possess the MLIP transgene driven by the αMHC promoter.

FIG. 1 shows relative MLIP RNA expression levels of the four αMHC-MLIP transgenic mouse lines with evidence of mild hypertrophy. FIG. 1a shows MLIP RNA concentrations from adult hearts of wildtype (WT, n=4) and each of the αMHC-MLIP transgenic mouse lines (n=2 per line) were determined by real-time PCR. All values were normalized to the mean concentration of MLIP RNA expression of wild-type control mice. FIG. 1b illustrates preliminary heart to body weight ratios which were determined for each of the established αMHC-MLIP transgenic mouse lines (*p<0.005 vs WT). These data established a 4 to 50-fold increase in MLIP RNA expression over wild-type control mice with a trend towards increased heart to body weight ratios at 5 weeks of age.

FIGS. 2a to 2c illustrate that MLIP transgenic mice develop bradycardia with a prolonged P-R interval. Representative electrocardiographic profiles of two αMHC-MLIP transgenic mouse lines and a control mouse are shown: FIG. 2a Line 39 (n=6), FIG. 2b Line 49 (n=4) and FIG. 2c control (n=8). Preliminary electrogardiographic studies of two of the βMHC-MLIP transgenic mouse lines reveal the progressive and significant appearance of both bradycardia with a prolonged P-R intervals in each of the lines.

FIG. 2d shows a significant reduction of heart rate (p<0.02) observed in both MLIP transgenic mouse lines compared to control mice. Further, FIG. 2e shows a significant increase (p<0.02) in the prolongation of the P-R interval of both MLIP transgenic mouse lines as compared to control mice.

FIGS. 3a to 3c show preliminary histological analysis of βMHC-MLIP transgenic mouse lines shows abnormal myocardial morphology. Five week old mouse hearts from a) wild-type and b-c) transgenic mice that over express the MLIP were fixed, sectioned and stained by H&E protocol.

To date, there has been no occurrence of sudden death or congestive heart failure phenotype with the oldest (16 weeks) transgenic mice.

Endogenous MLIP is localized to both the nucleus and cytosol of rat neonatal myocytes: Using an MLIP specific polyclonal antibody, the cellular localization of MLIP in rat neonatal cardiomyocytes was determined. As shown in FIG. 4a, endogenous MLIP appears to be localized in both the cytosol and nucleus. The cytosolic staining of MLIP is diffuse but may be associated with a cytosolic organelle. FIG. 4b shows that the nuclear staining MLIP is punctate in nature and suggests co-localization with PML bodies of the nucleus as well as the inner nuclear membrane where lamin A/C is found.

Endogenous MLIP is localized to mouse C2C12 cells and rat hippocampal glial and neuronal cells. As shown in FIG. 4c, C2C12 cells were co-stained with specific polyclonal antibodies for MLIP (green) and PML (red). FIG. 4d shows in situ MLIP in mouse brain (Allen Mouse Brain Institute) localized to the hippocampus and in FIG. 4e, endogenous MLIP (red) was localized to the nuclei (green) and cytosol of rat hippocampal neurons (map2, blue) and glial cells.

Within 12 hours of initiation of C2C12 differentiation there is an ~2.5-fold increase in MLIP mRNA expression that coincides with a transient Myf5 and MyoD up regulation, followed by an up regulation of myogenin and MLIP. FIG. 19a shows representative expression profiles for muscle specific genes, between 0 and 72 hours of differentiation. C2C12 cells transfected with pCDNA3.1-MLIP vector show that overexpression of MLIP results in subsequent up-regulation of MLIP, Pax7, MyoD and VGLL2 mRNA (FIG. 19b; ND=not detected). This appears to suggest that MLIP may regulate PAX7, a myogenic determinant during regenerative myogenesis.

MLIP interacts with rod 1 domain of lamin A/C: In vitro pull-down assays were performed using recombinant hexa-histidine-MLIP and GST-lamin-rod I to determine if the observed interaction between MLIP and the rod I domain of lamin A/C, as observed in the yeast-hybrid assay, is a direct or indirect interaction. FIG. 5 illustrates that MLIP directly interacts with the rod I domain of Lamin A/C. As shown in FIG. 5a, two major splice variants of MLIP were cloned from mouse heart. Exon 3 of MLIP is absent in the short form of MLIP. Both the full length MLIP (His$_6$-MLIP) and the short form of MLIP (His$_6$-MLIP(ΔExon3)) were sub-cloned in frame with an N-terminal hexa-histidine tag of a pET100 vector and recombinant MLIP was subsequently expressed in *E.coli*. FIG. 5b shows the isolation of bacterial-expressed His$_6$-MLIP and GST-Lamin recombinant proteins. Various combinations of His$_6$-MLIP and GST-Lamin recombinant proteins were mixed together (as indicated) and incubated at room temperature for 60 min in 10 mM Phosphate buffer (pH7.4), 50 mM NaCl, 0.05% triton X-100. Ni$^{2+}$-NTA sepharose beads were added to each reaction mixture (right panels) and complexes were isolated and washed by centrifugation in phosphate buffer (pH7.4), 50 mM NaCl, 0.05% triton X-100. Complexes were eluted by addition of SDS-PAGE loading buffer, boiled, and resolved by SDS-PAGE. Western analysis was performed using anti-GST (Cell Signaling) and anti-MLIP polyclonal antibodies. A 1:10 dilution of the total starting material was run on the same gel (left panels). Assay was repeated two additional times with similar results.

Heart-enriched expression of MLIP: FIGS. 6a to 6c show specific expression of MLIP in mouse and human. Distribution of MLIP expression by Northern analysis in a) mouse and b) human tissues revealed two transcripts. 10 ug of poly-A enriched RNA was loaded per lane. In FIG. 6c, normalized tissue distribution of MLIP expression in adult mouse was determined by real time PCR. MLIP expression profile by Northern analysis demonstrated that MLIP expression was primarily associated with the heart and brain in mouse and heart and skeletal muscle in human. Real-time PCR of MLIP RNA from various mouse tissues showed a similar distribution of MLIP expression with the heart having approximately 3 times more MLIP, with smooth muscle>skeletal muscle>heart (FIG. 6d).

Specific induction of MLIP expression during cardiomyogensis of P19 cells: Pluripotent P19 cells are a well established and extensively studied cell line that can be induced to differentiate neuronal/glial cells in the presence of retinoic acid, skeletal muscle cells (retinoic acid plus dimethyl sulfoxide (DMSO)), and cardiac muscle cells in the presence of DMSO.

FIGS. 7a to 7b show the specific induction of MLIP expression during P19 cardiomyogenesis. In FIG. 7a, P19 cell differentiate into cardiac cells in the presence of dimethyl sulfoxide (DMSO). In FIG. 7b, neuronal and glial cells in the presence of retinoic acid. MLIP expression during DMSO induced cardiomyogenesis of P19 cells increased dramatically at day 5 of DMSO induction and continued through day 9. The MLIP expression at day 5 was shown to be concurrent with a number of cardiac and striated muscle specific transcription factors such as GATA-4, MEF2C and Nkx2.5 [35]. This induction of MLIP expression by DMSO is specifically associated with cardiomyogensis of P19 cells since neuronal differentiated P19 cells did not express MLIP.

MLIP is expressed in a transient biphasic manner during the critical phase of the perinatal heart's exit from the cell cycle. FIG. 8a shows that shortly after birth, MLIP mRNA expression is up-regulated in the heart and peaks at 4 days post-birth followed by MLIP down-regulation by day 5. This transient expression of MLIP corresponds to the same period which the cardiomyocytes are exiting their last round of cell division with the absence of cytokinesis. The reactivation of MLIP after day 5 is associated with adult cardiomyocyte hypertrophic growth. Western blot analysis of endogenous MLIP through this period reveals a switch in LIP isoform distribution from a short MLIP form to a long MLIP form (FIG. 8b).

At least four alternative splice forms of MLIP have been identified through direct cloning or RACE analysis. FIG. 18 shows the results of direct cloning. In FIG. 18a, RT-PCR (left panel) was performed on mRNA isolated from mouse hearts using primers targeted to the 5'- and 3'-UTR of MLIP as defined by the EST database. The RT-PCR product was TA cloned into pCR-II plasmid and transformed into bacteria. Direct PCR was performed with primers targeting flanking regions of the MLIP insertion site amplified four different product sizes (right panel) with each PCR product sequenced. Based on these data, an alternative splice map of MLIP was constructed (FIG. 18b). It appears that the MLIP gene comprises 12 exons and is regulated by two putative promoters with exon 1a only observed in cDNA cloned from muscle and both exons 1a and 1b observed in cDNA cloned from brain.

Suppressed MLIP expression in the MYBPC3 mouse during the onset of DCM in the perinatal heart. Cardiac Myosin Binding Protein-C (MYBPC3) is a 1274 amino acid thick filament accessory protein component of the striated muscle sarcomere A band that constitutes 2% to 4% of the myofibril. Although there are four MYBPC3 genes in the human genome, only cardiac MYBPC3 is expressed in embryonic, neonatal, and adult hearts. MYBPC3 interacts with at least three sarcomere components: myosin heavy chain, actin, and titin. More than 30 cardiac MYBP3 gene mutations have been identified as causes of hypertrophic cardiomyopathy (HCM); an autosomal dominant disorder resulting from defective sarcomeres. The majority of cardiac MYBPC3 mutations are predicted to encode truncated proteins that lack portions of either the carboxyl myosin and/or titin binding domains. Mice that express mutant cardiac MYBPC3 to create murine HCM models have been produced. These mice, like humans bearing the same mutation, develop adult onset HCM. Homozygous mice that express two mutant alleles and no wild-type cardiac MYBPC3 develop LV dilation by 3 days of age and have all of the features of DCM, including LV chamber dilation with impaired fractional shortening.

Figure 9:
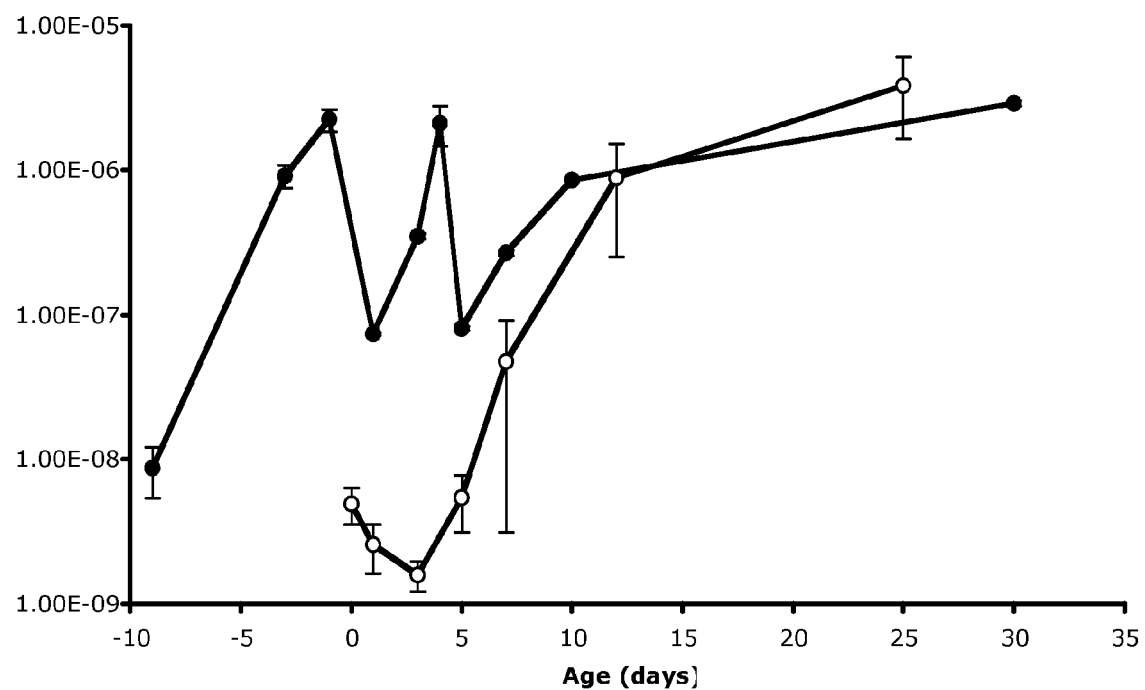
FIG. 9 shows an RT-PCR expression profile of MLIP for wild type hearts (closed circles) and MYBPC3 deficient hearts (open circles).

FIG. 9 shows a 30-fold reduction in MLIP mRNA expression as determined by real-time PCR, observed by 1 day post-birth in the MYBPC3 deficient mouse as compared to wild-type mouse. During the period of abnormal myocyte proliferation in the MYBPC3 deficient mice, MLIP expression remains suppressed and then by 10 days MLIP expression has returned to normal levels.

MLIP interaction with LMO7. MLIP was screened against a human heart library in the yeast two-hybrid assay. LMO7, an emerin-binding protein that regulates transcription of emerin and many other muscle relevant genes (Holaska et. al. 2006), was identified as interacting with MLIP, and was confirmed in the mammalian two-hybrid assay (FIGS. 20a and 20b). Disrupting the LIP-LMNA interaction and/or the regulation of MLIP expression may result in a gain of function.

MLIP knock-out mice In another aspect of the present invention there is provided an MLIP knock-out mouse. Targeted disruption of MLIP in knock-out mice (such as by insertion of LacZ cDNA) may result in alterations of the following as compared to wild-type mice:

a) echocardiographic and electrocardiograpic (ECG) output;

b) histology, particularly in the hearts of genetically modified mice at a variety of key developmental stages. Heart sections likely demonstrate alterations/aberrations in myocardium morphology (H&E stain) and fibrosis (Masson Trichrome).

c) RNA and protein analysis will typically indicate the expression of classic markers for cardiomyopathies (ANF, BNP and βMHC). Expression profiling can be achieved by any method known in the art, such as Northern and Western blotting (for RNA and protein), or Southern blots or DNA chip analysis (for DNA analysis).

d) MLIP expression analysis—MLIP expression in the developing mouse embryo can be mapped by utilizing a MLIP specific polyclonal antibody which has been generated. These can be confirmed by the nlsLacZ expression in the MLIP-knockout mice. Embryos can be stained for LacZ expression and then sectioned to identify and confirm the tissue expression profile of MLIP.

The knock-out mice of the present may be generated using any known protocol. However, certain modifications may be envisioned by the person of ordinary skill in the art in the context of the present invention with respect to the expression of MLIP. One example of the knock-out mouse protocol is provided herein. The lacZ gene is fused to a nuclear localization signal sequence (nlslacZ) so as to increase the signal to noise ratio of lacZ detection. To generate the MLIP-nlslacZ targeting vector, a fragment containing at least exons 1 and 2 of the MLIP locus is isolated by screening a 129 mouse genomic library (Stratagene) using the total coding region of the mouse MLIP cDNA as a probe. The identified fragment is inserted into the multiple cloning site of pBluescript KS+. An ATG start codon in exon 1 is PCR-modified into an NcoI site, and a BspHI-XhoI nlslacZ cassette is ligated in-frame with exon 1 in between the NcoI and SalI sites. This subclone is flanked on the 3' end with the PGK-hygromycin cassette, thereby deleting the coding sequence in exon 2. The Polyoma thymidine kinase gene obtained from a previously described vector [36] is added 3' of the construct. Embryonic stem (ES) cells, such as those from the 129/Sv mouse line, for example, are transfected with the construct, and homologous recombinants screened by Southern analysis. ES cells with a homologous recombination are then injected into C57Bl/6J blastocysts to generate heterozygous MLIP-nlslacZ mice. The mice are genotyped and separated into wild-type or heterozygous mice by Southern blot analysis and PCR based genotyping. Chimeric males are crossed to 129/SeEv females and germ-line transmission of the injected ES cell lines are monitored by detecting agouti mice among the F1 offspring and subsequent Southern blotting. Heterozygote mice are crossed to generate a homozygote null MLIP mouse. The colony can be expanded to provide sufficient mice for characterization.

Characterization MLIP mouse models: Mouse models generated can be initially characterized by the following protocols:

Immunocytochemistry: Cultured cells transiently expressing MLIP were plated on gelatin-coated coverslips. Cells are fixed with 4% paraformaldehyde in PBS on ice for 20 min, followed by three washes of PBS. The fixed cells are then blocked with 10% normal serum in PBS on ice for 60 min followed by a single wash in PBS. The cells will then be incubated in the appropriate primary anti-sera in 1.5% normal serum for 1-2 hours, washed three times in PBS, and then incubated for 60 min with the appropriate secondary anti sera conjugated to a flourophore (Molecular Probes) with 1.5% normal serum. Coverslips are then washed three times in PBS, mounted on glass slides, and analysed with a confocal microscope.

Northern analysis: Initially, total mouse RNA is isolated from heart, skeletal muscle, brain, liver and kidney at variety of developmental time points (E9.5 through E14.5, 1 day, 14 day and 8 weeks) using TRIzol reagent (Invitrogen). At least 10 µg of total RNA per lane is loaded on a 1% agarose gel (containing 0.42% MOPS, 5 mM sodium acetate, 0.7 mM EDTA, and 0.6% formaldehyde). Electrophoresis is performed in 1×MOPS buffer (0.42% MOPS, 5 mM sodium acetate, 0.7 mM EDTA) with a circulating pump at 40-60 constant volts for about 2-3 hours. The electrophoresis is stopped when the stop dye has migrated about ⅔-¾ of the way through the gel. The RNA is then transferred overnight to a nylon membrane (pre-wet in 1×MOPS buffer) with a 10×SSPE stock solution (1.5 M NaCl, 0.1 M $NaH_2PO_4$, 10 mM EDTA, pH 7.0). The membrane is then be re-hybridized at 42° C. in 50% deionized formamide, 5×SSPE, 50 mM sodium phosphate buffer, pH 6.8, 1× Denhardt's solution, heat denatured salmon sperm DNA to 100-200 µg/ml, and 0.5% SDS for 3-4 hours. Hybridization occurs overnight with a radiolabelled probe at 42° C. in fresh prehybridization buffer with 7.5% dextran sulfate. 25 ng of a DNA probe is labelled with random primers, with MLIP cDNA fragment used as template. The next day, the membranes are washed twice in 2×SSPE, 0.1% SDS at room temperature, 10 minutes per wash, then for 30 minutes in 0.5× or 0.2×SSPE, 0.1% SDS at room temperature. The membrane is then be checked for radioactivity with a hand-held monitor and/or autoradiography before increasing the stringency. Initially, the membrane can be analysed by a phospho-imager and then exposed overnight against film.

RT-PCR and real time RT-PCR: cDNA is synthesized from total RNA samples (isolated for Northern analysis) by oligo (dT)-primed reverse transcription (Protoscript First Strand cDNA synthesis, New England Biolabs). To characterize MLIP expression in the heart through development, cDNA is subjected to either PCR amplification using HotStarTaq DNA polymerase (Qiagen) or real time quantitative PCR (qPCR). Primers are designed for the specific amplification of MLIP splice isoforms, such that the PCR product length will be 200 to 300 base pairs in length and overlap splice form specific exon boundaries.

To determine the relative abundance of MLIP isoforms in mouse tissue, qPCR is performed with SYBR green PCR master mix (Roche) using LightCycler 1.0 sequence detection system (Roche). Isoform-specific primers for MLIP [MLIP67 primers, 5'-TTCATCATCCTCAACAGCGT-3' (forward) (SEQ ID No: 107), 5'-GGGTTGGGCTCAT-AAACTTC-3' (reverse) (SEQ ID No: 108)] and [MLIP3 primers, 5'-TAGCTACTCGGCCCAAGTCT-3' (forward) (SEQ ID No: 109), 5'-ATCCCATGAGGAATTTCAGG-3' (reverse) (SEQ ID No: 110)] are used to analyze transcript abundance with mouse GAPDH transcript levels [GAPDH primers, 5'-GCAACAGGGTGGTGGACCT-3' (forward) (SEQ ID No: 111), 5'-GCAACAGGGTGGTGGACCT-3' (reverse) (SEQ ID No: 112)] serving as an internal control to compensate for differences in RNA recovery and used to normalize the values of transcript abundance of MLIP isoforms. All PCR reactions, cycled 40 times by a two-step cycle procedure (denaturation 95° C., 15s; annealing 65° C., 1 min) after the initial stages (50° C., 1s; 95° C. 10 min), can be performed in triplicate for each gene. To generate a standard curve, serially diluted heart cDNA is included in the 96-well plate along with cDNA from the various tissues.

In situ hybridization studies. Studies have been described previously [37]. A typical study which may be performed in the context of the present invention is briefly outlined herein. Eight week, 2 week, and newborn mice and E9.5 to E14.5 embryos are dissected free from the uterine muscle and studied. E0.5 is defined as noon on the day postcoitous when a vaginal plug is detected. Embryos are removed, washed in phosphate buffered saline (PBS), fixed overnight in 4% paraformaldhyde in PBS and either frozen (−20° C., 100% methanol) or kept in 70% ethanol at room temperature prior to paraffin embedding and histological analysis. Embedded sections are stained with hematoxylin and eosin or used for in situ hybridization as previously described[38]. Plasmids containing MLIP sequences are used as template for digoigenin (DIG) riboprobes, which are produced according to the manufacture's specifications (Roche). DIG-RNA probes are hybridized overnight at 70° C. and incubated with anti-DIG-AP fragment, and signal detected using Nitro Blue Tetrazolium and 5-bromo-4-chloro-3-indolyl-☐-D-galactopyranoside substrates (Roche)[39].

Electrocardiographic and Echocardiographic Analysis: Surface electrocardiograms can be obtained from anesthetized mice at 2 weeks, 2 months and 4 months of age. Subcutaneous electrodes are inserted in four configurations to obtain 4 electrocardiographic recordings: Lead 1 (right and left forelimb), Lead 2 (left forelimb and right hindlimb), Lead 3 (right forelimb and left hindlimb) and transthoracic (beneath skin of back and skin of chest at cardiac apex). After ECG monitoring, mice are then euthanized by harvesting the heart for biochemical analysis. To monitor the occurrence and frequency of supraventricular arrhythmias, telemetry electrocardiography is obtained using subcutaneous implantation of a radio-transducer and subcutaneous transthoracic electrodes). Devices are implanted under general anaesthesia in mice at 16 weeks of age, mice are allowed to recover for 1 week and are then monitored continuously for 24 hours. Mice are then euthanized and the heart is harvested for biochemical analysis. Mice are not kept with telemetry monitors longer than 3 weeks. To ascertain cardiac diastolic function it was necessary to measure intracardiac pressure/volume loops and diastolic pressures during the normal cardiac cycle in vivo. Intracardiac conductance catheters allow the accurate measurement of these parameters in the mouse heart. Pressure/volume loop measurements are obtained in anesthetized mice at 16 weeks of age by inserting a 1.4 French microcatheter down the carotid artery. This closed-chest preparation is minimally invasive and does not require mechanical ventilation. Echocardiography was performed with an Hewlett Packard Sonos™ 4500 ultrasound machine and a 6-15 MHz linear array transducer on anesthetized mice with a heart rate greater than 450 bpm, as previously described [40].

Characterization of the regulation of MLIP function and expression in the heart during development and the onset of DCM-CCD.

This study tests the hypothesis that differential regulation of MLIP isoform expression is necessary for normal differentiation of cardiomyocytes. Expression in cultured cardiomyocytes of deleted and mutated reporter constructs of the MLIP promoter is analyzed to identify regulatory sequences and transcription factors that control MLIP mRNA levels. Temporal and spatial analysis of endogenous MLIP expression is characterized at different developmental time points of heart development using a variety of molecular methods: Northern, RT-PCR, real-time PCR, in situ hybridization and Western analysis. The investigation of just the levels of MLIP expression is not sufficient alone and the expression of each splice variant of MLIP needs to be taken into context as this can provide important information as to the function of MLIP.

Temporal and tissue specific expression of MLIP in the mouse: Specific tissue expression of total MLIP during mouse development can be investigated. The primary source of tissue is obtained from wild-type, in-bred 129/SeEv mice. The basis for this choice of mouse strain is that many of the genetically modified mouse models are generated in the 129/SeEv background. Total mouse RNA and protein are isolated from heart, skeletal muscle, brain, liver and kidney at a variety of developmental time points (E9.5 through E14.5, 1 day, 14 day and 8-12 weeks post birth) to be analyzed by northern analysis, real time PCR and Western blot. Once an MLIP expression profile is mapped throughout normal mouse development, a variety of published mouse models for DCM-CCD can be examined. These include mice carrying lamin missense mutations H222P[14] and N195K[41] and a lamin null allele [33]. Spatial expression can be elucidated by in situ hybridization and immunohistochemical studies of whole embryos (<E12.5) and tissue sections as described in general methods that would be known in the art.

Figure 10:
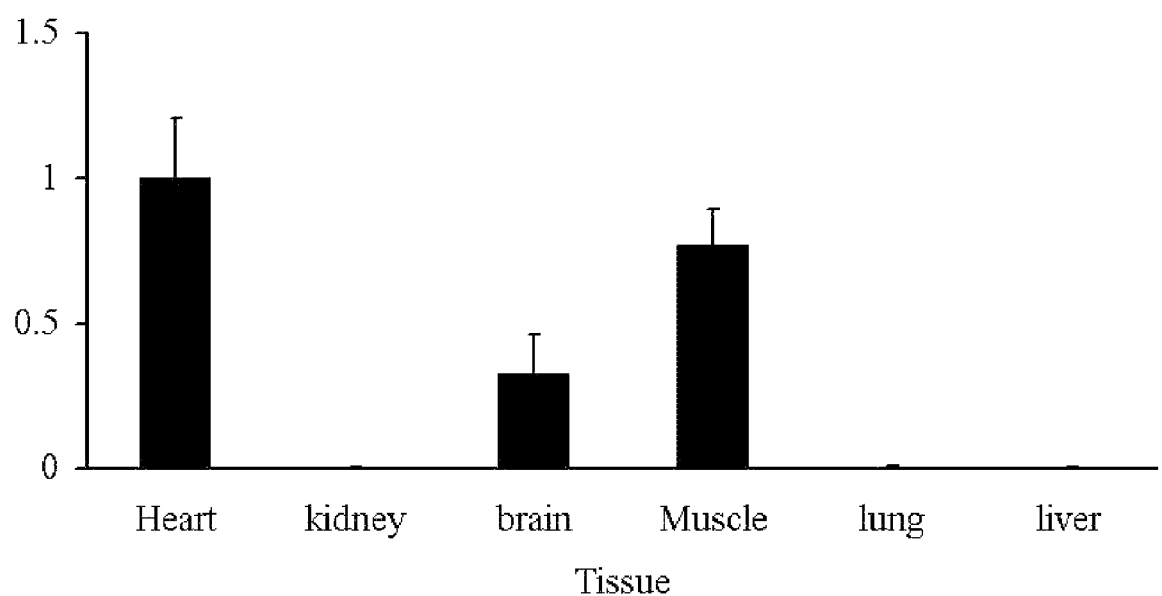
FIG. 10 shows relative adult tissue specific expression of MLIP as determined by qualitative RT-PCR.
Figure 11:
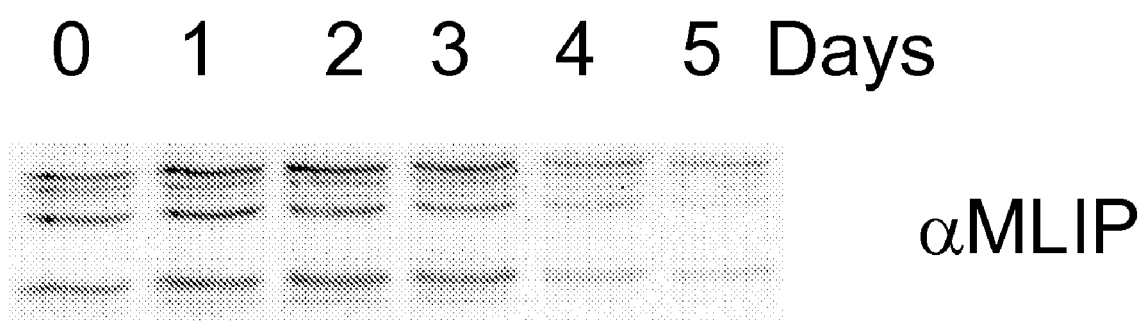
FIG. 11 shows a Northern blot of MLIP expression in C2C12 cells during myotube formation.

FIG. 10 shows relative adult tissue specific expression of MLIP as determined by qualitative RT-PCR. FIG. 11 shows a Northern blot of MLIP expression in C2C12 cells during myotube formation. FIG. 12 shows MLIP expression in C2C12 cells during myotube formation by indirect immunoflorescence staining with a MLIP specific antibody.

Figure 13:
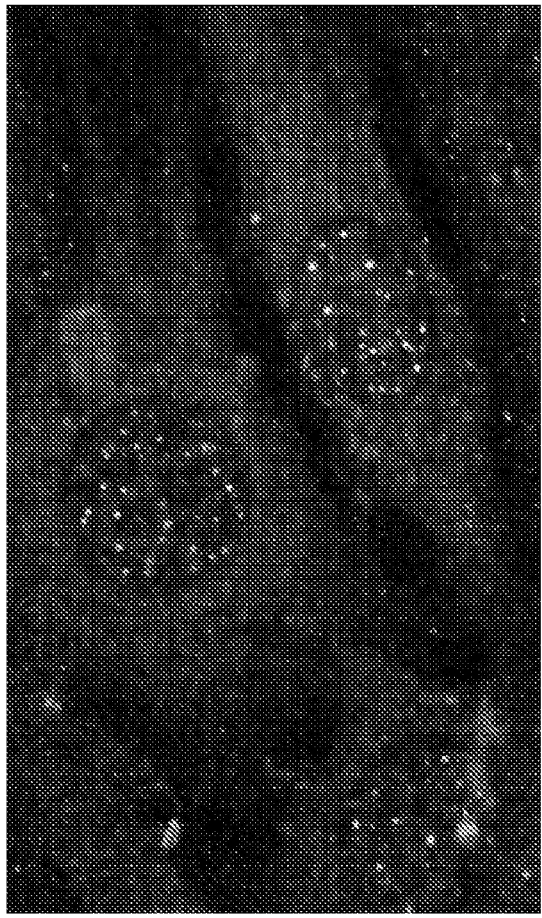
FIG. 13 shows MLIP co-localized with PML bodies in C2C12 cells by indirect immunoflorescence staining with a MLIP and PML specific antibodies.

FIG. 13 shows MLIP co-localized with PML bodies in C2C12 cells by indirect immunoflorescence staining with a MLIP and PML specific antibodies.

Chromatin Immunoprecipitation (ChIP) Analysis

A ChIP analysis was performed (SimpleChIP™ Enzymatic Chromatin IP Kit, Product Catalog Number 9002 and 9003, Cell Signaling Technology, Danvers, Mass., USA). C2C12 mouse myoblasts and both MLIP antibodies described herein were used. MLIP immunoprecipitated chromatin fragments were purified and PCR linkered/amplified. Following TA cloning and sequencing, 80 positive clones were identified and the genomic location of each of these fragments was determined.

TABLE 1

Genes that may be regulated by MLIP as determined by chromatin immunoprecipitation

| GENE | CELLULAR ROLE |
| --- | --- |
| Notch2 | Development, Differentiation, Commitment Death, Apoptosis, Proliferation, Survival, growth |
| CREM(ICER) | Death, Apoptosis, Proliferation, Growth |
| Sox5 | Development, Commitment, Apoptosis |
| KIF5C | Biogenesis, Growth |
| PLCB1 | Apoptosis, Proliferation, Growth |
| MET | Apoptosis, Proliferation, Growth |
| MMP3 | Differentiation, Proliferation, Survival |
| RUNX1 | Development, Differentiation, Death, Apoptosis, Proliferation, Growth |
| Akt2 | Differentiation, Cell Cycle Progression, Death, Apoptosis, Proliferation, Survival, Growth |
| NEK7 | — |
| FLI1 | Differentiation, Apoptosis, Proliferation, Growth |
| PP2R3A | Cell Cycle Progression, Survival |
| GATA6 | Differentiation, Apoptosis, Survival |

Interestingly, in relation to the defined cellular role of A-type Lamins (LMNA) all the above genes share at least one of the following roles in the cell: differentiation, cell cycle progression, biogenesis and apoptosis.

MLIP alternative splice variant regulation and expression in both the normal mouse and mouse models for DCM-CCD. The expression of individual MLIP splice variants within the mouse heart at a variety of developmental time points (E9.5 through E14.5, 1 day, 14 day and 8-12 weeks post birth) for both normal and mouse models for DCM-CCD can be determined by real-time PCR. cDNA is synthesized from total RNA samples and subjected to real-time PCR. Primers have been designed and characterized for the specific amplification of each MLIP splice isoform with GAPDH as a normalization control between samples and dilutions. The quality of qPCR amplification is typically assessed by gel electrophoresis, as described in general methods known in the art.

MLIP promoter analysis. Examination of the 5'UTR of both mouse and human MLIP reveals a very high degree of homology. Deleted and mutated reporter constructs of the MLIP promoter are analyzed to identify regulatory sequences and transcription factors that control MLIP mRNA levels. A preliminary examination of the 5' promoter region of the MLIP allele reveals several putative Tbx5, TEF-1, and Nkx 2.5 binding domains. To determine the minimal promoter region required for normal MLIP mRNA expression, a series of deletion constructs of the MLIP 5'UTR are generated and transiently transfected into cultured myocytes. Once the minimal MLIP 5'UTR is defined, putative muscle specific transcription factor binding domains can be mutated to determine their contribution to the regulation of MLIP expression. Once the important promoter elements have been mapped, site-directed mutagenesis is performed to test the effect of naturally occurring polymorphisms within the important regulatory sequences on the basal response of the MLIP promoter.

Plasmids and constructs: The putative promoter fragment for both human and mouse MLIP is obtained and sub-cloned into the pGL3-basic luciferase vector. A luciferase/MLIP 3'UTR chimeric construct in the pGL3-control vector that carries the SV40 enhancer and promoter and drives high levels of luciferase expression in cardiac myocytes is produced. Serial deletions and site-directed mutagenesis is performed following well-established protocols known in the art.

The MLIP specific antibody and genetically modified mice provide important reagents to characterize the biological role of MLIP. The regulation of MLIP function within the heart during normal development can be defined using these tools. In addition to defining the role of MLIP's function(s) in cardiomyocytes, the tools provide a powerful means for furthering the understanding the underlying mechanisms of cardiac specific laminopathies of DCM-CCD. As one possible embodiment of the present invention, expression of MLIP isoforms may be differentially regulated during specific developmental time points and the pathogenesis of DCM-CCD in mice. This may in turn effect sub-cellular localization of MLIP and consequently its function(s). Further, mis-expression of MLIP or loss of MLIP function can be found to result in altered cardiac structure and/or function in the mouse, based on the phenotypes generated by the genetically modified mice.

The spatial and temporal aspects of MLIP/Lamin interactions in real time in living cells can be determined using techniques known in the art, such as fluorescence resonance energy transfer (FRET) in living cells to measure real time flux of MLIP bound to Lamin A/C in response to stimuli. This may also provide a role of MLIP bound to Lamin A/C in cardiomyocyte physiology and the pathogenesis of Lamin associated DCM, as well as identifying the upstream signals involved in MLIP regulation, particularly in the roles of different heart specific transcription factors (Nkx 2.5 and Tbx5) on MLIP expression. Identification of specific MLIP interactors (other than Lamin A/C) can form the basis of defining the molecular mechanism of MLIP in the heart.

Loss or mis-regulation of MLIP may contribute to alterations in cardiac development. Further, loss or mis-regulation of MLIP may contribute to the onset and development of dilated cardiomyopathy with conduction disease. This is suggested by data obtained from investigating the effects of altered gene expression of MLIP in murine models as described herein. Preliminary investigation suggests that MLIP may be associated with the simultaneous development of both Dunnigans-type familial partial lipodystrophy (non-striated muscle laminopathy) and dilated cardiomyopathy, but the numbers reported are too low to be certain of their significance [31]. The finding of expression in brain tissue may indicate that MLIP could be involved in brain development, maintenance and/or pathology.

MLIP may also be involved in cardiomyocyte regeneration or in therapeutic development. For example, modulation of MLIP activity, either at the level of the gene or protein, may contribute to regulate cardiomyocyte or muscle differentiation. This can be important in regenerating heart or muscle tissue, which may be damaged from certain insults, such as infarct or the like. Certainly, within the context of the present invention, it is contemplated that MLIP may serve as a target for pharmaceutical agents.

The above-described embodiments of the present invention are intended to be examples only. Alterations, modifications and variations may be effected to the particular embodiments by those of skill in the art without departing from the scope of the invention, which is defined solely by the claims appended hereto. All documents referred to herein are incorporated by reference.

REFERENCES

2. Somech, R., et al., *Nuclear envelopathies—raising the nuclear veil.* Pediatr Res, 2005. 57(5 Pt 2): p. 8R-15R.
7. Ostlund, C., et al., *Intracellular trafficking of emerin, the Emery-Dreifuss muscular dystrophy protein.* J Cell Sci, 1999.112 (Pt 11): p. 1709-19.
8. Charniot, J. C., et al., *Functional consequences of an LMNA mutation associated with a new cardiac and non-cardiac phenotype.* Hum Mutat, 2003. 21(5): p. 473-81.
9. Muchir, A., et al., *Identification of mutations in the gene encoding lamins A/C in autosomal dominant limb girdle muscular dystrophy with atrioventricular conduction disturbances (LGMD1B).* Hum Mol Genet, 2000. 9(9): p. 1453-9.
10. Taylor, M. R., et al., *Natural history of dilated cardiomyopathy due to lamin A/C gene mutations.* J Am Coll Cardiol, 2003. 41(5): p. 771-80.
11. Bonne, G., et al., *Clinical and molecular genetic spectrum of autosomal dominant Emery-Dreifuss muscular dystrophy due to mutations of the lamin A/C gene.* Ann Neurol, 2000. 48(2): p. 170-80.
12. Brodsky, G. L., et al., *Lamin A/C gene mutation associated with dilated cardiomyopathy with variable skeletal muscle involvement.* Circulation, 2000. 101(5): p. 473-6.
13. Hegele, R., *LMNA mutation position predicts organ system involvement in laminopathies.* Clin Genet, 2005. 68(1): p. 31-4.
14. Arimura, T., et al., *Mouse model carrying H222P-Lmna mutation develops muscular dystrophy and dilated cardiomyopathy similar to human striated muscle laminopathies.* Hum Mol Genet, 2005. 14(1): p. 155-69.
17. Kitaguchi, T., et al., *A missense mutation in the exon 8 of lamin A/C gene in a Japanese case of autosomal dominant limb-girdle muscular dystrophy and cardiac conduction block.* Neuromuscul Disord, 2001. 11(6-7): p. 542-6.
19. Hong, J. S., et al., *Cardiac dysrhythmias, cardiomyopathy and muscular dystrophy in patients with Emery-Dreifuss muscular dystrophy and limb-girdle muscular dystrophy type 1B.* J Korean Med Sci, 2005. 20(2): p. 283-90.
20. van der Kooi, A. J., et al., *A newly recognized autosomal dominant limb girdle muscular dystrophy with cardiac involvement.* Ann Neurol, 1996. 39(5): p. 636-42.
22. Arbustini, E., et al., *Autosomal dominant dilated cardiomyopathy with atrioventricular block: a lamin A/C defect-related disease.* J Am Coll Cardiol, 2002. 39(6): p. 981-90.
23. Brown, C. A., et al., *Novel and recurrent mutations in lamin A/C in patients with Emery-Dreifuss muscular dystrophy.* Am J Med Genet, 2001. 102(4): p. 359-67.
24. Fatkin, D., et al., *Missense mutations in the rod domain of the lamin A/C gene as causes of dilated cardiomyopathy and conduction-system disease.* N Engl J Med, 1999. 341 (23): p. 1715-24.
25. Otomo, J., et al., *Electrophysiological and histopathological characteristics of progressive atrioventricular block accompanied by familial dilated cardiomyopathy caused by a novel mutation of lamin A/C gene.* J Cardiovasc Electrophysiol, 2005. 16(2): p. 137-45.
26. Pethig, K., et al., *LMNA mutations in cardiac transplant recipients.* Cardiology, 2005. 103(2): p. 57-62.
27. Sebillon, P., et al., *Expanding the phenotype of LMNA mutations in dilated cardiomyopathy and functional consequences of these mutations.* J Med Genet, 2003. 40(8): p. 560-7.
28. Emery, A. E., *Emery-Dreifuss syndrome.* J Med Genet, 1989. 26(10): p. 637-41.

29. Jakobs, P. M., et al., *Novel lamin A/C mutations in two families with dilated cardiomyopathy and conduction system disease.* J Card Fail, 2001. 7(3): p. 249-56.
30. Funakoshi, M., Y. Tsuchiya, and K. Arahata, *Emerin and cardiomyopathy in Emery-Dreifuss muscular dystrophy.* Neuromuscul Disord, 1999. 9(2): p. 108-14.
33. Sullivan, T., et al., *Loss of A-type lamin expression compromises nuclear envelope integrity leading to muscular dystrophy.* J Cell Biol, 1999. 147(5): p. 913-20.
34. Cockell, M. and S. M. Gasser, *Nuclear compartments and gene regulation.* Curr Opin Genet Dev, 1999. 9(2): p. 199-205.
35. Gianakopoulos, P. J. and I. S. Skerjanc, *Hedgehog signaling induces cardiomyogenesis in P19 cells.* J Biol Chem, 2005. 280(22): p. 21022-8.
36. Pandolfi, P. P., et al., *Targeted disruption of the GATA3 gene causes severe abnormalities in the nervous system and in fetal liver haematopoiesis.* Nat Genet, 1995.11 (1): p. 40-4.
38. Ausubel, F., et al., *Current Protocols in Molecular Biology.* 2004: John Wiley & Sons, Inc., New York, N.Y.
39. Sibony, M., et al., *Enhancement of mRNA in situ hybridization signal by microwave heating.* Lab Invest, 1995. 73(4): p. 586-91.
40. Fatkin, D., et al., *An abnormal Ca(2+) response in mutant sarcomere protein-mediated familial hypertrophic cardiomyopathy.* J Clin Invest, 2000. 106(11): p. 1351-9.
41. Mounkes, L. C., et al., *Expression of an LMNA-N195K variant of A-type lamins results in cardiac conduction defects and death in mice.* Hum Mol Genet, 2005. 14(15): p. 2167-80.

OTHER REFERENCES

Seidman, J. G. and C. Seidman, *The genetic basis for cardiomyopathy: from mutation identification to mechanistic paradigms.* Cell, 2001. 104(4): p. 557-67.

Flashman, E., et al., *Cardiac myosin binding protein C: its role in physiology and disease.* Circ Res, 2004. 94(10): p.1279-89.
Fougerousse, F., et al., *Cardiac myosin binding protein C gene is specifically expressed in heart during murine and human development.* Circ Res, 1998. 82(1): p. 130-3.
Gautel, M., et al., *Isoform transitions of the myosin binding protein C family in developing human and mouse muscles: lack of isoform transcomplementation in cardiac muscle.* Circ Res, 1998. 82(1): p. 124-9.
Alyonycheva, T. N., et al., *Isoform-specific interaction of the myosin-binding proteins (MyBPs) with skeletal and cardiac myosin is a property of the C-terminal immunoglobulin domain.* J Biol Chem, 1997. 272(33): p. 20866-72.
Freiburg, A. and M. Gautel, *A molecular map of the interactions between titin and myosin-binding protein C. Implications for sarcomeric assembly in familial hypertrophic cardiomyopathy.* Eur J Biochem, 1996. 235(1-2): p. 317-23.
Kulikovskaya, I., et al., *Effect of MyBP-C binding to actin on contractility in heart muscle.* J Gen Physiol, 2003. 122(6): p. 761-74.
Watkins, H., *Genetic clues to disease pathways in hypertrophic and dilated cardiomyopathies.* Circulation, 2003. 107(10): p. 1344-6.
Bonne, G., et al., *Familial hypertrophic cardiomyopathy: from mutations to functional defects.* Circ Res, 1998. 83(6): p. 580-93.
Carrier, L., et al., *Asymmetric septal hypertrophy in heterozygous cMyBP-C null mice.* Cardiovasc Res, 2004. 63(2): p. 293-304.
Harris, S. P., et al., *Hypertrophic cardiomyopathy in cardiac myosin binding protein-C knockout mice.* Circ Res, 2002. 90(5): p. 594-601.
McConnell, B. K., et al., *Dilated cardiomyopathy in homozygous myosin-binding protein-C mutant mice.* J Clin Invest, 1999. 104(9): p. 1235-44.

---

What is claimed is:

1. An isolated human muscle lamin A/C interacting protein encoded by the nucleotide sequence as set forth in SEQ ID NO: 88.

* * * * *

SEQUENCE LISTING

<160> NUMBER OF SEQ ID NOS: 106

<210> SEQ ID NO 1
<211> LENGTH: 66
<212> TYPE: DNA
<213> ORGANISM: Mus musculus

<400> SEQUENCE: 1
agcttttcca aaaagctgg tcgagaaacc aaatactctc ttgaagtatt tggtttctcg      60
accacg                                                                66

<210> SEQ ID NO 2
<211> LENGTH: 65
<212> TYPE: DNA
<213> ORGANISM: Mus musculus

<400> SEQUENCE: 2
gatccaatcc ctacaaacac attgttcaag agacaatgtg tttgtaggga ttgcttttt      60 ggaaa                                                                 65

<210> SEQ ID NO 3
<211> LENGTH: 64
<212> TYPE: DNA
<213> ORGANISM: Mus musculus

<400> SEQUENCE: 3
agcttttcca aaaaggaat tcaatacaaa ggaacctctc ttgaaggttc ctttgtattg    60
aatt                                                               64

<210> SEQ ID NO 4
<211> LENGTH: 65
<212> TYPE: DNA
<213> ORGANISM: Mus musculus

<400> SEQUENCE: 4
agcttttcca aaaagcaat ccctacaaac acattgtctc ttgaacaatg tgtttgtagg    60
gattg                                                              65

<210> SEQ ID NO 5
<211> LENGTH: 65
<212> TYPE: DNA
<213> ORGANISM: Mus musculus

<400> SEQUENCE: 5
gatccaattc aatacaaagg aaccttcaag agaggttcct ttgtattgaa ttcctttttt    60
ggaaa                                                              65

<210> SEQ ID NO 6
<211> LENGTH: 66
<212> TYPE: DNA
<213> ORGANISM: Mus musculus

<400> SEQUENCE: 6
gatccgtggt cgagaaacca atacttcaa gagagtattt ggtttctcga ccagcttttt    60
tggaaa                                                             66

<210> SEQ ID NO 7
<211> LENGTH: 269
<212> TYPE: PRT
<213> ORGANISM: Mus musculus

<400> SEQUENCE: 7

```
Met Glu Phe Gly Lys His Glu Pro Gly Ser Ser Leu Lys Arg Asn Lys
1               5                   10                  15

Asn Leu Glu Glu Gly Val Thr Phe Glu Tyr Ser Asp His Met Thr Phe
            20                  25                  30

Ser Ser Glu Ser Lys Gln Glu Arg Val Gln Arg Ile Leu Asp Tyr Pro
        35                  40                  45

Ser Glu Val Ser Gly Arg Asn Ser Gln Gln Lys Glu Phe Asn Thr Lys
    50                  55                  60

Glu Pro Gln Gly Met Gln Lys Gly Asp Leu Phe Lys Ala Glu Tyr Val
65                  70                  75                  80

Phe Ile Val Asp Ser Asp Gly Glu Asp Glu Ala Thr Cys Arg Gln Gly
                85                  90                  95

Glu Gln Gly Pro Pro Gly Gly Pro Gly Asn Ile Ala Thr Arg Pro Lys
            100                 105                 110

Ser Leu Ala Ile Ser Ser Leu Ala Ser Asp Val Val Arg Pro Lys
        115                 120                 125

Val Arg Gly Ala Asp Leu Lys Thr Ser Ser His Pro Glu Ile Pro His
    130                 135                 140

Gly Ile Ala Pro Gln Gln Lys His Gly Leu Ala Leu Asp Glu Pro Ala
145                 150                 155                 160
```

```
Arg Thr Glu Ser Asn Ser Lys Ala Ser Val Leu Asp Leu Pro Val Glu
            165                 170                 175

His Ser Ser Asp Ser Pro Ser Arg Pro Pro Gln Thr Met Leu Gly Ser
            180                 185                 190

Glu Thr Ile Lys Thr Pro Thr Thr His Pro Arg Ala Ala Gly Arg Glu
            195                 200                 205

Thr Lys Tyr Ala Asn Leu Ser Ser Ser Ser Thr Ala Ser Glu Ser
210                 215                 220

Gln Leu Thr Lys Pro Gly Val Ile Arg Pro Val Pro Val Lys Ser Lys
225                 230                 235                 240

Leu Leu Leu Arg Lys Asp Glu Glu Val Tyr Glu Pro Asn Pro Phe Ser
            245                 250                 255

Lys Tyr Leu Glu Asp Asn Ser Gly Leu Phe Ser Glu Gln
            260                 265

<210> SEQ ID NO 8
<211> LENGTH: 269
<212> TYPE: PRT
<213> ORGANISM: Mus musculus

<400> SEQUENCE: 8

Met Glu Phe Gly Lys His Glu Pro Gly Ser Ser Leu Lys Arg Asn Lys
1               5                   10                  15

Asn Leu Glu Glu Gly Val Thr Phe Glu Tyr Ser Asp His Met Thr Phe
            20                  25                  30

Ser Ser Glu Ser Lys Gln Glu Arg Val Gln Arg Ile Leu Asp Tyr Pro
            35                  40                  45

Ser Glu Val Ser Gly Arg Asn Ser Gln Gln Lys Glu Phe Asn Thr Lys
50                  55                  60

Glu Pro Gln Gly Met Gln Lys Gly Asp Leu Phe Lys Ala Glu Tyr Val
65                  70                  75                  80

Phe Ile Val Asp Ser Asp Gly Glu Asp Glu Ala Thr Cys Arg Gln Gly
            85                  90                  95

Glu Gln Gly Pro Pro Gly Gly Pro Gly Asn Ile Ala Thr Arg Pro Lys
            100                 105                 110

Ser Leu Ala Ile Ser Ser Ser Leu Ala Ser Asp Val Val Arg Pro Lys
            115                 120                 125

Val Arg Gly Ala Asp Leu Lys Thr Ser Ser His Pro Glu Ile Pro His
130                 135                 140

Gly Ile Ala Pro Gln Gln Lys His Gly Gln Ala Leu Asp Glu Pro Ala
145                 150                 155                 160

Arg Thr Glu Ser Asn Ser Lys Ala Ser Val Leu Asp Leu Pro Val Glu
            165                 170                 175

His Ser Ser Asp Ser Pro Ser Arg Pro Pro Gln Thr Met Leu Gly Ser
            180                 185                 190

Glu Thr Ile Lys Thr Pro Thr Thr His Pro Arg Ala Ala Gly Arg Glu
            195                 200                 205

Thr Lys Tyr Ala Asn Leu Ser Ser Ser Ser Thr Ala Ser Glu Ser
210                 215                 220

Gln Leu Thr Lys Pro Gly Val Ile Arg Pro Val Pro Val Lys Ser Lys
225                 230                 235                 240

Leu Leu Leu Arg Lys Asp Glu Glu Val Tyr Glu Pro Asn Pro Phe Ser
            245                 250                 255

Lys Tyr Leu Glu Asp Asn Ser Gly Leu Phe Ser Glu Gln
            260                 265
```

<210> SEQ ID NO 9
<211> LENGTH: 227
<212> TYPE: PRT
<213> ORGANISM: Mus musculus

<400> SEQUENCE: 9

Met Glu Phe Gly Lys His Glu Pro Gly Ser Ser Leu Lys Arg Asn Lys
1               5                   10                  15

Asn Leu Glu Glu Gly Val Thr Phe Glu Tyr Ser Asp His Met Thr Phe
            20                  25                  30

Ser Ser Glu Ser Lys Gln Glu Arg Val Gln Arg Ile Leu Asp Tyr Pro
        35                  40                  45

Ser Glu Val Ser Gly Arg Asn Ser Gln Gln Lys Glu Phe Asn Thr Lys
    50                  55                  60

Glu Pro Gln Gly Met Gln Lys Gly Asp Leu Phe Lys Ala Glu Tyr Val
65                  70                  75                  80

Phe Ile Val Asp Ser Asp Gly Glu Asp Glu Ala Thr Cys Arg Gln Gly
                85                  90                  95

Glu Gln Gly Pro Pro Gly Gly Pro Gly Asn Ile Ala Thr Arg Pro Lys
            100                 105                 110

Ser Leu Ala Ile Ser Ser Leu Ala Ser Asp Val Val Arg Pro Lys
        115                 120                 125

Val Arg Gly Ala Asp Leu Lys Thr Ser Ser His Pro Glu Ile Pro His
    130                 135                 140

Gly Ile Ala Pro Gln Gln Lys His Gly Gln Thr Pro Thr Thr His Pro
145                 150                 155                 160

Arg Ala Ala Gly Arg Glu Thr Lys Tyr Ala Asn Leu Ser Ser Ser Ser
                165                 170                 175

Ser Thr Ala Ser Glu Ser Gln Leu Thr Lys Pro Gly Val Ile Arg Pro
            180                 185                 190

Val Pro Val Lys Ser Lys Leu Leu Arg Lys Asp Glu Glu Val Tyr
    195                 200                 205

Glu Pro Asn Pro Phe Ser Lys Tyr Leu Glu Asp Asn Ser Gly Leu Phe
    210                 215                 220

Ser Glu Gln
225

<210> SEQ ID NO 10
<211> LENGTH: 279
<212> TYPE: PRT
<213> ORGANISM: Mus musculus

<400> SEQUENCE: 10

Met Glu Phe Gly Lys His Glu Pro Gly Ser Ser Leu Lys Arg Asn Lys
1               5                   10                  15

Asn Leu Glu Glu Gly Val Thr Val Ser Pro Gly Asp Pro Glu Ala Lys
            20                  25                  30

Pro Leu Ile Phe Thr Phe Val Pro Thr Leu Arg Arg Leu Pro Thr His
        35                  40                  45

Ile Gln Leu Ala Asp Thr Ser Lys Phe Leu Val Lys Ile Pro Glu Glu
    50                  55                  60

Pro Thr Asp Lys Ser Pro Glu Thr Val Asn Arg Phe Glu Tyr Ser Asp
65                  70                  75                  80

His Met Thr Phe Ser Ser Glu Ser Lys Gln Glu Arg Val Gln Arg Ile
                85                  90                  95

```
Leu Asp Tyr Pro Ser Glu Val Ser Gly Arg Asn Ser Gln Gln Lys Glu
            100                 105                 110

Phe Asn Thr Lys Glu Pro Gln Gly Met Gln Lys Gly Asp Leu Phe Lys
            115                 120                 125

Ala Glu Tyr Val Phe Ile Val Asp Ser Asp Gly Glu Asp Glu Ala Thr
            130                 135                 140

Cys Arg Gln Gly Glu Gln Gly Pro Pro Gly Gly Pro Gly Asn Ile Ala
145                 150                 155                 160

Thr Arg Pro Lys Ser Leu Ala Ile Ser Ser Ser Leu Ala Ser Asp Val
                165                 170                 175

Val Arg Pro Lys Val Arg Gly Ala Asp Leu Lys Thr Ser Ser His Pro
            180                 185                 190

Glu Ile Pro His Gly Ile Ala Pro Gln Gln Lys His Gly Gln Thr Pro
            195                 200                 205

Thr Thr His Pro Arg Ala Ala Gly Arg Glu Thr Lys Tyr Ala Asn Leu
            210                 215                 220

Ser Ser Ser Ser Thr Ala Ser Glu Ser Gln Leu Thr Lys Pro Gly
225                 230                 235                 240

Val Ile Arg Pro Val Pro Val Lys Ser Lys Leu Leu Leu Arg Lys Asp
                245                 250                 255

Glu Glu Val Tyr Glu Pro Asn Pro Phe Ser Lys Tyr Leu Glu Asp Asn
            260                 265                 270

Ser Gly Leu Phe Ser Glu Gln
            275

<210> SEQ ID NO 11
<211> LENGTH: 442
<212> TYPE: PRT
<213> ORGANISM: Mus musculus

<400> SEQUENCE: 11

Met Glu Phe Gly Lys His Glu Pro Gly Ser Ser Leu Lys Arg Asn Lys
1               5                   10                  15

Asn Leu Glu Glu Gly Val Thr Val Ser Pro Gly Asp Pro Glu Ala Lys
            20                  25                  30

Pro Leu Ile Phe Thr Phe Val Pro Thr Leu Arg Arg Leu Pro Thr His
            35                  40                  45

Ile Gln Leu Ala Asp Thr Ser Lys Phe Leu Val Lys Ile Pro Glu Glu
        50                  55                  60

Pro Thr Asp Lys Ser Pro Glu Thr Val Asn Arg Phe Glu Tyr Ser Asp
65                  70                  75                  80

His Met Thr Phe Ser Ser Glu Ser Lys Gln Glu Arg Val Gln Arg Ile
                85                  90                  95

Leu Asp Tyr Pro Ser Glu Val Ser Gly Arg Asn Ser Gln Gln Lys Glu
            100                 105                 110

Phe Asn Thr Lys Glu Pro Gln Gly Met Gln Lys Gly Asp Leu Phe Lys
            115                 120                 125

Ala Glu Tyr Val Phe Ile Val Asp Ser Asp Gly Glu Asp Glu Ala Thr
            130                 135                 140

Cys Arg Gln Gly Glu Gln Gly Pro Pro Gly Gly Pro Gly Asn Ile Ala
145                 150                 155                 160

Thr Arg Pro Lys Ser Leu Ala Ile Ser Ser Ser Leu Ala Ser Asp Val
                165                 170                 175

Val Arg Pro Lys Val Arg Gly Ala Asp Leu Lys Thr Ser Ser His Pro
            180                 185                 190
```

```
Glu Ile Pro His Gly Ile Ala Pro Gln Gln Lys His Gly Gln Gln Tyr
        195                 200                 205

Lys Thr Met Ser Ser Tyr Lys Ala Phe Ala Ala Ile Pro Thr Asn Thr
        210                 215                 220

Leu Leu Leu Glu Gln Lys Ala Leu Asp Glu Pro Ala Arg Thr Glu Ser
225                 230                 235                 240

Asn Ser Lys Ala Ser Val Leu Asp Leu Pro Val Glu Phe Cys Phe Pro
                245                 250                 255

Ala Gln Leu Arg Gln Gln Thr Glu Glu Leu Cys Ala Thr Ile Asp Lys
                260                 265                 270

Val Leu Gln Asp Ser Leu Ser Met His Ser Ser Asp Ser Pro Ser Arg
                275                 280                 285

Pro Pro Gln Thr Met Leu Gly Ser Glu Thr Ile Lys Thr Pro Thr Thr
        290                 295                 300

His Pro Arg Ala Ala Gly Arg Glu Thr Lys Tyr Ala Asn Leu Ser Ser
305                 310                 315                 320

Ser Ser Ser Thr Ala Ser Glu Ser Gln Leu Thr Lys Pro Gly Val Ile
                325                 330                 335

Arg Pro Val Pro Val Lys Ser Lys Leu Leu Leu Arg Lys Asp Glu Glu
                340                 345                 350

Val Tyr Glu Pro Asn Pro Phe Ser Lys Tyr Leu Glu Asp Asn Ser Gly
                355                 360                 365

Leu Phe Ser Glu Gln Asp Met Ala Ile Pro His Lys Pro Val Ser Leu
        370                 375                 380

His Pro Leu Tyr Gln Ser Lys Leu Tyr Pro Pro Ala Lys Ser Leu Leu
385                 390                 395                 400

His Pro Gln Thr Leu Ser His Ala Asp Cys Leu Thr Pro Gly Leu Phe
                405                 410                 415

Ser His Leu Ser Ser Phe Ser Val Arg Asp Glu Gln Glu Lys Ser Pro
                420                 425                 430

Thr Leu Leu Ser Gln Asp Thr Tyr Asn Lys
        435                 440

<210> SEQ ID NO 12
<211> LENGTH: 269
<212> TYPE: PRT
<213> ORGANISM: Mus musculus

<400> SEQUENCE: 12

Met Glu Phe Gly Lys His Glu Pro Gly Ser Ser Leu Lys Arg Asn Lys
1               5                   10                  15

Asn Leu Glu Glu Gly Val Thr Phe Glu Tyr Ser Asp His Met Thr Phe
                20                  25                  30

Ser Ser Glu Ser Lys Gln Glu Arg Val Gln Arg Ile Leu Asp Tyr Pro
        35                  40                  45

Ser Glu Val Ser Gly Arg Asn Ser Gln Gln Lys Glu Phe Asn Thr Lys
    50                  55                  60

Glu Pro Gln Gly Met Gln Lys Gly Asp Leu Phe Lys Ala Glu Tyr Val
65                  70                  75                  80

Phe Ile Val Asp Ser Asp Gly Glu Asp Glu Ala Thr Cys Arg Gln Gly
                85                  90                  95

Glu Gln Gly Pro Pro Gly Gly Pro Gly Asn Ile Ala Thr Arg Pro Lys
            100                 105                 110

Ser Leu Ala Ile Ser Ser Leu Ala Ser Asp Val Val Arg Pro Lys
        115                 120                 125
```

```
Val Arg Gly Ala Asp Leu Lys Thr Ser Ser His Pro Glu Ile Pro His
            130                 135                 140
Gly Ile Ala Pro Gln Gln Lys His Gly Leu Ala Leu Asp Glu Pro Ala
145                 150                 155                 160
Arg Thr Glu Ser Asn Ser Lys Ala Ser Val Leu Asp Leu Pro Val Glu
                165                 170                 175
His Ser Ser Asp Ser Pro Ser Arg Pro Pro Gln Thr Met Leu Gly Ser
            180                 185                 190
Glu Thr Ile Lys Thr Pro Thr Thr His Pro Arg Ala Ala Gly Arg Glu
            195                 200                 205
Thr Lys Tyr Ala Asn Leu Ser Ser Ser Ser Thr Ala Ser Glu Ser
210                 215                 220
Gln Leu Thr Lys Pro Gly Val Ile Arg Pro Val Pro Val Lys Ser Lys
225                 230                 235                 240
Leu Leu Leu Arg Lys Asp Glu Val Tyr Glu Pro Asn Pro Phe Ser
                245                 250                 255
Lys Tyr Leu Glu Asp Asn Ser Gly Leu Phe Ser Glu Gln
            260                 265

<210> SEQ ID NO 13
<211> LENGTH: 279
<212> TYPE: PRT
<213> ORGANISM: Mus musculus

<400> SEQUENCE: 13

Met Glu Phe Gly Lys His Glu Pro Gly Ser Ser Leu Lys Arg Asn Lys
1               5                   10                  15
Asn Leu Glu Glu Gly Val Thr Val Ser Pro Gly Asp Pro Glu Ala Lys
            20                  25                  30
Pro Leu Ile Phe Thr Phe Val Pro Thr Leu Arg Arg Leu Pro Thr His
        35                  40                  45
Ile Gln Leu Ala Asp Thr Ser Lys Phe Leu Val Lys Ile Pro Glu Glu
    50                  55                  60
Pro Thr Asp Lys Ser Pro Glu Thr Val Asn Arg Phe Glu Tyr Ser Asp
65                  70                  75                  80
His Met Thr Phe Ser Ser Glu Ser Lys Gln Glu Arg Val Gln Arg Ile
                85                  90                  95
Leu Asp Tyr Pro Ser Glu Val Ser Gly Arg Asn Ser Gln Gln Lys Glu
            100                 105                 110
Phe Asn Thr Lys Glu Pro Gln Gly Met Gln Lys Gly Asp Leu Phe Lys
        115                 120                 125
Ala Glu Tyr Val Phe Ile Val Asp Ser Asp Gly Glu Asp Glu Ala Thr
130                 135                 140
Cys Arg Gln Gly Glu Gln Gly Pro Pro Gly Gly Pro Gly Asn Ile Ala
145                 150                 155                 160
Thr Arg Pro Lys Ser Leu Ala Ile Ser Ser Leu Ala Ser Asp Val
                165                 170                 175
Val Arg Pro Lys Val Arg Gly Ala Asp Leu Lys Thr Ser Ser His Pro
            180                 185                 190
Glu Ile Pro His Gly Ile Ala Pro Gln Gln Lys His Gly Leu Thr Pro
        195                 200                 205
Thr Thr His Pro Arg Ala Ala Gly Arg Glu Thr Lys Tyr Ala Asn Leu
    210                 215                 220
Ser Ser Ser Ser Ser Thr Ala Ser Glu Ser Gln Leu Thr Lys Pro Gly
225                 230                 235                 240
```

Val Ile Arg Pro Val Pro Val Lys Ser Lys Leu Leu Arg Lys Asp
            245                 250                 255

Glu Glu Val Tyr Glu Pro Asn Pro Phe Ser Lys Tyr Leu Glu Asp Asn
        260                 265                 270

Ser Gly Leu Phe Ser Glu Gln
        275

<210> SEQ ID NO 14
<211> LENGTH: 271
<212> TYPE: PRT
<213> ORGANISM: Mus musculus

<400> SEQUENCE: 14

Met Thr Ser Cys Ile Leu Ala Gly Ser Leu Glu Thr Thr Pro Lys Val
1               5                   10                  15

Ser Pro Gly Asp Pro Glu Ala Lys Pro Leu Ile Phe Thr Phe Val Pro
            20                  25                  30

Thr Leu Arg Arg Leu Pro Thr His Ile Gln Leu Ala Asp Thr Ser Lys
        35                  40                  45

Phe Leu Val Lys Ile Pro Glu Glu Pro Thr Asp Lys Ser Pro Glu Thr
    50                  55                  60

Val Asn Arg Phe Glu Tyr Ser Asp His Met Thr Phe Ser Ser Glu Ser
65                  70                  75                  80

Lys Gln Glu Arg Val Gln Arg Ile Leu Asp Tyr Pro Ser Glu Val Ser
                85                  90                  95

Gly Arg Asn Ser Gln Gln Lys Glu Phe Asn Thr Lys Glu Pro Gln Gly
            100                 105                 110

Met Gln Lys Gly Asp Leu Phe Lys Ala Glu Tyr Val Phe Ile Val Asp
        115                 120                 125

Ser Asp Gly Glu Asp Glu Ala Thr Cys Arg Gln Gly Glu Gln Gly Pro
    130                 135                 140

Pro Gly Gly Pro Gly Asn Ile Ala Thr Arg Pro Lys Ser Leu Ala Ile
145                 150                 155                 160

Ser Ser Ser Leu Ala Ser Asp Val Val Arg Pro Lys Val Arg Gly Ala
                165                 170                 175

Asp Leu Lys Thr Ser Ser His Pro Glu Ile Pro His Gly Ile Ala Pro
            180                 185                 190

Gln Gln Lys His Gly Leu Thr Pro Thr Thr His Pro Arg Ala Ala Gly
        195                 200                 205

Arg Glu Thr Lys Tyr Ala Asn Leu Ser Ser Ser Ser Thr Ala Ser
    210                 215                 220

Glu Ser Gln Leu Thr Lys Pro Gly Val Ile Arg Pro Val Pro Val Lys
225                 230                 235                 240

Ser Lys Leu Leu Leu Arg Lys Asp Glu Glu Val Tyr Glu Pro Asn Pro
                245                 250                 255

Phe Ser Lys Tyr Leu Glu Asp Asn Ser Gly Leu Phe Ser Glu Gln
            260                 265                 270

<210> SEQ ID NO 15
<211> LENGTH: 227
<212> TYPE: PRT
<213> ORGANISM: Mus musculus

<400> SEQUENCE: 15

Met Glu Phe Gly Lys His Glu Pro Gly Ser Ser Leu Lys Arg Asn Lys
1               5                   10                  15

Asn Leu Glu Glu Gly Val Thr Phe Glu Tyr Ser Asp His Met Thr Phe

```
                20              25              30
Ser Ser Glu Ser Lys Gln Glu Arg Val Gln Arg Ile Leu Asp Tyr Pro
            35              40              45

Ser Glu Val Ser Gly Arg Asn Ser Gln Gln Lys Glu Phe Asn Thr Lys
        50              55              60

Glu Pro Gln Gly Met Gln Lys Gly Asp Leu Phe Lys Ala Glu Tyr Val
65              70              75              80

Phe Ile Val Asp Ser Asp Gly Asp Glu Ala Thr Cys Arg Gln Gly
                85              90              95

Glu Gln Gly Pro Pro Gly Gly Pro Gly Asn Ile Ala Thr Arg Pro Lys
            100             105             110

Ser Leu Ala Ile Ser Ser Leu Ala Ser Asp Val Val Arg Pro Lys
        115             120             125

Val Arg Gly Ala Asp Leu Lys Thr Ser Ser His Pro Glu Ile Pro His
        130             135             140

Gly Ile Ala Pro Gln Gln Lys His Gly Leu Thr Pro Thr Thr His Pro
145             150             155             160

Arg Ala Ala Gly Arg Glu Thr Lys Tyr Ala Asn Leu Ser Ser Ser Ser
            165             170             175

Ser Thr Ala Ser Glu Ser Gln Leu Thr Lys Pro Gly Val Ile Arg Pro
            180             185             190

Val Pro Val Lys Ser Lys Leu Leu Arg Lys Asp Glu Val Tyr
            195             200             205

Glu Pro Asn Pro Phe Ser Lys Tyr Leu Glu Asp Asn Ser Gly Leu Phe
        210             215             220

Ser Glu Gln
225

<210> SEQ ID NO 16
<211> LENGTH: 227
<212> TYPE: PRT
<213> ORGANISM: Mus musculus

<400> SEQUENCE: 16

Met Glu Phe Gly Lys His Glu Pro Gly Ser Leu Lys Arg Asn Lys
1               5               10              15

Asn Leu Glu Glu Gly Val Thr Phe Glu Tyr Ser Asp His Met Thr Phe
            20              25              30

Ser Ser Glu Ser Lys Gln Glu Arg Val Gln Arg Ile Leu Asp Tyr Pro
            35              40              45

Ser Glu Val Ser Gly Arg Asn Ser Gln Gln Lys Glu Phe Asn Thr Lys
        50              55              60

Glu Pro Gln Gly Met Gln Lys Gly Asp Leu Phe Lys Ala Glu Tyr Val
65              70              75              80

Phe Ile Val Asp Ser Asp Gly Asp Glu Ala Thr Cys Arg Gln Gly
                85              90              95

Glu Gln Gly Pro Pro Gly Gly Pro Gly Asn Ile Ala Thr Arg Pro Lys
            100             105             110

Ser Leu Ala Ile Ser Ser Asn Leu Ala Ser Asp Val Val Arg Pro Lys
        115             120             125

Val Arg Gly Ala Asp Leu Lys Thr Ser Ser His Pro Glu Ile Pro His
        130             135             140

Gly Ile Ala Pro Gln Gln Lys His Gly Leu Thr Pro Thr Thr His Pro
145             150             155             160

Arg Ala Ala Gly Arg Glu Thr Lys Tyr Ala Asn Leu Ser Ser Ser Ser
```

```
                         165                 170                 175
Ser Thr Ala Ser Glu Ser Gln Leu Thr Lys Pro Gly Val Ile Arg Pro
            180                 185                 190

Val Pro Val Lys Ser Lys Leu Leu Leu Arg Lys Asp Glu Glu Val Tyr
        195                 200                 205

Glu Pro Asn Pro Phe Ser Lys Tyr Leu Glu Asp Asn Ser Gly Leu Phe
    210                 215                 220

Ser Glu Gln
225

<210> SEQ ID NO 17
<211> LENGTH: 24
<212> TYPE: DNA
<213> ORGANISM: Artificial
<220> FEATURE:
<223> OTHER INFORMATION: primer sequence

<400> SEQUENCE: 17
ttccattctg tctctttcta cctc                                              24

<210> SEQ ID NO 18
<211> LENGTH: 24
<212> TYPE: DNA
<213> ORGANISM: Artificial
<220> FEATURE:
<223> OTHER INFORMATION: primer sequence

<400> SEQUENCE: 18
aacccacatt cagttggctg acac                                              24

<210> SEQ ID NO 19
<211> LENGTH: 24
<212> TYPE: DNA
<213> ORGANISM: Artificial
<220> FEATURE:
<223> OTHER INFORMATION: primer sequence

<400> SEQUENCE: 19
agagcaaaca agagagggtc caga                                              24

<210> SEQ ID NO 20
<211> LENGTH: 24
<212> TYPE: DNA
<213> ORGANISM: Artificial
<220> FEATURE:
<223> OTHER INFORMATION: primer sequence

<400> SEQUENCE: 20
accagctgct cttggatgag ttgt                                              24

<210> SEQ ID NO 21
<211> LENGTH: 24
<212> TYPE: DNA
<213> ORGANISM: Artificial
<220> FEATURE:
<223> OTHER INFORMATION: primer sequence

<400> SEQUENCE: 21
accagctgct cttggatgag ttgt                                              24

<210> SEQ ID NO 22
<211> LENGTH: 21
<212> TYPE: DNA
<213> ORGANISM: Artificial
<220> FEATURE:
```

<223> OTHER INFORMATION: primer sequence

<400> SEQUENCE: 22
ccaggaagct cactaaagag g                                    21

<210> SEQ ID NO 23
<211> LENGTH: 24
<212> TYPE: DNA
<213> ORGANISM: Artificial
<220> FEATURE:
<223> OTHER INFORMATION: primer sequence

<400> SEQUENCE: 23
acatgcagac aaggtgaaca aggc                                 24

<210> SEQ ID NO 24
<211> LENGTH: 24
<212> TYPE: DNA
<213> ORGANISM: Artificial
<220> FEATURE:
<223> OTHER INFORMATION: primer sequence

<400> SEQUENCE: 24
aagcatgggc tgcaatacaa gacc                                 24

<210> SEQ ID NO 25
<211> LENGTH: 24
<212> TYPE: DNA
<213> ORGANISM: Artificial
<220> FEATURE:
<223> OTHER INFORMATION: primer sequence

<400> SEQUENCE: 25
tgagagcaaa caagagaggg tcca                                 24

<210> SEQ ID NO 26
<211> LENGTH: 24
<212> TYPE: DNA
<213> ORGANISM: Artificial
<220> FEATURE:
<223> OTHER INFORMATION: primer sequence

<400> SEQUENCE: 26
caacccacat tcagttggct gaca                                 24

<210> SEQ ID NO 27
<211> LENGTH: 24
<212> TYPE: DNA
<213> ORGANISM: Artificial
<220> FEATURE:
<223> OTHER INFORMATION: primer sequence

<400> SEQUENCE: 27
gccttgttca ccttgtctgc atgt                                 24

<210> SEQ ID NO 28
<211> LENGTH: 24
<212> TYPE: DNA
<213> ORGANISM: Artificial
<220> FEATURE:
<223> OTHER INFORMATION: primer sequence

<400> SEQUENCE: 28
tggagatcct gaagccaaac ctct                                 24

<210> SEQ ID NO 29

```
<211> LENGTH: 24
<212> TYPE: DNA
<213> ORGANISM: Artificial
<220> FEATURE:
<223> OTHER INFORMATION: primer sequence

<400> SEQUENCE: 29
tgcgtatttg gtttctcgac cagc                                              24

<210> SEQ ID NO 30
<211> LENGTH: 24
<212> TYPE: DNA
<213> ORGANISM: Artificial
<220> FEATURE:
<223> OTHER INFORMATION: primer sequence

<400> SEQUENCE: 30
ttagtcagtt ggctctcaga cgct                                              24

<210> SEQ ID NO 31
<211> LENGTH: 24
<212> TYPE: DNA
<213> ORGANISM: Artificial
<220> FEATURE:
<223> OTHER INFORMATION: primer sequence

<400> SEQUENCE: 31
aagcatgggc tgcaatacaa gacc                                              24

<210> SEQ ID NO 32
<211> LENGTH: 24
<212> TYPE: DNA
<213> ORGANISM: Artificial
<220> FEATURE:
<223> OTHER INFORMATION: primer sequence

<400> SEQUENCE: 32
acaggccact gttgtcttca aggt                                              24

<210> SEQ ID NO 33
<211> LENGTH: 24
<212> TYPE: DNA
<213> ORGANISM: Artificial
<220> FEATURE:
<223> OTHER INFORMATION: primer sequence

<400> SEQUENCE: 33
ttccactcca gcttccttac tgct                                              24

<210> SEQ ID NO 34
<211> LENGTH: 24
<212> TYPE: DNA
<213> ORGANISM: Artificial
<220> FEATURE:
<223> OTHER INFORMATION: primer sequence

<400> SEQUENCE: 34
aacatagcta ctcggcccaa gtct                                              24

<210> SEQ ID NO 35
<211> LENGTH: 24
<212> TYPE: DNA
<213> ORGANISM: Artificial
<220> FEATURE:
<223> OTHER INFORMATION: primer sequence

<400> SEQUENCE: 35
```
ggtcttgtat tgcagcccat gctt                                              24

<210> SEQ ID NO 36
<211> LENGTH: 24
<212> TYPE: DNA
<213> ORGANISM: Artificial
<220> FEATURE:
<223> OTHER INFORMATION: primer sequence

<400> SEQUENCE: 36
atggtcttgt attgcagccc atgc                                              24

<210> SEQ ID NO 37
<211> LENGTH: 24
<212> TYPE: DNA
<213> ORGANISM: Artificial
<220> FEATURE:
<223> OTHER INFORMATION: primer sequence

<400> SEQUENCE: 37
tggaccctct cttgtttgct ctca                                              24

<210> SEQ ID NO 38
<211> LENGTH: 24
<212> TYPE: DNA
<213> ORGANISM: Artificial
<220> FEATURE:
<223> OTHER INFORMATION: primer sequence

<400> SEQUENCE: 38
tggagatcct gaagccaaac ctct                                              24

<210> SEQ ID NO 39
<211> LENGTH: 24
<212> TYPE: DNA
<213> ORGANISM: Artificial
<220> FEATURE:
<223> OTHER INFORMATION: primer sequence

<400> SEQUENCE: 39
ggtcttgtat tgcagcccat gctt                                              24

<210> SEQ ID NO 40
<211> LENGTH: 24
<212> TYPE: DNA
<213> ORGANISM: Artificial
<220> FEATURE:
<223> OTHER INFORMATION: primer sequence

<400> SEQUENCE: 40
gtgtcagcca actgaatgtg ggtt                                              24

<210> SEQ ID NO 41
<211> LENGTH: 24
<212> TYPE: DNA
<213> ORGANISM: Artificial
<220> FEATURE:
<223> OTHER INFORMATION: primer sequence

<400> SEQUENCE: 41
aacccacatt cagttggctg acac                                              24

<210> SEQ ID NO 42
<211> LENGTH: 24
<212> TYPE: DNA
<213> ORGANISM: Artificial
<220> FEATURE:

<223> OTHER INFORMATION: primer sequence

<400> SEQUENCE: 42
acatgcagac aaggtgaaca aggc                                    24

<210> SEQ ID NO 43
<211> LENGTH: 24
<212> TYPE: DNA
<213> ORGANISM: Artificial
<220> FEATURE:
<223> OTHER INFORMATION: primer sequence

<400> SEQUENCE: 43
cacttccact ccagcttcct tact                                    24

<210> SEQ ID NO 44
<211> LENGTH: 24
<212> TYPE: DNA
<213> ORGANISM: Artificial
<220> FEATURE:
<223> OTHER INFORMATION: primer sequence

<400> SEQUENCE: 44
atggtcttgt attgcagccc atgc                                    24

<210> SEQ ID NO 45
<211> LENGTH: 24
<212> TYPE: DNA
<213> ORGANISM: Artificial
<220> FEATURE:
<223> OTHER INFORMATION: primer sequence

<400> SEQUENCE: 45
tgagagcaaa caagagaggg tcca                                    24

<210> SEQ ID NO 46
<211> LENGTH: 24
<212> TYPE: DNA
<213> ORGANISM: Artificial
<220> FEATURE:
<223> OTHER INFORMATION: primer sequence

<400> SEQUENCE: 46
gccttgttca ccttgtctgc atgt                                    24

<210> SEQ ID NO 47
<211> LENGTH: 743
<212> TYPE: DNA
<213> ORGANISM: Mus musculus
<220> FEATURE:
<221> NAME/KEY: misc_feature
<222> LOCATION: (742)..(742)
<223> OTHER INFORMATION: n = any nucleotide

<400> SEQUENCE: 47
cacttccact ccagcttcct tactgctcag aaaacaggcc actgttgtct tcaaggtatt    60
tactgaaagg gttgggctca taaacttctt cgtcctttct caggagtagt ttggatttta   120
caggtactgg acgaattact ccaggcttag tcagttggct ctcagacgct gttgaggatg   180
atgaagaaag atttgcgtat ttggtttctc gaccagctgc tcttggatga gttgtaggag   240
tcagcccatg cttttgctga ggggctatcc catgaggaat tcaggatgt gatgaggtct    300 tgagatcagc cctcgtact ttgggacgca ccacgtcaga agccagacta gaagaaatag    360
ccagagactt gagccgagta gctatgttgc ctggtccccc tggggggcct tgttcacctt    420

| | |
|---|---|
| gtctgcatgt agcttcatct tccccatcag aatccgcaat aaaaacatat tctgctttga | 480 |
| agagatcacc tttctgcatt ccttgaggtt cctttgtatt gaattccttt tgttgtgaat | 540 |
| tcctcccact gacctctgac ggataatcca gtatcctctg gaccctctct tgtttgctct | 600 |
| cagagctgaa ggtcatatga tcactgtact caaacgtcac tccctcctct aagttcttgt | 660 |
| tcctctttag tgagcttcct ggttcatgct ttccaaattc catggtgaaa gaatgagaga | 720 |
| gaggtagaaa gagacagaat gna | 743 |

<210> SEQ ID NO 48
<211> LENGTH: 286
<212> TYPE: DNA
<213> ORGANISM: Mus musculus

<400> SEQUENCE: 48

| | |
|---|---|
| gacaccggtc tgctgaagag ttttggaatg atgccatggc caactacttg ctaaacttac | 60 |
| ctgatgcttt gttagaagga gtgctctgct cagtccagca gaagcacctg aatggtttgc | 120 |
| cacagccaca tagcattacc acactctggg aaacccagag caggatcata gcccttctgt | 180 |
| ttcttgcatt gccgttcaag cctataatgc cttctattaa gtcaacagca atactaatgt | 240 |
| tcccctatat ttagcagtca aataaagaag aatgatagct gaatac | 286 |

<210> SEQ ID NO 49
<211> LENGTH: 696
<212> TYPE: DNA
<213> ORGANISM: Mus musculus

<400> SEQUENCE: 49

| | |
|---|---|
| tccattctgt ctctttctac ctctctctca ttctttcacc atggaatttg gaaagcatga | 60 |
| accaggaagc tcactaaaga ggaacaagaa cttagaggag ggagtgacgt ttgagtacag | 120 |
| tgatcatatg accttcagct ctgagagcaa acaagagagg gtccagagga tactggatta | 180 |
| tccgtcagag gtcagtggga ggaattcaca acaaaaggaa ttcaatacaa aggaacctca | 240 |
| aggaatgcag aaaggtgatc tcttcaaagc agaatatgtt tttattgagg attctgatgg | 300 |
| ggaagatgaa gctacatgca gacaaggtga caaggcccc ccaggggac caggcaacat | 360 |
| agctactcgg cccaagtctc tggctatttc ttctagtctg gcttctgacg tggtgcgtcc | 420 |
| caaagtacga ggggctgatc tcaagacctc atcacatcct gaaattcctc atgggatagc | 480 |
| ccctcagcaa aagcatgggc tgactcctac aactcatcca agagcagctg gtcgagaaac | 540 |
| caaatacgca aatctttctt catcatcctc aacagcgtct gagagccaac tgactaagcc | 600 |
| tggagtaatt cgtccagtac ctgtaaaatc caaactactc ctgagaaagg atgaagaagt | 660 |
| ttatgagccc aaccctttca gtaaataccT tgaaga | 696 |

<210> SEQ ID NO 50
<211> LENGTH: 422
<212> TYPE: DNA
<213> ORGANISM: Mus musculus

<400> SEQUENCE: 50

| | |
|---|---|
| tccattctgt ctctttctac ctctctctca ttctttcacc atggaatttg gaaagcatga | 60 |
| accaggaagc tcactaaaga ggaacaagaa cttagaggag ggagtgacgc aatacaagac | 120 |
| catgtcaagc tacaaggctt ttgcagcaat ccctacaaac acattgctct ggaacagaa | 180 |
| gactcctaca actcatccaa gagcagctgg tcgagaaacc aaatacgcaa atctttcttc | 240 |
| atcatcctca acagcgtctg agagccaact gactaagcct ggagtaattc gtccagtacc | 300 |

```
tgtaaaatcc aaactactcc tgagaaagaa tgaagaagtt tatgagccca acccttttcag    360 taaatacctt gaagacaaca gtggcctgtt ttctgagcag taaggaagct ggagtggaag    420
tg                                                                    422
```

<210> SEQ ID NO 51
<211> LENGTH: 165
<212> TYPE: DNA
<213> ORGANISM: Mus musculus
<220> FEATURE:
<221> NAME/KEY: misc_feature
<222> LOCATION: (149)..(150)
<223> OTHER INFORMATION: n = any nucleotide

<400> SEQUENCE: 51

```
tcataaactt cttcatcctt tctcaggagt agtttggatt ttacaggtac tggacgaatt     60
actccaggct tagtcagttg gctctcagac gctgttgagg atgatgaaga aagatttgcg    120
tatttggttt ctcgaccagc tgctcttgnn tgagttgtag gagtc                    165
```

<210> SEQ ID NO 52
<211> LENGTH: 737
<212> TYPE: DNA
<213> ORGANISM: Mus musculus

<400> SEQUENCE: 52

```
tccattctgt ctctttctac ctctctctca ttctttcacc atggaatttg gaaagcatga     60
accaggaagc tcactaaaga ggaacaagaa cttagaggag ggagtgacgt ttgagtacag    120
tgatcatatg accttcagct ctgagagcaa acaagagagg gtccagagga tactggatta    180
tccgtcagag gtcagtggga ggaattcaca acaaaaggaa ttcaatacaa aggaaccctca   240 aggaatgcag aaaggtgatc tcttcaaagc agaatatgtt tttattgtgg attctgatgg    300
ggaagatgaa gctacatgca gacaaggtga acaaggcccc caggggggac caggcaacat    360
agctactcgg cccaagtctc tggctatttc ttctagtctg gcttctgacg tggtgcgtcc    420
caaagtacga ggggctgatc tcaagacctc atcacatcct gaaattcctc atgggatagc    480
ccctcagcaa aagcatgggc tgactcctac aactcatcca agagcagctg gtcgagaaac    540
caaatacgca aatctttctt catcatcctc aacagcgtct gagagccaac tgactaagcc    600
tggagtaatt cgtccagtac ctgtaaaatc caaactactc ctgagaaagg atgaagaagt    660
ttatgagccc aaccctttca gtaaatacct tgaagacaac agtggcctgt tttctgagca    720
gtaaggaagc tggagtg                                                    737
```

<210> SEQ ID NO 53
<211> LENGTH: 726
<212> TYPE: DNA
<213> ORGANISM: Mus musculus

<400> SEQUENCE: 53

```
cacttccact ccagcttcct tactgctcag aaaacaggcc actgttgtct tcaaggtatt     60
tactgaaagg gttgggctca taaacttctt catccttttct caggagtagt ttggattttta  120 caggtactgg acgaattact ccaggcttag tcagttggct ctcagacgct gttgaggatg    180
atgaagaaag atttgcgtat ttggtttctc gaccagctgc tcttggatga gttgtaggag    240
tcagcccatg cttttgctga ggggctatcc catgaggaat tcaggatgt gatgaggtct     300 tgagatcagc cctcgtact ttgggacgca ccacgtcaga agccagacta gaagaaatag     360
ccagagactt gggccgagta gctatgttgc ctggtccccc tgggggccct tgttcacctt    420
```

| | |
|---|---|
| gtctgcatgt agcttcatct tccccatcag aatccacaat aaaaacatat tctgctttga | 480 |
| agagatcacc tttctgcatt ccttgaggtt cctttgtatt gaattccttt tgttgtgaat | 540 |
| tcctcccact gacctctgac ggataatcca gtatcctctg gaccctctct tgtttgctct | 600 |
| cagagctgaa ggtcatatga tcactgtact caaacgtcac tccctcctct aagttcttgt | 660 |
| tcctctttag tgagcttcct ggttcatgct ttccaaattc catggtgaaa gaatgagaga | 720 |
| ggtaga | 726 |

<210> SEQ ID NO 54
<211> LENGTH: 838
<212> TYPE: DNA
<213> ORGANISM: Mus musculus
<220> FEATURE:
<221> NAME/KEY: misc_feature
<222> LOCATION: (762)..(762)
<223> OTHER INFORMATION: n = any nucleotide
<220> FEATURE:
<221> NAME/KEY: misc_feature
<222> LOCATION: (769)..(770)
<223> OTHER INFORMATION: n = any nucleotide
<220> FEATURE:
<221> NAME/KEY: misc_feature
<222> LOCATION: (816)..(816)
<223> OTHER INFORMATION: n = any nucleotide

<400> SEQUENCE: 54

| | |
|---|---|
| cacttccact ccagcttcct tactgctcag aaaacaggcc actgttgtct tcaaggtatt | 60 |
| tactgaaagg gttgggctca taaacttctt catcctttct caggagtagt ttggatttta | 120 |
| caggtactgg acgaattact ccaggcttag tcagttggct ctcagacgct gttgaggatg | 180 |
| atgaagaaag atttgcgtat ttggtttctc gaccagctgc tcttggatga gttgtaggag | 240 |
| tcagcccatg cttttgctga ggggctatcc catgaggaat tcaggatgt gatgaggtct | 300 |
| tgagatcagc ccctcgtact ttgggacgca ccacgtcaga agccagacta aagaaaatag | 360 |
| ccagagactt gggccgagta gctatgttgc ctggtccccc tgggggcct tgttcacctt | 420 |
| gtctgcatgt agcttcatct tccccatcag aatccacaat aaaaacatat tctgctttga | 480 |
| agagatcacc tttctgcatt ccttgaggtt cctttgtatc gaattccttt tgttgtgaat | 540 |
| tcctcccact gacctctgac ggataatcca gtatcctctg gaccctctct tgtttgctct | 600 |
| cagagctgaa ggtcatatga tcactgtact caaacctatt tacagtttct ggactcttat | 660 |
| cagttggttc ctcgggaatt ttaacgagaa atttggaagt gtcagccaac tgaatgtggg | 720 |
| ttggtagtct tctgagagtg gggacaaatg tgaagatcag angtttggnn tcaggatctc | 780 |
| caggagagac cgtcactccc tcctctaagt tcttgntcct ctttagtgag cttcctgg | 838 |

<210> SEQ ID NO 55
<211> LENGTH: 895
<212> TYPE: DNA
<213> ORGANISM: Mus musculus
<220> FEATURE:
<221> NAME/KEY: misc_feature
<222> LOCATION: (862)..(862)
<223> OTHER INFORMATION: n = any nucleotide

<400> SEQUENCE: 55

| | |
|---|---|
| cacttccact ccagcttcct tactgctcag aaaacaggcc actgttgtct tcaaggtatt | 60 |
| tactgaaagg gttgggctca taaacttctt catcctttct caggagtagt ttggatttta | 120 |
| caggtactgg acgaattact ccaggcttag tcagttggct ctcagacgct gttgaggatg | 180 |
| atgaagaaag atttgcgtat ttggtttctc gaccagctgc tcttggatga gttgtaggag | 240 |

```
tcagcccatg cttttgctga ggggctatcc catgaggaat ttcaggatgt gatgaggtct    300
tgagatcagc ccctcgtact ttgggacgca ccacgtcaga agccagacta aagaaaatag    360
ccagagactt gggccgagta gctatgttgc ctggtccccc tgggggcct tgttcacctt     420 gtctgcatgt agcttcatct tccccatcag aatccacaat aaaaacatat tctgctttga    480
agagatcacc tttctgcatt ccttgaggtt cctttgtatt gaattccttt tgttgtgaat    540
tcctcccact gacctctgac ggataatcca gtatcctctg gaccctctct tgtttgctct    600
cagagctgaa ggtcatatga tcactgtact caaacctatt tacagtttct ggactcttat    660
cagttggttc ctcgggaatt ttaacgagaa atttggaagt gtcagccaac tgaatgtggg    720
ttggtagtct tctgagagtg gggacaaatg tgaagatcag aggtttggct tcaggatctc    780
caggagagac cgtcactccc tcctctaagt tcttgttcct cttagtgag cttcctggtt     840 catgctttcc aaattccatg gngaaagaat gagagagagg tagaaagaga cagaa         895
```

```
<210> SEQ ID NO 56
<211> LENGTH: 768
<212> TYPE: DNA
<213> ORGANISM: Mus musculus

<400> SEQUENCE: 56
tccattctgt ctcttctac ctctctctca ttctttcacc atggaatttg gaaagcatga      60
accaggaagc tcactaaaga ggaacaagaa cttagaggag ggagtgacgt ttgagtacag    120
tgatcatatg accttcagct ctgagagcaa acaagagagg gtccagagga tactggatta    180
tccgtcagag gtcagtggga ggaattcaca acaaaaggaa ttcaatacaa aggaacctca    240
aggaatgcag aaaggtgatc tcttcaaagc agaatatgtt tttattgtgg attctgatgg    300
ggaagatgaa gctacatgca gacaaggtga acaaggcccc caggggggac caggcaacat    360
agctactcgg cccaagtctc tggctatttc ttctagtctg gcttctgacg tggtgcgtcc    420
caaagtacga ggggctgatc tcaagacctc atcacatcct gaaattcctc atgggatagc    480
ccctcagcaa aagcatgggc tgcaatacaa gaccatgtca agctacaagg cttttgcagc    540
aatccctaca aacacattgc tcttggaaca gaagactcct acaactcatc caagagcagc    600
tggtcgagaa accaaatacg caaatctttc ttcatcatcc tcaacagcgt ctgagagcca    660
actgactaag cctggagtaa ttcgtccagt acctgtaaaa tccaaactac tcctgagaaa    720
ggatgaagaa gtttatgagc ccaacccttt cagtaaatac cttgaaga                 768
```

```
<210> SEQ ID NO 57
<211> LENGTH: 1298
<212> TYPE: DNA
<213> ORGANISM: Mus musculus

<400> SEQUENCE: 57
atcgccaggg cttctgatat cgtcctaggc tcttacaacg tggaatgccc ggcattatct     60
aacacgcaag catgtcaaat cagtttctag acagaatctg gacccctctc tcttccattc    120
tgtctctttc tacctctctc tcattctttc accatggaat ttggaaagca tgaaccagga    180
agctcactaa agaggaacaa gaacttagag gagggagtga cggtctctcc tggagatcct    240
gaagccaaac ctctgatctt cacatttgtc cccactctca aagactacc aacccacatt    300 cagttggctg acacttccaa atttctcgtt aaaattcccg aggaaccaac tgataagagt    360
ccagaaactg taaataggtt tgagtacagt gatcatatga ccttcagctc tgagagcaaa    420
caagagaggg tccagaggat actggattat ccgtcagagg tcagtgggag gaattcacaa    480
```

```
caaaaggaat tcaatacaaa ggaacctcaa ggaatgcaga aagtgatctc cttcaaagca      540
gaatatgttt ttattgtgga ttctgatggg gaagatgaag ctacatgcag acaaggtgaa      600
caaggccccc caggggggacc aggcaacata gctactcggc ccaagtctct ggctatttct     660
tctagtctgg cttctgacgt ggtgcgtccc aaagtacgag gggctgatct caagacctca      720
tcacatcctg aaattcctca tgggatagcc cctcagcaaa agcatgggct gactcctaca      780
actcatccaa gagcagctgg tcgagaaacc aaatacgcaa atctttcttc atcatcctca      840
acagcgtctg agagccaact gactaagcct ggagtaattc gtccagtacc tgtaaaatcc      900
aaactactcc tgagaaagga tgaagaagtt tatgagccca ccctttcag taaatacctt      960 gaagacaaca gtggcctgtt ttctgagcag taaggaagct ggagtggaag tggacaccgg     1020
tctgctgaag agtttggaa tgatgccatg gccaactact tgctaaactt acctgatgct      1080
ttgttagaag gagtgctctg ctcagtccag cagaagcacc tgaatggttt gccacagcca     1140
catagcatta ccacactctg ggaaacccag agcaggatca tagcccttct gtttcttgca     1200
ttgccgttca agcctataat gccttctatt aagtcaacag caatactaat gttcccctat     1260
atttagcagt caaataaaga agaatgatag ctgaatac                             1298

<210> SEQ ID NO 58
<211> LENGTH: 316
<212> TYPE: DNA
<213> ORGANISM: Mus musculus
<220> FEATURE:
<221> NAME/KEY: misc_feature
<222> LOCATION: (9)..(9)
<223> OTHER INFORMATION: n = any nucleotide
<220> FEATURE:
<221> NAME/KEY: misc_feature
<222> LOCATION: (80)..(81)
<223> OTHER INFORMATION: n = any nucleotide

<400> SEQUENCE: 58
caggccacng ttgtcttcaa ggtatttact gaaagggttg ggctcataaa cttcttcatc       60 cttttctcagg agtagtttgn nttttacagg tactggacga attactccag gcttagtcag     120
ttggttctca gacgctgttg aggatgatga agaaagattt gcgtatttgg tttctcgacc     180
agctgctctt ggatgagttg taggagtcgt cactccctcc tctaagttct tgttcctctt     240
tagtgagctt cctggttcat gctttccaaa ttccatggtg aaagaatgag agagaggtag     300
aaagagacag aatgga                                                     316

<210> SEQ ID NO 59
<211> LENGTH: 345
<212> TYPE: DNA
<213> ORGANISM: Mus musculus

<400> SEQUENCE: 59
tccattctgt ctctttctac ctctctctca ttctttcacc atggaatttg gaaagcatga      60
accaggaagc tcactaaaga ggaacaagaa cttagaggag ggagactcct acaactcatc     120
caagagcagc tggtcgagaa accaaatacg caaatctttc ttcatcatcc tcaacagcgt     180
ctgagaacca actgactaag cctggagtaa ttcgtccagt acctgtaaaa tccaaactac     240
tcctgagaaa ggatgaagaa gtttatgagc ccaacccttt cagtaaatac cttgaagaca     300
acagtggcct gttttctgag cagtaaggaa gctggagtgg aagtg                     345

<210> SEQ ID NO 60
<211> LENGTH: 350
<212> TYPE: DNA
```

<213> ORGANISM: Mus musculus

<400> SEQUENCE: 60

| | | | | | |
|---|---|---|---|---|---|
| tccattctgt | ctctttctac | ctctctctca | ttctttcacc | atggaatttg gaaagcatga | 60 |
| accaggaagc | tcactaaaga | ggaacaagaa | cttagaggag | ggagtgacga ctcctacaac | 120 |
| tcatccaaga | gcagctggtc | gagaaaccaa | atacgcaaat | cttcttcat catcctcaac | 180 |
| agcgtctgag | agccaactga | ctaagcctgg | agtaattcgt | ccagtacctg taaaatccaa | 240 |
| actactcctg | agaaaggatg | aagaagttta | tgagcccaac | cctttcagta aataccttga | 300 |
| agacaacagt | ggcctgtttt | ctgagcagta | aggaagctgg | agtggaagtg | 350 |

<210> SEQ ID NO 61
<211> LENGTH: 713
<212> TYPE: DNA
<213> ORGANISM: Mus musculus
<220> FEATURE:
<221> NAME/KEY: misc_feature
<222> LOCATION: (712)..(712)
<223> OTHER INFORMATION: n = any nucleotide

<400> SEQUENCE: 61

| | | | | | |
|---|---|---|---|---|---|
| aaaacaggcc | actgttgtct | tcaaggtatt | tactgaaagg | gttgggctca taaacttctt | 60 |
| catcctttct | caggagtagt | ttggatttta | caggtactgg | acgaattact ccaggcttag | 120 |
| tcagttggct | ctcagacgct | gttgaggatg | atgaagaaag | atttgcgtat ttggtttctc | 180 |
| gaccagctgc | tcttggatga | gttgtaggag | tcagcccatg | cttttgctga ggggctatcc | 240 |
| catgaggaat | tcaggatgt | gatgaggtct | tgagatcagc | cctcgtact tgggacgca | 300 |
| ccacgtcaga | agccagacta | gaagaaatag | ccagagactt | gggccgagta gctatgttgc | 360 |
| ctggtccccc | tgggggcct | tgttcacctt | gtctgcatgt | agcttcatct tccccatcag | 420 |
| aatccacaat | aaaacatat | tctgctttga | agagatcacc | tttctgcatt ccttgaggtt | 480 |
| cctttgtatt | gaattccttt | tgttgtgaat | tcctcccact | gacctctgac ggataatcca | 540 |
| gtatcctctg | gaccctctct | tgtttgctct | cagagctgaa | ggtcatatga tcactgtact | 600 |
| caaacgtcac | tccctcctct | aagttcttgt | tcctctttag | tgagcttcct ggttcatgct | 660 |
| ttccaaattc | catggtgaaa | gaatgagaga | gaggtagaaa | gagacagaat gna | 713 |

<210> SEQ ID NO 62
<211> LENGTH: 393
<212> TYPE: DNA
<213> ORGANISM: Mus musculus

<400> SEQUENCE: 62

| | | | | | |
|---|---|---|---|---|---|
| gtttgagtac | agtgatcata | tgaccttcag | ctctgagagc | aaacaagaga gggtccagag | 60 |
| gatactggat | tatccgtcag | aggtcagtgg | gaggaattca | caacaaaagg aattcaatac | 120 |
| aaaggaacct | caaggaatgc | agaaaggtga | tctcttcaaa | gcagaatatg tttttattgh | 180 |
| ggattctgat | ggggaagatg | aagctacatg | cagacaaggt | gaacaaggcc ccccaggggg | 240 |
| accaggcaac | atagctactc | ggcycaagtc | tctggctatt | tcttctagtc tggcttctga | 300 |
| cgtggtgcgt | cccaaagtac | gagggggctga | tctcaagacc | tcatcacatc ctgaaattcc | 360 |
| tcatgggata | gcccctcagc | aaaagcatgg | gct | | 393 |

<210> SEQ ID NO 63
<211> LENGTH: 72
<212> TYPE: DNA
<213> ORGANISM: Mus musculus

<400> SEQUENCE: 63

```
gcaatacaag accatgtcaa gctacaaggc ttttgcagca atccctacaa acacattgct      60
cttggaacag aa                                                         72
```

<210> SEQ ID NO 64
<211> LENGTH: 733
<212> TYPE: DNA
<213> ORGANISM: Mus musculus
<220> FEATURE:
<221> NAME/KEY: misc_feature
<222> LOCATION: (73)..(74)
<223> OTHER INFORMATION: n = any nucleotide
<220> FEATURE:
<221> NAME/KEY: misc_feature
<222> LOCATION: (728)..(728)
<223> OTHER INFORMATION: n = any nucleotide

<400> SEQUENCE: 64

```
ctctttctac ctctctctca ttctttcacc atggaatttg gaaagcatga accaggaagc      60
tcactaaaga ggnncaagaa cttagaggag ggagtgacgt ttgagtacag tgatcatatg     120
accttcagct ctgagagcaa acaagagagg gtccagagga tactggatta ccgtcagag      180
gtcagtggga ggaattcaca acaaaaggaa ttcaatacaa aggaacctca aggaatgcag     240
aaaggtgatc tcttcaaagc agaatatgtt tttattgcgg attctgatgg ggaagatgaa     300
gctacatgca gacaaggtga acaaggcccc ccaggggac caggcaacat agctactcgg     360
ctcaagtctc tggctatttc ttctagtctg gcttctgacg tggtgcgtcc caaagtacga     420
ggggctgatc tcaagacctc atcacatcct gaaattcctc atgggatagc ccctcagcaa     480
aagcatgggc tgactcctac aactcatcca agagcagctg gtcgagaaac caaatacgca     540
aatctttctt catcatcctc aacagcgtct gagagccaac tgactaagcc tggagtaatt     600
cgtccagtac ctgtaaaatc caaactactc ctgagaaagg acgaagaagt ttatgagccc     660
aacccttca gtaaatacct tgaagacaac agtggcctgt tttctgagca gtaaggaagc     720
tggagtgnaa gtg                                                         733
```

<210> SEQ ID NO 65
<211> LENGTH: 126
<212> TYPE: DNA
<213> ORGANISM: Mus musculus

<400> SEQUENCE: 65

```
actaagcctg gagtaattcg tccagtacct gtaaaatcca aactactcct gagaaaggay      60
gaagaagttt atgagcccaa ccctttcagt aaataccttg aagacaacag tggcctgttt     120
tctgag                                                                126
```

<210> SEQ ID NO 66
<211> LENGTH: 350
<212> TYPE: DNA
<213> ORGANISM: Mus musculus

<400> SEQUENCE: 66

```
cacttccact ccagcttcct tactgctcag aaaacaggcc actgttgtct tcaaggtatt      60
tactgaaagg gttgggctca taaacttctt catcctttct caggagtagt ttggatttta     120
caggtactgg acgaattact ccaggcttag tcagttggct ctcagacgct gttgaggatg     180
atgaagaaag atttgcgtat ttggtttctc gaccagctgc tcttggatga gttgtaggag     240
tcgtcactcc ctcctctaag ttcttgttcc tctttagtga gcttcctggt tcatgctttc     300
```

```
caaattccat ggtgaaagaa tgagagagag gtagaaagag acagaatgga            350
```

<210> SEQ ID NO 67
<211> LENGTH: 47
<212> TYPE: DNA
<213> ORGANISM: Mus musculus

<400> SEQUENCE: 67

```
gactcctaca actcatccaa gagcagctgg tcgagaaacc aaatacg              47
```

<210> SEQ ID NO 68
<211> LENGTH: 44
<212> TYPE: DNA
<213> ORGANISM: Mus musculus

<400> SEQUENCE: 68

```
caaatctttc ttcatcatcc tcaacagcgt ctgagagcca actg                 44
```

<210> SEQ ID NO 69
<211> LENGTH: 81
<212> TYPE: DNA
<213> ORGANISM: Mus musculus
<220> FEATURE:
<221> NAME/KEY: misc_feature
<222> LOCATION: (26)..(26)
<223> OTHER INFORMATION: n = any nucleotide
<220> FEATURE:
<221> NAME/KEY: misc_feature
<222> LOCATION: (31)..(31)
<223> OTHER INFORMATION: n = any nucleotide
<220> FEATURE:
<221> NAME/KEY: misc_feature
<222> LOCATION: (36)..(36)
<223> OTHER INFORMATION: n = any nucleotide
<220> FEATURE:
<221> NAME/KEY: misc_feature
<222> LOCATION: (46)..(46)
<223> OTHER INFORMATION: n = any nucleotide
<220> FEATURE:
<221> NAME/KEY: misc_feature
<222> LOCATION: (52)..(52)
<223> OTHER INFORMATION: n = any nucleotide
<220> FEATURE:
<221> NAME/KEY: misc_feature
<222> LOCATION: (76)..(76)
<223> OTHER INFORMATION: n = any nucleotide

<400> SEQUENCE: 69

```
ctcactaaag aggaacaaga acttanagga nggagngacg tctgantaca gngatcatat   60
gaccttcagc tctganagca a                                            81
```

<210> SEQ ID NO 70
<211> LENGTH: 577
<212> TYPE: DNA
<213> ORGANISM: Mus musculus
<220> FEATURE:
<221> NAME/KEY: misc_feature
<222> LOCATION: (558)..(558)
<223> OTHER INFORMATION: n = any nucleotide
<220> FEATURE:
<221> NAME/KEY: misc_feature
<222> LOCATION: (570)..(570)
<223> OTHER INFORMATION: n = any nucleotide

<400> SEQUENCE: 70

```
tccattctgt ctctttctac ctctctctca ttctttcacc atggaatttg gaaagcatga   60
accaggaagc tcactaaaga ggaacaagaa cttagaggag ggagtgacgg tctctcctgg  120
agatcctgaa gccaaacctc tgatcttcac atttgtcccc actctcagaa gactaccaac  180
```

-continued

| | |
|---|---|
| ccacattcag ttggctgaca cttccaaatt tctcgttaaa attcccgagg aaccaactga | 240 |
| taagagtcca gaaactgtaa ataggtttga gtacagtgat catatgacct tcagctctga | 300 |
| gagcaaacaa gagagggtcc agaggatact ggattatccg tcagaggtca gtgggaggaa | 360 |
| ttcacaacaa aaggaattcg atacaaagga acctcaagga atgcagaaag gtgatctctt | 420 |
| caaagcagaa tatgttttta ttgtggattc tgatggggaa gatgaagcta catgcagaca | 480 |
| aggtgaacaa ggcccccccag ggggaccagg caacatagct actcggccca agtctctggc | 540 |
| tatttcttct agtctggntt ctgacgtggn gcgtccc | 577 |

<210> SEQ ID NO 71
<211> LENGTH: 68
<212> TYPE: DNA
<213> ORGANISM: Mus musculus

<400> SEQUENCE: 71

| | |
|---|---|
| atggaatttg gaaagcatga accaggaagc tcactaaaga ggaacaagaa cttagaggag | 60 |
| ggagtgac | 68 |

<210> SEQ ID NO 72
<211> LENGTH: 156
<212> TYPE: DNA
<213> ORGANISM: Mus musculus

<400> SEQUENCE: 72

| | |
|---|---|
| ggtctctcct ggagatcctg aagccaaacc tctgatcttc acatttgtcc ccactctcag | 60 |
| aagactacca acccacattc agttggctga cacttccaaa tttctcgtta aaattcccga | 120 |
| ggaaccaact gataagagtc cagaaactgt aaatag | 156 |

<210> SEQ ID NO 73
<211> LENGTH: 743
<212> TYPE: DNA
<213> ORGANISM: Mus musculus

<400> SEQUENCE: 73

| | |
|---|---|
| cacttccact ccagcttcct tactgctcag aaaacaggcc actgttgtct tcaaggtatt | 60 |
| tactgaaagg gttgggctca taaacttctt catcctttct caggagtagt ttggatttta | 120 |
| caggtactgg acgaattact ccaggcttag tcagttggct ctcagacgct gttgaggatg | 180 |
| atgaagaaag atttgcgtat ttggtttctc gaccagctgc tcttggatga gttgtaggag | 240 |
| tcagcccatg cttttgctga ggggctatcc catgaggaat tcaggatgt gatgaggtct | 300 |
| tgagatcagc ccctcgtact ttgggacgca ccacgtcaga agccagacta aagaaatag | 360 |
| ccagagactt gggccgagta gctatgttgc ctggtccccc tggggggcct tgttcacctt | 420 |
| gtctgcatgt agcttcatct tccccatcag aatcctcaat aaaaacatat tctgctttga | 480 |
| agagatcacc tttctgcatt ccttgaggtt cctttgtatt gaattccttt tgttgtgaat | 540 |
| tcctcccact gacctctgac ggataatcca gtatcctctg gaccctctct tgtttgctct | 600 |
| cagagctgaa ggtcatatga tcactgtact caaacgtcac tccctcctct aagttcttgt | 660 |
| tcctctttag tgagcttcct ggttcatgct ttccaaattc catggtgaaa gaatgagaga | 720 |
| gaggtagaaa gagacagaat gga | 743 |

<210> SEQ ID NO 74
<211> LENGTH: 815
<212> TYPE: DNA
<213> ORGANISM: Mus musculus

<400> SEQUENCE: 74

```
cacttccact ccagcttcct tactgctcag aaaacaggcc actgttgtct tcaaggtatt      60
tactgaaagg gttgggctca taaacttctt catcctttct caggagtagt ttggatttta     120
caggtactgg acgaattact ccaggcttag tcagttggct ctcagacgct gttgaggatg     180
atgaagaaag atttgcgtat ttggtttctc gaccagctgc tcttggatga gttgtaggag     240
tcttctgttc aagagcaat gtgtttgtag ggattgctgc aaaagccttg tagcttgaca     300
tggtcttgta ttgcagccca tgcttttgct gagggctat cccatgagga atttcaggat     360
gtgatgaggt cttgagatca gcccctcgta ctttgggacg caccacgtca gaagccagac     420
tagaagaaat agccagagac ttgggccgag tagctatgtt gcctggtccc cctgggggc     480
cttgttcacc ttgtctgcat gtagcttcat cttccccatc agaatccaca ataaaaacat     540
attctgcttt gaagagatca cctttctgca ttccttgagg ttcctttgta ttgaattcct     600
tttgttgtga attcctccca ctgacctctg acggataatc cagtatcctc tggaccctct     660
cttgtttgct ctcagagctg aaggtcatat gatcactgta ctcagacgtc actccctcct     720
ctaagttctt gttcctcttt agtgagcttc ctggttcatg ctttccaaat tccatggtga     780
aagaatgaga gagaggtaga aagagacaga atgga                                 815
```

<210> SEQ ID NO 75
<211> LENGTH: 458
<212> TYPE: PRT
<213> ORGANISM: Homo sapiens

<400> SEQUENCE: 75

```
Met Glu Leu Glu Lys Arg Glu Lys Arg Ser Leu Leu Asn Lys Asn Leu
 1               5                  10                  15

Glu Glu Lys Leu Thr Val Ser Ala Gly Gly Ser Glu Ala Lys Pro Leu
            20                  25                  30

Ile Phe Thr Phe Val Pro Thr Val Arg Arg Leu Pro Thr His Thr Gln
        35                  40                  45

Leu Ala Asp Thr Ser Lys Phe Leu Val Lys Ile Pro Glu Glu Ser Ser
    50                  55                  60

Asp Lys Ser Pro Glu Thr Val Asn Arg Ser Lys Ser Asn Asp Tyr Leu
65                  70                  75                  80

Thr Leu Asn Ala Gly Ser Gln Gln Glu Arg Asp Gln Ala Lys Leu Thr
                85                  90                  95

Cys Pro Ser Glu Val Ser Gly Thr Ile Leu Gln Glu Arg Glu Phe Glu
           100                 105                 110

Ala Asn Lys Leu Gln Gly Met Gln Gln Ser Asp Leu Phe Lys Ala Glu
       115                 120                 125

Tyr Val Leu Ile Val Asp Ser Glu Gly Glu Asp Glu Ala Ala Ser Arg
   130                 135                 140

Lys Val Glu Gln Gly Pro Pro Gly Gly Ile Gly Thr Ala Ala Ile Arg
145                 150                 155                 160

Pro Lys Ser Leu Ala Ile Ser Ser Leu Val Ser Asp Val Val Arg
               165                 170                 175

Pro Lys Thr Gln Gly Thr Asp Leu Lys Thr Ser Ser His Pro Glu Met
           180                 185                 190

Leu His Gly Met Ala Pro Gln Gln Lys His Gly Gln Gln Tyr Lys Thr
       195                 200                 205

Lys Ser Ser Tyr Lys Ala Phe Ala Ala Ile Pro Thr Asn Thr Leu Leu
   210                 215                 220
```

Leu Glu Gln Lys Ala Leu Asp Glu Pro Ala Lys Thr Glu Ser Val Ser
225                 230                 235                 240

Lys Asp Asn Thr Leu Glu Pro Pro Val Glu Leu Tyr Phe Pro Ala Gln
            245                 250                 255

Leu Arg Gln Gln Thr Glu Glu Leu Cys Ala Thr Ile Asp Lys Val Leu
        260                 265                 270

Gln Asp Ser Leu Ser Met His Ser Ser Asp Ser Pro Ser Arg Ser Pro
    275                 280                 285

Lys Thr Leu Leu Gly Ser Asp Thr Val Lys Thr Pro Thr Thr Leu Pro
290                 295                 300

Arg Ala Ala Gly Arg Glu Thr Lys Tyr Ala Asn Leu Ser Ser Pro Thr
305                 310                 315                 320

Ser Thr Val Ser Glu Ser Gln Leu Thr Lys Pro Gly Val Ile Arg Pro
                325                 330                 335

Val Pro Val Lys Ser Arg Ile Leu Leu Lys Glu Glu Val Tyr
            340                 345                 350

Glu Pro Asn Pro Phe Ser Lys Tyr Leu Glu Asp Asn Ser Asp Leu Phe
                355                 360                 365

Ser Glu Gln Asp Val Thr Val Pro Pro Lys Pro Val Ser Leu His Pro
    370                 375                 380

Leu Tyr Gln Thr Lys Leu Tyr Pro Pro Ala Lys Ser Leu Leu His Pro
385                 390                 395                 400

Gln Thr Leu Ser His Ala Asp Cys Leu Ala Pro Gly Pro Phe Ser His
                405                 410                 415

Leu Ser Phe Ser Leu Ser Asp Glu Gln Glu Asn Ser His Thr Leu Leu
                420                 425                 430

Ser His Asn Ala Cys Asn Lys Leu Ser His Pro Met Val Ala Ile Pro
    435                 440                 445

Glu His Glu Ala Leu Asp Ser Lys Glu Gln
    450                 455

<210> SEQ ID NO 76
<211> LENGTH: 234
<212> TYPE: PRT
<213> ORGANISM: Homo sapiens

<400> SEQUENCE: 76

Met Cys Ser Trp Tyr Leu Gly Phe Glu Cys Ser Ser Lys Ser Asn Asp
1               5                   10                  15

Tyr Leu Thr Leu Asn Ala Gly Ser Gln Gln Glu Arg Asp Gln Ala Lys
            20                  25                  30

Leu Thr Cys Pro Ser Glu Val Ser Gly Thr Ile Leu Gln Glu Arg Glu
        35                  40                  45

Phe Glu Ala Asn Lys Leu Gln Gly Met Gln Gln Ser Asp Leu Phe Lys
    50                  55                  60

Ala Glu Tyr Val Leu Ile Val Asp Ser Glu Gly Glu Asp Glu Ala Ala
65                  70                  75                  80

Ser Arg Lys Val Glu Gln Gly Pro Pro Gly Gly Ile Gly Thr Ala Ala
                85                  90                  95

Ile Arg Pro Lys Ser Leu Ala Ile Ser Ser Ser Leu Val Ser Asp Val
            100                 105                 110

Val Arg Pro Lys Thr Gln Gly Thr Asp Leu Lys Thr Ser Ser His Pro
        115                 120                 125

Glu Met Leu His Gly Met Ala Pro Gln Gln Lys His Gly Gln Thr Pro
    130                 135                 140

```
Thr Thr Leu Pro Arg Ala Ala Gly Arg Glu Thr Lys Tyr Ala Asn Leu
145                 150                 155                 160

Ser Ser Pro Thr Ser Thr Val Ser Glu Ser Gln Leu Thr Lys Pro Gly
            165                 170                 175

Val Ile Arg Pro Val Pro Val Lys Ser Arg Ile Leu Leu Lys Lys Glu
        180                 185                 190

Glu Glu Val Tyr Glu Pro Thr Pro Phe Ser Lys Tyr Leu Glu Asp Asn
            195                 200                 205

Ser Asp Leu Phe Ser Glu Gln Leu Ser His Pro Met Val Ala Ile Pro
210                 215                 220

Glu His Glu Ala Leu Asp Ser Lys Glu Gln
225                 230
```

<210> SEQ ID NO 77
<211> LENGTH: 458
<212> TYPE: PRT
<213> ORGANISM: Homo sapiens

<400> SEQUENCE: 77

```
Met Glu Leu Glu Lys Arg Glu Lys Arg Ser Leu Leu Asn Lys Asn Leu
1               5                   10                  15

Glu Glu Lys Leu Thr Val Ser Ala Gly Gly Ser Glu Ala Lys Pro Leu
            20                  25                  30

Ile Phe Thr Phe Val Pro Thr Arg Arg Leu Pro Thr His Thr Gln
            35                  40                  45

Leu Ala Asp Thr Ser Lys Phe Leu Val Lys Ile Pro Glu Glu Ser Ser
    50                  55                  60

Asp Lys Ser Pro Glu Thr Val Asn Arg Ser Lys Ser Asn Asp Tyr Leu
65                  70                  75                  80

Thr Leu Asn Ala Gly Ser Gln Gln Glu Arg Asp Gln Ala Lys Leu Thr
                85                  90                  95

Cys Pro Ser Glu Val Ser Gly Thr Ile Leu Gln Glu Arg Glu Phe Glu
            100                 105                 110

Ala Asn Lys Leu Gln Gly Met Gln Gln Ser Asp Leu Phe Lys Ala Glu
        115                 120                 125

Tyr Val Leu Ile Val Asp Ser Glu Gly Glu Asp Glu Ala Ala Ser Arg
130                 135                 140

Lys Val Glu Gln Gly Pro Gly Gly Ile Gly Thr Ala Ala Ile Arg
145                 150                 155                 160

Pro Lys Ser Leu Ala Ile Ser Ser Ser Leu Val Ser Asp Val Val Arg
                165                 170                 175

Pro Lys Thr Gln Gly Thr Asp Leu Lys Thr Ser Ser His Pro Glu Met
            180                 185                 190

Leu His Gly Met Ala Pro Gln Gln Lys His Gly Gln Gln Tyr Lys Thr
        195                 200                 205

Lys Ser Ser Tyr Lys Ala Phe Ala Ala Ile Pro Thr Asn Thr Leu Leu
    210                 215                 220

Leu Glu Gln Lys Ala Leu Asp Glu Pro Ala Lys Thr Glu Ser Val Ser
225                 230                 235                 240

Lys Asp Asn Thr Leu Glu Pro Pro Val Glu Leu Tyr Phe Pro Ala Gln
                245                 250                 255

Leu Arg Gln Gln Thr Glu Glu Leu Cys Ala Thr Ile Asp Lys Val Leu
            260                 265                 270

Gln Asp Ser Leu Ser Met His Ser Ser Asp Ser Pro Arg Ser Pro
        275                 280                 285
```

```
Lys Thr Leu Leu Gly Ser Asp Thr Val Lys Thr Pro Thr Thr Leu Pro
        290                 295                 300

Arg Ala Ala Gly Arg Glu Thr Lys Tyr Ala Asn Leu Ser Ser Pro Thr
305                 310                 315                 320

Ser Thr Val Ser Glu Ser Gln Leu Thr Lys Pro Gly Val Ile Arg Pro
                325                 330                 335

Val Pro Val Lys Ser Arg Ile Leu Leu Lys Glu Glu Val Tyr
                340                 345                 350

Glu Pro Asn Pro Phe Ser Lys Tyr Leu Glu Asp Asn Ser Asp Leu Phe
                355                 360                 365

Ser Glu Gln Asp Val Thr Val Pro Pro Lys Pro Val Ser Leu His Pro
    370                 375                 380

Leu Tyr Gln Thr Lys Leu Tyr Pro Pro Ala Lys Ser Leu Leu His Pro
385                 390                 395                 400

Gln Thr Leu Ser His Ala Asp Cys Leu Ala Pro Gly Pro Phe Ser His
                405                 410                 415

Leu Ser Phe Ser Leu Ser Asp Glu Gln Asn Ser His Thr Leu Leu
                420                 425                 430

Ser His Asn Ala Cys Asn Lys Leu Ser His Pro Met Val Ala Ile Pro
                435                 440                 445

Glu His Glu Ala Leu Asp Ser Lys Glu Gln
    450                 455

<210> SEQ ID NO 78
<211> LENGTH: 162
<212> TYPE: PRT
<213> ORGANISM: Homo sapiens

<400> SEQUENCE: 78

Met Gln Gln Ser Asp Leu Phe Lys Ala Glu Tyr Val Leu Ile Val Asp
1               5                   10                  15

Ser Glu Gly Glu Asp Glu Ala Ala Ser Arg Lys Val Gln Gly Pro
                20                  25                  30

Pro Gly Gly Ile Gly Thr Ala Ala Val Arg Pro Lys Ser Leu Ala Ile
            35                  40                  45

Ser Ser Ser Leu Val Ser Asp Val Val Arg Pro Lys Thr Gln Gly Thr
    50                  55                  60

Asp Leu Lys Thr Ser Ser His Pro Glu Met Leu His Gly Met Ala Pro
65                  70                  75                  80

Gln Gln Lys His Gly Gln Gln Tyr Lys Thr Lys Ser Ser Tyr Lys Ala
                85                  90                  95

Phe Ala Ala Ile Pro Thr Asn Thr Leu Leu Leu Glu Gln Lys Ala Leu
                100                 105                 110

Asp Glu Pro Ala Lys Thr Glu Ser Val Ser Lys Asp Asn Thr Leu Glu
            115                 120                 125

Pro Pro Val Glu Thr Pro Thr Leu Pro Arg Ala Ala Gly Arg Glu
        130                 135                 140

Thr Lys Tyr Ala Asn Leu Ser Ser Pro Ser Ser Thr Val Ser Glu Ser
145                 150                 155                 160

Gln Leu

<210> SEQ ID NO 79
<211> LENGTH: 178
<212> TYPE: PRT
<213> ORGANISM: Homo sapiens

<400> SEQUENCE: 79
```

```
Met Gln Gln Ser Asp Leu Phe Lys Ala Glu Tyr Val Leu Ile Val Asp
1               5                   10                  15

Ser Glu Gly Glu Asp Glu Ala Ala Ser Arg Lys Val Glu Gln Gly Pro
            20                  25                  30

Pro Gly Gly Ile Gly Thr Ala Ala Val Arg Pro Lys Ser Leu Ala Ile
            35                  40                  45

Ser Ser Ser Leu Val Ser Asp Val Val Arg Pro Lys Thr Gln Gly Thr
        50                  55                  60

Asp Leu Lys Thr Ser Ser His Pro Glu Met Leu His Gly Met Ala Pro
65                  70                  75                  80

Gln Gln Lys His Gly Gln Thr Pro Thr Thr Leu Pro Arg Ala Ala Gly
                85                  90                  95

Arg Glu Thr Lys Tyr Ala Asn Leu Ser Ser Pro Ser Ser Thr Val Ser
                100                 105                 110

Glu Ser Gln Leu Thr Lys Pro Gly Val Ile Arg Pro Val Pro Val Lys
            115                 120                 125

Ser Arg Ile Leu Leu Lys Lys Glu Glu Val Tyr Glu Pro Asn Pro
        130                 135                 140

Phe Ser Lys Tyr Leu Glu Asp Asn Ser Asp Leu Phe Ser Glu Gln Leu
145                 150                 155                 160

Ser His Pro Met Val Ala Ile Pro Glu His Glu Ala Leu Asp Ser Lys
                165                 170                 175

Glu Gln
```

<210> SEQ ID NO 80
<211> LENGTH: 504
<212> TYPE: DNA
<213> ORGANISM: Homo sapiens
<220> FEATURE:
<221> NAME/KEY: misc_feature
<222> LOCATION: (489)..(491)
<223> OTHER INFORMATION: n = any nucleotide
<220> FEATURE:
<221> NAME/KEY: misc_feature
<222> LOCATION: (493)..(494)
<223> OTHER INFORMATION: n = any nucleotide
<220> FEATURE:
<221> NAME/KEY: misc_feature
<222> LOCATION: (501)..(504)
<223> OTHER INFORMATION: n = any nucleotide

<400> SEQUENCE: 80

```
gactaagcct ggagtaattc gcccagtacc tgtaaaatcc agaatattac tgaaaaaaga      60
ggaggaagtc tatgaaccca acccttcag taaatacttg aagataaca gcgacctctt      120 ttctgaacag gatgtaacag tccctcccaa gcctgtctcg ctccatcctt tatatcagac    180
taaactctat cctcctgcta agtcactgct gcatccacag accctctcac atgctgactg    240
tcttgcccca ggacccttca gtcatctgtc cttctccttg agtgatgaac aggagaattc    300
tcacaccctc ctcagtcaca acgcatgcaa caagctgagt catccaatgg tggctattcc    360
tgaacatgaa gctcttgatt ccaaagagca atgaagttgg agcagaggca agggcgaatt    420
ccagcacact ggcggccgtt actagtggat ccgagctcgg taccaagctt ggcgtaatca    480
tggtcatann ngnnttcctg nnnn                                            504
```

<210> SEQ ID NO 81
<211> LENGTH: 504
<212> TYPE: DNA
<213> ORGANISM: Homo sapiens
<220> FEATURE:

```
<221> NAME/KEY: misc_feature
<222> LOCATION: (489)..(493)
<223> OTHER INFORMATION: n = any nucleotide
<220> FEATURE:
<221> NAME/KEY: misc_feature
<222> LOCATION: (486)..(486)
<223> OTHER INFORMATION: n = any nucleotide
<220> FEATURE:
<221> NAME/KEY: misc_feature
<222> LOCATION: (501)..(504)
<223> OTHER INFORMATION: n = any nucleotide

<400> SEQUENCE: 81
gactaagcct ggagtaattc gcccagtacc tgtaaaatcc agaatattac tgaaaaaaga      60
ggaggaagtc tatgaaccca acccttcag taaatactta gaagataaca gcgacctctt     120
ttctgaacag gatgtaacag tccctcccaa gcctgtctcg ctccatcctt tatatcagac    180
taaactctat cctcctgcta agtcactgct gcatccacag accctctcac atgctgactg    240
tcttgcccca ggacccttca gtcatctgtc cttctccttg agtgatgaac aggagaattc    300
tcacaccctc ctcagtcaca acgcatgcaa caagctgagt catccaatgg tggctattcc    360
tgaacatgaa gctcttgatt ccaaagagca atgaagttgg agcagaggca agggcgaatt    420
ccagcacact ggcggccgtt actagtggat ccgagctcgg taccaagctt ggcgtaatca    480
tggtcntann nnntttcctg nnnn                                           504

<210> SEQ ID NO 82
<211> LENGTH: 500
<212> TYPE: DNA
<213> ORGANISM: Homo sapiens
<220> FEATURE:
<221> NAME/KEY: misc_feature
<222> LOCATION: (64)..(64)
<223> OTHER INFORMATION: n = any nucleotide
<220> FEATURE:
<221> NAME/KEY: misc_feature
<222> LOCATION: (489)..(490)
<223> OTHER INFORMATION: n = any nucleotide
<220> FEATURE:
<221> NAME/KEY: misc_feature
<222> LOCATION: (493)..(493)
<223> OTHER INFORMATION: n = any nucleotide

<400> SEQUENCE: 82
gactaagcct ggagtaattc gcccagtacc tgtaaaatcc agaatattac tgaaaaaaga      60
ggangaagtc tatgaaccca acccttcag taaatacttg aagataaca gcgacctctt      120
ttctgaacag gatgtaacag tccctcccaa gcctgtctcg ctccatcctt tatatcagac    180
taaactctat cctcctgcta agtcactgct gcatccacag accctctcac atgctgactg    240
tcttgcccca ggacccttca gtcatctgtc cttctccttg agtgatgaac aggagaattc    300
tcacaccctc ctcagtcaca acgcatgcaa caagctgagt catccaatgg tggctattcc    360
tgaacatgaa gctcttgatt ccaaagagca atgaagttgg agcagaggca agggcgaatt    420
ccagcacact ggcggccgtt actagtggat ccgagctcgg taccaagctt ggcgtaatca    480
tggtcatann tgntttcctg                                                500

<210> SEQ ID NO 83
<211> LENGTH: 1133
<212> TYPE: DNA
<213> ORGANISM: Homo sapiens

<400> SEQUENCE: 83
tctctttctc attctctttc aatatggaac ttgaaaagcg tgaaaaaaga agcttattaa      60
```

```
acaagaattt agaggagaaa ctgacggtct ctgctggtgg ytctgaagcc aaacctctga    120
tcttcacatt tgtccccact gtcagaagac taccaaccca tactcagttg gctgacacct    180
ctaaattcct tgttaaaatt ccagaagaat caagtgataa gagtccagaa actgtaaata    240
ggtctaaatc caatgactac ttgaccttga atgctgggag ccaacaagag agagaccaag    300
cgaaattgac ttgtccttca gaggtcagtg aacgattttt acaagaaagg gaattcgaag    360
caaacaaact tcaagggatg cagcaaagtg acctcttcaa agctgaatat gtccttattg    420
tggactccga aggggaagat gaggctgcaa gcagaaaagt tgaacaaggc cccccagggg    480
ggattggcac cgcagctatc cggcccaagt ctctagctat ctcgtccagt ctggtctctg    540
atgtagtgcg tcccaaaaca caggggactg atctcaagac ctcatcacat cctgaaatgc    600
ttcatgggat ggcccctcag caaaagcatr ggcagactcc tacaactctt ccaagagcag    660
ctggtcgaga aaccaaatat gcaaatctct cctcaccaac ttctacagta tctgagagtc    720
agctgactaa gcctggagta attcgcccag tacctgtaaa atccagaata ttactgaaaa    780
aagaggagga rgtctatgaa cccaacccctt tcagtaaata cttggaagat aacagcgacc    840 tctttctctga acaggatgta acagtccctc ccaagcctgt ctcgctccat cctttatatc    900 agactaaaact ctatcctcct gctaagtcac tgctgcatcc acagaccctc tcacatgctg    960
actgtcttgc cccaggaccc ttcagtcatc tgtccttctc cttgagtgat gaacaggaga   1020
attctcacac cctcctcagt cacaacgcat gcaacaagct gagtcatcca atggtggcta   1080
ttcctgaaca tgaagctctt gattccaaag agcaatgaag ttggagcaga ggc         1133
```

<210> SEQ ID NO 84
<211> LENGTH: 1133
<212> TYPE: DNA
<213> ORGANISM: Homo sapiens

<400> SEQUENCE: 84

```
tctctttctc attctctttc aatatggaac ttgaaaagcg tgaaaaaaga agcttattaa     60
acaagaattt agaggagaaa ctgacggtct ctgctggtgg ytctgaagcc aaacctctga    120
tcttcacatt tgtccccact gtcagaagac taccaaccca tactcagttg gctgacacct    180
ctaaattcct tgttaaaatt ccagaagaat caagtgataa gagtccagaa actgtaaata    240
ggtctaaatc caatgactac ttgaccttga atgctgggag ccaacaagag agagaccaag    300
cgaaattgac ttgtccttca gaggtcagtg aacgattttt acaagaaagg gaattcgaag    360
caaacaaact tcaagggatg cagcaaagtg acctcttcaa agctgaatat gtccttattg    420
tggactccga aggggaagat gaggctgcaa gcagaaaagt tgaacaaggc cccccagggg    480
ggattggcac cgcagctrtc cggcccaagt ctctagctat ctcgtccagt ctggtctctg    540
atgtagtgcg tcccaaaaca caggggactg atctcaagac ctcatcacat cctgaaatgc    600
ttcatgggat ggcccctcag caaaagcatg gcagactcc tacaactctt ccaagagcag     660
ctggtcgaga aaccaaatat gcaaatctct cctcaccaac ttctacagta tctgagagtc    720
agctgactaa gcctggagta attcgcccag tacctgtaaa atccagaata ttactgaaaa    780
aagaggagga agtctatgaa cccaacccctt tcagtaaata cttggaagat aacagcgacc    840 tctttctctga acaggatgta acagtccctc ccaagcctgt ctcgctccat cctttatatc    900 agactaaaact ctatcctcct gctaagtcac tgctgcatcc acagaccctc tcacatgctg    960
actgtcttgc cccaggaccc ttcagtcatc tgtccttctc cttgagtgat gaacaggaga   1020
attctcacac cctcctcagt cacaacgcat gcaacaagct gagtcatcca atggtggcta   1080
```

-continued

```
ttcctgaaca tgaagctctt gattccaaag agcaatgaag ttggagcaga ggc    1133
```

<210> SEQ ID NO 85
<211> LENGTH: 1133
<212> TYPE: DNA
<213> ORGANISM: Homo sapiens

<400> SEQUENCE: 85

```
tctctttctc attctctttc aatatggaac ttgaaaagcr tgaaaaaaga agcttattaa     60
acaagaattt agaggagaaa ctgacggtct ctgctggtgg ttctgaagcc aaacctctga    120
tcttcacatt tgtccccact gtcagaagac taccaaccca tactcagttg gctgacacct    180
ctaaattcct tgttaaaatt ccagaagaat caagtgataa gagtccagaa actgtaaata    240
ggtctaaatc caatgactac ttgaccttga atgctgggag ccaacaagag agagaccaag    300
cgaaattgac ttgtccttca gaggtcagtg gaacgatttt acaagaaagg gaattcgaag    360
caaacaaact tcaagggatg cagcaaagtg acctcttcaa agctgaatat gtccttattg    420
tggactccga aggggaagat gaggctgcaa gcagaaaagt tgaacaaggc cccccagggg    480
ggattggcac cgcagctrtc cggcccaagt ctctagctat ctcgtccagt ctggtctctg    540
atgtagtgcg tcccaaaaca caggggactg atctcaagac ctcatcacat cctgaaatgc    600
ttcatgggat ggcccctcag caaaagcatg gcagactcc tacaactctt ccaagagcag    660
ctggtcgaga aaccaaatat gcaaatctct cctcaccaac ttctacagta tctgagagtc    720
agctgactaa gcctggagta attcgcccag tacctgtaaa atccagaata ttactgaaaa    780
argaggagga agtctatgaa cccaacccctt tcagtaaata cttggaagat aacagcgacc    840
tcttttctga acaggatgta acagtccctc ccaagcctgt ctcgctccat cctttatatc    900
agactaaaact ctatcctcct gctaagtcac tgctgcatcc acagaccctc tcacatgctg    960
actgtcttgc cccaggaccc ttcagtcatc tgtccttctc cttgagtgat gaacaggaga   1020
attctcacac cctcctcagt cacaacgcat gcaacaagct gagtcatcca atggtggcta   1080
ttcctgaaca tgaagctctt gattccaaag agcaatgaag ttggagcaga ggc          1133
```

<210> SEQ ID NO 86
<211> LENGTH: 1032
<212> TYPE: DNA
<213> ORGANISM: Homo sapiens
<220> FEATURE:
<221> NAME/KEY: misc_feature
<222> LOCATION: (1)..(30)
<223> OTHER INFORMATION: N = any nucleotide
<220> FEATURE:
<221> NAME/KEY: misc_feature
<222> LOCATION: (52)..(52)
<223> OTHER INFORMATION: N = any nucleotide
<220> FEATURE:
<221> NAME/KEY: misc_feature
<222> LOCATION: (919)..(920)
<223> OTHER INFORMATION: N = any nucleotide
<220> FEATURE:
<221> NAME/KEY: misc_feature
<222> LOCATION: (945)..(945)
<223> OTHER INFORMATION: N = any nucleotide
<220> FEATURE:
<221> NAME/KEY: misc_feature
<222> LOCATION: (966)..(966)
<223> OTHER INFORMATION: N = any nucleotide
<220> FEATURE:
<221> NAME/KEY: misc_feature
<222> LOCATION: (980)..(980)
<223> OTHER INFORMATION: N = any nucleotide
<220> FEATURE:
<221> NAME/KEY: misc_feature
<222> LOCATION: (985)..(985)

<223> OTHER INFORMATION: N = any nucleotide
<220> FEATURE:
<221> NAME/KEY: misc_feature
<222> LOCATION: (995)..(995)
<223> OTHER INFORMATION: N = any nucleotide
<220> FEATURE:
<221> NAME/KEY: misc_feature
<222> LOCATION: (1013)..(1013)
<223> OTHER INFORMATION: N = any nucleotide

<400> SEQUENCE: 86

```
nnnnnnnnnn nnnnnnnnnn nnnnnnnnnn ggccctctag atgcatgctc gnagcggccg      60
ccagtgtgat ggatatctgc agaattcgcc ctttctcttt tcattctct ttcaatatgg      120
aacttgaaaa gcatgaaaaa agaagcttat aaacaagaa tttagaggag aaactgacgg      180
tctctgctgg tggttctgaa gccaaacctc tgatcttcac atttgtcccc actgtcagaa      240
gactaccaac ccatactcag ttggctgaca cctctaaatt ccttgttaaa attccagaag      300
aatcaagtga taagagtcca gaaactgtaa ataggtctaa atccaatgac tacttgacct      360
tgaatgctgg gagccaacaa gagagagacc aagcgaaatt gacttgtcct tcagaggtca      420
gtggaacgat tttacaagaa agggaattcg aagcaaacaa acttcaaggg atgcagcaaa      480
gtgacctctt caaagctgaa tatgtcctta ttgtggactc cgaaggggaa gatgaggctg      540
caagcagaaa agttgaacaa ggccccccag ggggattgg caccgcagct gtccggccca      600
agtctctagc tatctcgtcc agtctggtct ctgatgtagt gcgtcccaaa acacagggga      660
ctgatctcaa gacctcatca catcctgaaa tgcttcatgg gatggcccct cagcaaaagc      720
atgggcagac tcctacaact cttccaagag cagctggtcg agaaaccaaa tatgcaaatc      780
tctcctcacc aacttctaca gtatctgaga gtcagctgac taagcctgga gtaattcgcc      840
cagtacctgt aaaatccaga atattactga aaaggagga ggaagtctat gaacccaacc      900
ctttcagtaa atacttggnn gataacagcg acctctttc tgaanaggat gtaacagtcc      960
ctcccnagcc tgtctcgctn catcntttat atcanactaa actctatcct ccngctaagt     1020
cactgctgca tc                                                         1032
```

<210> SEQ ID NO 87
<211> LENGTH: 1133
<212> TYPE: DNA
<213> ORGANISM: Homo sapiens

<400> SEQUENCE: 87

```
tctctttctc attctctttc aatatggaac ttgaaaagcg tgaaaaaga agcttattaa      60
acaagaattt agaggagaaa ctgacggtct ctgctggtgg ttctgaagcc aaacctctga      120
tcttcacatt tgtccccact gtcagaagac taccaaccca tactcagttg ctgacacct      180
ctaaattcct tgttaaaatt ccagaagaat caagtgataa gagtccagaa actgtaaata      240
ggtctaaatc caatgactac ttgaccttga atgctgggag ccaacaagag agagaccaag      300
cgaaattgac ttgtccttca gaggtcagtg aacgatttt acaagaaagg gaattcgaag      360
caaacaaact tcaagggatg cagcaaagtg acctcttcaa agctgaatat gtccttattg      420
tggactccga aggggaagat gaggctgcaa gcagaaaagt tgaacaaggc ccccagggg      480
ggattggcac cgcagctatc cggcccaagt ctctagctat ctcgtccagt ctggtctctg      540
atgtagtgcg tcccaaaaca caggggactg atctcaagac ctcatcacat cctgaaatgc      600
ttcatgggat ggcccctcag caaaagcatg gcagactcc tacaactctt ccaagagcag      660
ctggtcgaga aaccaaatat gcaaatctct cctcaccaac ttctacagta tctgagagtc      720
```

```
agctgactaa gcctggagta attcgcccag tacctgtaaa atccagaata ttactgaaaa      780
aagaggagga agtctatgaa cccaacccct tcagtaaata cttggaagat aacagcgacc      840
tctttcctga acaggatgta acagtccctc ccaagcctgt ctcgctccat cctttatatc      900
agactaaact ctatcctcct gctaagtcac tgctgcatcc acagaccctc tcacatgctg      960
actgtcttgc cccaggaccc ttcagtcatc tgtccttctc cttgagtgat gaacaggaga     1020
attctcacac cctcctcagt cacaacgcat gcaacaagct gagtcatcca atggtggcta     1080
ttcctgaaca tgaagctctt gattccaaag agcaatgaag ttggagcaga ggc            1133
```

<210> SEQ ID NO 88
<211> LENGTH: 1733
<212> TYPE: DNA
<213> ORGANISM: Homo sapiens

<400> SEQUENCE: 88

```
tctctttctc attctctttc aatatggaac ttgaaaagcg tgaaaaaaga agcttattaa       60
acaagaattt agaggagaaa ctgacggtct ctgctggtgg ttctgaagcc aaacctctga      120
tcttcacatt tgtccccact gtcagaagac taccaaccca tactcagttg gctgacacct      180
ctaaattcct tgttaaaatt ccagaagaat caagtgataa gagtccagaa actgtaaata      240
ggtctaaatc caatgactac ttgaccttga atgctgggag ccaacaagag agagaccaag      300
cgaaattgac ttgtccttca gaggtcagtg gaacgatttt acaagaaagg gaattcgaag      360
caaacaaact tcaagggatg cagcaaagtg acctcttcaa agctgaatat gtccttattg      420
tggactccga aggggaagat gaggctgcaa gcagaaaagt tgaacaaggc cccccagggg      480
ggattggcac cgcagctatc cggcccaagt ctctagctat ctcgtccagt ctggtctctg      540
atgtagtgcg tcccaaaaca caggggactg atctcaagac ctcatcacat cctgaaatgc      600
tctctttctc attctctttc aatatggaac ttgaaaagcg tgaaaaaaga agcttattaa      660
acaagaattt agaggagaaa ctgacggtct ctgctggtgg ttctgaagcc aaacctctga      720
tcttcacatt tgtccccact gtcagaagac taccaaccca tactcagttg gctgacacct      780
ctaaattcct tgttaaaatt ccagaagaat caagtgataa gagtccagaa actgtaaata      840
ggtctaaatc caatgactac ttgaccttga atgctgggag ccaacaagag agagaccaag      900
cgaaattgac ttgtccttca gaggtcagtg gaacgatttt acaagaaagg gaattcgaag      960
caaacaaact tcaagggatg cagcaaagtg acctcttcaa agctgaatat gtccttattg     1020
tggactccga aggggaagat gaggctgcaa gcagaaaagt tgaacaaggc cccccagggg     1080
ggattggcac cgcagctrtc cggcccaagt ctctagctat ctcgtccagt ctggtctctg     1140
atgtagtgcg tcccaaaaca caggggactg atctcaagac ctcatcacat cctgaaatgc     1200
ttcatgggat ggcccctcag caaaagcatg gcagactcc tacaactctt ccaagagcag     1260
ctggtcgaga aaccaaatat gcaaatctct cctcaccaac ttctacagta tctgagagtc     1320
agctgactaa gcctggagta attcgcccag tacctgtaaa atccagaata ttactgaaaa     1380
aagaggagga agtctatgaa cccaacccct tcagtaaata cttggaagat aacagcgacc     1440
tctttcctga acaggatgta acagtccctc ccaagcctgt ctcgctccat cctttatatc     1500
agactaaact ctatcctcct gctaagtcac tgctgcatcc acagaccctc tcacatgctg     1560
actgtcttgc cccaggaccc ttcagtcatc tgtccttctc cttgagtgat gaacaggaga     1620
attctcacac cctcctcagt cacaacgcat gcaacaagct gagtcatcca atggtggcta     1680
ttcctgaaca tgaagctctt gattccaaag agcaatgaag ttggagcaga ggc            1733
```

```
<210> SEQ ID NO 89
<211> LENGTH: 587
<212> TYPE: DNA
<213> ORGANISM: Homo sapiens
<220> FEATURE:
<221> NAME/KEY: misc_feature
<222> LOCATION: (1)..(18)
<223> OTHER INFORMATION: n = any nucleotide
<220> FEATURE:
<221> NAME/KEY: misc_feature
<222> LOCATION: (20)..(25)
<223> OTHER INFORMATION: n = any nucleotide
<220> FEATURE:
<221> NAME/KEY: misc_feature
<222> LOCATION: (32)..(35)
<223> OTHER INFORMATION: n = any nucleotide
<220> FEATURE:
<221> NAME/KEY: misc_feature
<222> LOCATION: (42)..(44)
<223> OTHER INFORMATION: n = any nucleotide
<220> FEATURE:
<221> NAME/KEY: misc_feature
<222> LOCATION: (46)..(46)
<223> OTHER INFORMATION: n = any nucleotide
<220> FEATURE:
<221> NAME/KEY: misc_feature
<222> LOCATION: (48)..(49)
<223> OTHER INFORMATION: n = any nucleotide

<400> SEQUENCE: 89
nnnnnnnnnn nnnnnnnngn nnnnnggccc tnnnngatgc annntngnng cggccgccag      60
tgtgatggat atctgcagaa ttcgcccttg cctctgctcc aacttcattg ctctttggaa     120
tcaagagctt catgttcagg aatagccacc attggatgac tcagcttgtt gcatgcgttg     180
tgactgagga gggtgtgaga attctcctgt tcatcactca aggagaagga cagatgactg     240
aagggtcctg gggcaagaca gtcagcatgt gagagggtct gtggatgcag cagtgactta     300
gcaggaggat agagtttagt ctgatataaa ggatggagcg agacaggctt gggagggact     360
gttacatcct gttcagaaaa gaggtcgctg ttatcttcca agtatttact gaaagggttg     420
ggttcataga cttcctcctc tttttttcagt aatattctgg attttacagg tactgggcga     480
attactccag gcttagtcag ctgactctca gatactgtag aagttggtga ggagagattt     540
gcatatttgg tttctcgacc agctgctctt ggaagagttg taggagt                   587

<210> SEQ ID NO 90
<211> LENGTH: 512
<212> TYPE: DNA
<213> ORGANISM: Homo sapiens
<220> FEATURE:
<221> NAME/KEY: misc_feature
<222> LOCATION: (509)..(510)
<223> OTHER INFORMATION: n = any nucleotide
<220> FEATURE:
<221> NAME/KEY: misc_feature
<222> LOCATION: (512)..(512)
<223> OTHER INFORMATION: n = any nucleotide

<400> SEQUENCE: 90
gactaagcct ggagtaattc gcccagtacc tgtaaaatcc agaatattac tgaaaaaga      60 ggaggaagtc tatgaaccca acctttcag taaatacttg gaagataaca gcgacctctt     120
ttctgaacag gatgtaacag tccctcccaa gcctgtctcg ctccatcctt tatatcagac     180
taaactctat cctcctgcta agtcactgct gcatccacag accctctcac atgctgactg     240
tcttgcccca ggacccttca gtcatctgtc cttctccttg agtgatgaac aggagaattc     300
tcacaccctc tcagtcaca acgcatgcaa caagctgagt catccaatgg tggctattcc     360
```

| | |
|---|---|
| tgaacatgaa gctcttgatt ccaaagagca atgaagttgg agcagaggca agggcgaatt | 420 |
| ctgcagatat ccatcacact ggcggccgct cgagcatgca tctagagggc ccaattcgcc | 480 |
| ctatagtgag tcgtattaca attcactgnn gn | 512 |

<210> SEQ ID NO 91
<211> LENGTH: 671
<212> TYPE: DNA
<213> ORGANISM: Homo sapiens
<220> FEATURE:
<221> NAME/KEY: misc_feature
<222> LOCATION: (1)..(42)
<223> OTHER INFORMATION: n = any nucleotide
<220> FEATURE:
<221> NAME/KEY: misc_feature
<222> LOCATION: (51)..(51)
<223> OTHER INFORMATION: n = any nucleotide
<220> FEATURE:
<221> NAME/KEY: misc_feature
<222> LOCATION: (662)..(671)
<223> OTHER INFORMATION: n = any nucleotide

<400> SEQUENCE: 91

| | |
|---|---|
| nnnnnnnnnn nnnnnnnnnn nnnnnnnnnn nnnnnnnnnn nngggccgcc ngtgtgctgg | 60 |
| aattcgccct ttctctttct cattctcttt caatatggaa cttgaaaagc gtgaaaaaag | 120 |
| aagcttatta acaagaatt tagaggagaa actgacgact aagcctggag taattcgccc | 180 |
| agtacctgta aaatccagaa tattactgaa aaagaggag gaagtctatg aacccaaccc | 240 |
| cttcagtaaa tacttggaag ataacagcga cctcttttct gaacaggatg taacagtccc | 300 |
| tcccaagcct gtctcgctcc atcctttata tcagactaaa ctctatcctc ctgctaagtc | 360 |
| actgctgcat ccacagaccc ctctcacatg tgactgtctt gccccaggac ccttcagtca | 420 |
| tctgtccttc tccttgagtg atgaacagga gaattctcac accctcctca gtcacaacgc | 480 |
| atgcaacaag ctgagtcatc caatggtggc tattcctgaa catgaagctc ttgattccaa | 540 |
| agagcaatga agttggagca gaggcaaggg cgaattctgc agatatccat cacactggcg | 600 |
| gccgctcgag catgcatcta gagggcccaa ttcgccctat agtgagtcgt attacaattc | 660 |
| annnnnnnnn n | 671 |

<210> SEQ ID NO 92
<211> LENGTH: 1593
<212> TYPE: DNA
<213> ORGANISM: Homo sapiens

<400> SEQUENCE: 92

| | |
|---|---|
| tctctttctc attctctttc aatatggaac ttgaaaagcg tgaaaaaga agcttattaa | 60 |
| acaagaattt agaggagaaa ctgacggtct ctgctggtgg ttctgaagcc aaacctctga | 120 |
| tcttcacatt tgtccccact gtcagaagac taccaaccca tactcagttg gctgacacct | 180 |
| ctaaattcct tgttaaaatt ccagaagaat caagtgataa gagtccagaa actgtaaata | 240 |
| ggtctaaatc caatgactac ttgaccttga atgctgggag ccaacaagag agagaccaag | 300 |
| cgaaattgac ttgtccttca gaggtcagtg gaacgatttt acaagaaagg gaattcgaag | 360 |
| caaacaaact tcaagggatg cagcaaagtg acctcttcaa agctgaatat gtccttattg | 420 |
| tggactccga aggggaagat gaggctgcaa gcagaaaagt tgaacaaggc cccccagggg | 480 |
| ggattggcac cgcagctatc cggcccaagt ctctagctat ctcgtccagt ctggtctctg | 540 |
| atgtagtgcg tccaaaaaca caggggactg atctcaagac ctcatcacat cctgaaatgc | 600 |
| ttcatgggat ggcccctcag caaaagcatg ggcagcaata caagaccaag tcaagctaca | 660 |

-continued

```
aggcttttgc agcaatccct acaaacacat tgcttttgga acagaaggca ctagatgaac    720
cagccaagac tgaaagtgtc tccaaggaca acacattaga accaccagtg gagctctatt    780
ttcctgcaca gctcaggcag caaactgaag agctctgtgc taccattgat aaggtcttac    840
aggattcctt gtctatgcat tcttctgatt ctccttcaag gtccccaaag acattgttgg    900
gttctgacac agtcaaaact cctacaactc ttccaagagc agctggtcga gaaaccaaat    960
atgcaaatct ctcctcacca acttctacag tatctgagag tcagctgact aagcctggag   1020
taattcgccc agtacctgta aaatccagaa tattactgaa aaagaggag gaagtctatg    1080
aacccaaccc tttcagtaaa tacttggaag ataacagcga cctcttttct gaacaggatg   1140
taacagtccc tcccaagcct gtctcgctcc atcctttata tcagactaaa ctctatcctc   1200
ctgctaagtc actgctgcat ccacagaccc tctcacatgc tgactgtctt gcccaggac   1260
ccttcagtca tctgtccttc tccttgagtg atgaacagga gaattctcac accctcctca   1320
gtcacaacgc atgcaacaag ctgagtcatc caatggtggc tattcctgaa catgaagctc   1380
ttgattccaa agagcaatga agttggagca gaggctgaaa acacaggctg ctgaagtttt   1440
tttggaatgc tggtgctaac cacttgctag atttaacttt tttttttttt ttccagaatg   1500
agtgctccct ttatgagctg cagtgcagca gaaccaaaaa aaaagtttgc tgcaattata   1560
tagcatcaca gtgctctgct aacagccagc ata                                1593
```

```
<210> SEQ ID NO 93
<211> LENGTH: 22
<212> TYPE: DNA
<213> ORGANISM: Artificial
<220> FEATURE:
<223> OTHER INFORMATION: primer

<400> SEQUENCE: 93
tctctttctc attctctttc aa                                              22

<210> SEQ ID NO 94
<211> LENGTH: 19
<212> TYPE: DNA
<213> ORGANISM: Artificial
<220> FEATURE:
<223> OTHER INFORMATION: primer

<400> SEQUENCE: 94
atgaagttgg agcagaggc                                                  19

<210> SEQ ID NO 95
<211> LENGTH: 590
<212> TYPE: DNA
<213> ORGANISM: Homo sapiens
<220> FEATURE:
<221> NAME/KEY: misc_feature
<222> LOCATION: (2)..(29)
<223> OTHER INFORMATION: n = any nucleotide
<220> FEATURE:
<221> NAME/KEY: misc_feature
<222> LOCATION: (51)..(52)
<223> OTHER INFORMATION: n = any nucleotide

<400> SEQUENCE: 95
gnnnnnnnnn nnnnnnnnnn nnnnnnnnng gccctctaga tgcatgctcg nngcggccgc     60
cagtgtgatg gatatctgca gaattcgccc ttgcctctgc tccaacttca ttgctctttg   120
gaatcaagag cttcatgttc aggaatagcc accattggat gactcagctt gttgcatgcg   180
ttgtgactga ggagggtgtg agaattctcc tgttcatcac tcaaggagaa ggacagatga   240
```

```
ctgaagggtc ctggggcaag acagtcagca tgtgagaggg tctgtggatg cagcagtgac        300
ttagcaggag gatagagttt agtctgatat aaaggatgga gcgagacagg cttgggaggg        360
actgttacat cctgttcaga aaagaggtcg ctgttatctt ccaagtattt actgaaaggg        420
ttgggttcat agacttcctc ctcttttttc agtaatattc tggattttac aggtactggg        480
cgaattactc caggcttagt cagctgactc tcagatactg tagaagttgg tgaggagaga        540
tttgcatatt tggtttctcg accagctgct cttggaagag ttgtaggagt                   590

<210> SEQ ID NO 96
<211> LENGTH: 1023
<212> TYPE: DNA
<213> ORGANISM: Homo sapiens
<220> FEATURE:
<221> NAME/KEY: misc_feature
<222> LOCATION: (1)..(29)
<223> OTHER INFORMATION: n = any nucleotide
<220> FEATURE:
<221> NAME/KEY: misc_feature
<222> LOCATION: (44)..(46)
<223> OTHER INFORMATION: n = any nucleotide
<220> FEATURE:
<221> NAME/KEY: misc_feature
<222> LOCATION: (49)..(51)
<223> OTHER INFORMATION: n = any nucleotide
<220> FEATURE:
<221> NAME/KEY: misc_feature
<222> LOCATION: (879)..(879)
<223> OTHER INFORMATION: n = any nucleotide
<220> FEATURE:
<221> NAME/KEY: misc_feature
<222> LOCATION: (917)..(918)
<223> OTHER INFORMATION: n = any nucleotide
<220> FEATURE:
<221> NAME/KEY: misc_feature
<222> LOCATION: (921)..(921)
<223> OTHER INFORMATION: n = any nucleotide
<220> FEATURE:
<221> NAME/KEY: misc_feature
<222> LOCATION: (931)..(931)
<223> OTHER INFORMATION: n = any nucleotide
<220> FEATURE:
<221> NAME/KEY: misc_feature
<222> LOCATION: (964)..(964)
<223> OTHER INFORMATION: n = any nucleotide
<220> FEATURE:
<221> NAME/KEY: misc_feature
<222> LOCATION: (978)..(978)
<223> OTHER INFORMATION: n = any nucleotide
<220> FEATURE:
<221> NAME/KEY: misc_feature
<222> LOCATION: (993)..(993)
<223> OTHER INFORMATION: n = any nucleotide

<400> SEQUENCE: 96
nnnnnnnnnn nnnnnnnnnn nnnnnnnnng ccctctagat gcannntcnn ngcggccgcc        60
agtgtgatgg atatctgcag aattcgccct ttctctttct cattctcttt caatatggaa       120
cttgaaaagc atgaaaaaag aagcttatta acaagaatt tagaggagaa actgacggtc        180
tctgctggtg gttctgaagc caaacctctg atcttcacat ttgtccccac tgtcagaaga       240
ctaccaaccc atactcagtt ggctgacacc tctaaattcc ttgttaaaat tccagaagaa       300
tcaagtgata agagtccaga aactgtaaat aggtctaaat ccaatgacta cttgaccttg       360
aatgctggga gccaacaaga gagagaccaa gcgaaattga cttgtccttc agaggtcagt       420
ggaacgattt tacaagaaag ggaattcgaa gcaaacaaac ttcaagggat gcagcaaagt       480
gacctcttca aagctgaata tgtccttatt gtggactccg aaggggaaga tgaggctgca       540
agcagaaaag ttgaacaagg ccccccaggg gggattggca ccgcagctgt ccggcccaag       600
```

-continued

```
tctctagcta tctcgtccag tctggtctct gatgtagtgc gtcccaaaac acaggggact    660
gatctcaaga cctcatcaca tcctgaaatg cttcatggga tggcccctca gcaaaagcat    720
gggcagactc ctacaactct tccaagagca gctggtcgag aaaccaaata tgcaaatctc    780
tcctcaccaa cttctacagt atctgagagt cagctgacta agcctggagt aattcgccca    840
gtacctgtaa aatccagaat attactgaaa aagaggang aagtctatga acccaacccct   900 ttcagtaaat acttggnnga naacagcgac ntcttttctg aacaggatgt aacagtccct    960
cccnagcctg tctcgctnca tcctttatat canactaaac tctatcctcc tgctaagtca    1020
ctg                                                                 1023
```

<210> SEQ ID NO 97
<211> LENGTH: 1133
<212> TYPE: DNA
<213> ORGANISM: Homo sapiens

<400> SEQUENCE: 97

```
tctctttctc attctctttc aatatggaac ttgaaaagcg tgaaaaaaga agcttattaa     60
acaagaattt agaggagaaa ctgacggtct ctgctggtgg ttctgaagcc aaacctctga    120
tcttcacatt tgtccccact gtcagaagac taccaaccca tactcagttg gctgacacct    180
ctaaattcct tgttaaaatt ccagaagaat caagtgataa gagtccagaa actgtaaata    240
ggtctaaatc caatgactac ttgaccttga atgctgggag ccaacaagag agagaccaag    300
cgaaattgac ttgtccttca gaggtcagtg gaacgatttt acaagaaagg gaattcgaag    360
caaacaaact tcaagggatg cagcaaagtg acctcttcaa agctgaatat gtccttattg    420
tggactccga aggggaagat gaggctgcaa gcagaaaagt tgaacaaggc cccccagggg    480
ggattggcac cgcagctatc cggcccaagt ctctagctat ctcgtccagt ctggtctctg    540
atgtagtgcg tcccaaaaca caggggactg atctcaagac ctcatcacat cctgaaatgc    600
ttcatgggat ggcccctcag caaaagcatg ggcagactcc tacaactctt ccaagagcag    660
ctggtcgaga aaccaaatat gcaaatctct cctcaccaac ttctacagta tctgagagtc    720
agctgactaa gcctggagta attcgcccag tacctgtaaa atccagaata ttactgaaaa    780 agaggagga agtctatgaa cccaaccctt tcagtaaata cttggaagat aacagcgacc    840
tcttttctga acaggatgta acagtccctc ccaagcctgt ctcgctccat cctttatatc    900
agactaaact ctatcctcct gctaagtcac tgctgcatcc acagaccctc tcacatgctg    960
actgtcttgc cccaggaccc ttcagtcatc tgtccttctc cttgagtgat gaacaggaga    1020
attctcacac cctcctcagt cacaacgcat gcaacaagct gagtcatcca atggtggcta    1080
ttcctgaaca tgaagctctt gattccaaag agcaatgaag ttggagcaga ggc          1133
```

<210> SEQ ID NO 98
<211> LENGTH: 931
<212> TYPE: DNA
<213> ORGANISM: Homo sapiens
<220> FEATURE:
<221> NAME/KEY: misc_feature
<222> LOCATION: (1)..(1)
<223> OTHER INFORMATION: n = any nucleotide
<220> FEATURE:
<221> NAME/KEY: misc_feature
<222> LOCATION: (5)..(32)
<223> OTHER INFORMATION: n = any nucleotide
<220> FEATURE:
<221> NAME/KEY: misc_feature
<222> LOCATION: (35)..(36)
<223> OTHER INFORMATION: n = any nucleotide
<220> FEATURE:

```
<221> NAME/KEY: misc_feature
<222> LOCATION: (785)..(785)
<223> OTHER INFORMATION: n = any nucleotide
<220> FEATURE:
<221> NAME/KEY: misc_feature
<222> LOCATION: (865)..(865)
<223> OTHER INFORMATION: n = any nucleotide
<220> FEATURE:
<221> NAME/KEY: misc_feature
<222> LOCATION: (897)..(897)
<223> OTHER INFORMATION: n = any nucleotide
<220> FEATURE:
<221> NAME/KEY: misc_feature
<222> LOCATION: (899)..(899)
<223> OTHER INFORMATION: n = any nucleotide
<220> FEATURE:
<221> NAME/KEY: misc_feature
<222> LOCATION: (912)..(912)
<223> OTHER INFORMATION: n = any nucleotide

<400> SEQUENCE: 98
ngggnnnnnn nnnnnnnnnn nnnnnnnnnn nnctnngtaa cggccgccag tgtgctggaa      60
ttcgcccttg cctctgctcc aacttcattg ctctttggaa tcaagagctt catgttcagg     120
aatagccacc attggatgac tcagcttgtt gcatgcgttg tgactgagga gggtgtgaga     180
attctcttgt tcatcactca aggagaagga cagatgactg aagggtcctg gggcaagaca     240
gtcagcatgt gagagggtct gtggatgcag cagtgactta gcaggaggat agagtttagt     300
ctgatataaa ggatggagcg agacaggctt gggagggact gttacatcct gttcagaaaa     360
gaggtcgctg ttatcttcca agtatttact gaaagggttg ggttcataga cttcctcctc     420
ttttttcagt aatattctgg attttacagg tactgggcga attactccag gcttagtcag     480
ctgactctca gatactgtag aagttggtga ggagagattt gcatatttgg tttctcgacc     540
agctgctctt ggaagagttg taggagtttt gactgtgtca gaacccaaca atgtctttgg     600
ggaccttgaa ggagaatcag aagaatgctc cactggtggt tctaatgtgt tgtccttgga     660
gacactttca gtcttggctg gttcatctag tgccttctgt tccaaaagca atgtgtttgt     720
agggattgct gcaaaagcct tgtagcttga cttggtcttg tattgctgcc catgcttttg     780
ctganggcc atcccatgaa gcatttcagg atgtgatgag gtcttgagat cagtcccctg     840
tgttttggga cgcactacat caganaccag actggacgag atagctagag acttggncng     900
gacagctgcg gngccaatcc cccctggggg g                                    931

<210> SEQ ID NO 99
<211> LENGTH: 904
<212> TYPE: DNA
<213> ORGANISM: Homo sapiens
<220> FEATURE:
<221> NAME/KEY: misc_feature
<222> LOCATION: (1)..(37)
<223> OTHER INFORMATION: n = any nucleotide
<220> FEATURE:
<221> NAME/KEY: misc_feature
<222> LOCATION: (39)..(41)
<223> OTHER INFORMATION: n = any nucleotide
<220> FEATURE:
<221> NAME/KEY: misc_feature
<222> LOCATION: (891)..(891)
<223> OTHER INFORMATION: n = any nucleotide

<400> SEQUENCE: 99
nnnnnnnnnn nnnnnnnnnn nnnnnnnnnn nnnnnnncnn ngtaacggcc gccagtgtgc      60
tggaattcgc ccttgcctct gctccaactt cattgctctt tggaatcaag agctcatgtt     120
caggaatagc caccattgga tgactcagct tgttgcatgc gttgtgactg aggagggtgt     180
```

-continued

```
gagaattctc ctgttcatca ctcaaggaga aggacagatg actgaagggt cctggggcaa    240
gacagtcagc atgtgagagg gtctgtggat gcagcagtga cttagcagga ggatagagtt    300
tagtctgata taaaggatgg agcgagacag gcttgggagg gactgttaca tcctgttcag    360
aaaagaggtc gctgttatct tccaagtatt tactgaaagg gttgggttca tagacttcct    420
cctccttttt cagtaatatt ctggatttta caggtactgg gcgaattact ccaggcttag    480
tcagctgact ctcagatact gtagaagttg gtgaggagaa atttgcatat ttggtttctc    540
gaccagctgc tcttggaaga gttgtaggag tctgcccatg cttttgctga ggggccatcc    600
catgaagcat ttcaggatgt gatgaggtct tgagatcagt cccctgtgtt ttgggacgca    660
ctacatcaga gaccagactg gacgagatag ctagagactt gggccggaca gctgcggtgc    720 caatccccccc tggggggcct tgttcaactt ttctgcttgc agcctcatct tcccctttcgg    780 agtccacaat aaggacatat tcagctttga agaggtcact ttgctgcatc ccttgaagtt    840
tgtttgcttc gaattccctt tcttgtaaaa tcgttccact gacctctgaa ngacaagtca    900
attt                                                                 904
```

<210> SEQ ID NO 100
<211> LENGTH: 564
<212> TYPE: DNA
<213> ORGANISM: Homo sapiens
<220> FEATURE:
<221> NAME/KEY: misc_feature
<222> LOCATION: (1)..(8)
<223> OTHER INFORMATION: n = any nucleotide
<220> FEATURE:
<221> NAME/KEY: misc_feature
<222> LOCATION: (10)..(10)
<223> OTHER INFORMATION: n = any nucleotide
<220> FEATURE:
<221> NAME/KEY: misc_feature
<222> LOCATION: (12)..(13)
<223> OTHER INFORMATION: n = any nucleotide
<220> FEATURE:
<221> NAME/KEY: misc_feature
<222> LOCATION: (15)..(25)
<223> OTHER INFORMATION: n = any nucleotide
<220> FEATURE:
<221> NAME/KEY: misc_feature
<222> LOCATION: (27)..(28)
<223> OTHER INFORMATION: n = any nucleotide
<220> FEATURE:
<221> NAME/KEY: misc_feature
<222> LOCATION: (30)..(30)
<223> OTHER INFORMATION: n = any nucleotide

<400> SEQUENCE: 100

```
nnnnnnnngn gnngnnnnnn nnnnnanncn ctagtaacgg ccgccagtgt gctggaattc     60
gcccttgcct ctgctccaac ttcattgctc tttggaatca agagcttcat gttcaggaat    120
agccaccatt ggatgactca gcttgttgca tgcgttgtga ctgaggaggg tgtgagaatt    180
ctcctgttca tcactcaagg agaaggacag atgactgaag gtcctgggg caagacagtc    240 agcatgtgag agggtctgtg gatgcagcag tgacttagca ggaggataga gtttagtctg    300
atataaagga tggagcgaga caggcttggg agggactgtt acatcctgtt cagaaaagag    360
gtcgctgtta tcttccaagt atttactgaa agggttgggt tcatagactt cctcctcttt    420 ttcagtaat attctggatt ttacaggtac tgggcgaatt actccaggct tagtcagctg    480
actctcagat actgtagaag ttggtgagga gagatttgca tatttggttt ctcgaccagc    540
tgctcttgga agagttgtag gagt                                          564
```

<210> SEQ ID NO 101

```
<211> LENGTH: 1409
<212> TYPE: DNA
<213> ORGANISM: Homo sapiens

<400> SEQUENCE: 101
tctcattctc tttcaatatg gaacttgaaa agcgtgaaaa aagaagctta ttaaacaaga      60
atttagagga gaaactgacg gtctctgctg gtggttctga agccaaacct ctgatcttca     120
catttgtccc cactgtcaga agactaccaa cccatactga gttggctgac acctctaaat    180
tccttgttaa aattccagaa gaatcaagtg ataagagtcc agaaactgta aataggtcta    240
aatccaatga ctacttgacc ttgaatgctg ggagccaaca agagagagac caagcgaaat    300
tgacttgtcc ttcagaggtc agtggaacga ttttacaaga aagggaattc gaagcaaaca    360
aacttcaagg gatgcagcaa agtgacctct tcaaagctga atatgtcctt attgtggact    420
ccgaagggga agatgaggct gcaagcagaa aagttgaaca aggcccccca ggggggattg    480
gcaccgcagc tatccggccc aagtctctag ctatctcgtc cagtctggtc tctgatgtag    540
tgcgtcccaa aacacagggg actgatctca rgacctcatc acatcctgaa atgcttcatg    600
ggatggcccc tcagcaaaag catgggcagc aatacaagac caagtcaagc tacaaggctt    660
ttgcagcaat ccctacaaac acattgcttt tggaacagaa ggcactagat gaaccagcca    720
agactgaaag tgtctccaag gacaacacat tagaaccacc agtggagctc tattttcctg    780
cacagctcag gcagcaaact gaagagctct gtgctaccat tgataaggtc ttacaggatt    840
ccttgtctat gcattcttct gattctcctt caaggtcccc aaagacattg ttgggytctg    900
acacagtcaa aactcctaca actcttccaa gagcagctgg tcgagaaacc aaatatgcaa    960
atctctcctc accaacttct acagtatctg agagtcagct gactaagcct ggagtaattc   1020
gcccagtacc tgtaaaatcc agaatattac tgaaaaaaga ggaggaagtc tatgaaccca   1080
accctttcag taaatacttg gaagataaca gcgacctctt ttctgaacag gatgtaacag   1140
tccctcccaa gcctgtctcg ctccatcctt tatatcagac taaactctat cctcctgcta   1200
agtcactgct gcatccacag accctctcac atgctgactg tcttgcccca ggacccttca   1260
gtcatctgtc cttctccttg agtgatgaac aggagaattc tcacaccctc ctcagtcaca   1320
acgcatgcaa caagctgagt catccaatgg tggctattcc tgaacatgaa gctcttgatt   1380
ccaaagagca atgaagttgg agcagaggc                                      1409

<210> SEQ ID NO 102
<211> LENGTH: 569
<212> TYPE: DNA
<213> ORGANISM: Homo sapiens
<220> FEATURE:
<221> NAME/KEY: misc_feature
<222> LOCATION: (1)..(12)
<223> OTHER INFORMATION: n = any nucleotide
<220> FEATURE:
<221> NAME/KEY: misc_feature
<222> LOCATION: (14)..(34)
<223> OTHER INFORMATION: n = any nucleotide
<220> FEATURE:
<221> NAME/KEY: misc_feature
<222> LOCATION: (36)..(39)
<223> OTHER INFORMATION: n = any nucleotide

<400> SEQUENCE: 102
nnnnnnnnnn nngnnnnnnn nnnnnnnnnn nnnncnnnnt aacggccgcc agtgtgctgg     60
aattcgccct tgcctctgct ccaacttcat tgctctttgg aatcaagagc ttcatgttca    120
ggaatagcca ccattggatg actcagcttg ttgcatgcgt tgtgactgag gagggtgtga    180
```

```
gaattctcct gttcatcact caaggagaag gacagatgac tgaagggtcc tggggcaaga    240
cagtcagcat gtgagagggt ctgtggatgc agcagtgact tagcaggagg atagagttta    300
gtctgatata aaggatggag cgagacaggc ttgggaggga ctgttacatc ctgttcagaa    360
aagaggtcgc tgttatcttc caagtattta ctgaaagggt tgggttcata gacttcctcc    420 tctttttca gtaatattct ggattttaca ggtactgggc gaattactcc aggcttagtc     480
agctgactct cagatactgt agaagttggt gaggagagat ttgcatattt ggtttctcga    540
ccagctgctc ttggaagagt tgtaggagt                                      569
```

<210> SEQ ID NO 103
<211> LENGTH: 570
<212> TYPE: DNA
<213> ORGANISM: Homo sapiens
<220> FEATURE:
<221> NAME/KEY: misc_feature
<222> LOCATION: (1)..(31)
<223> OTHER INFORMATION: n = any nucleotide
<220> FEATURE:
<221> NAME/KEY: misc_feature
<222> LOCATION: (33)..(40)
<223> OTHER INFORMATION: n = any nucleotide

<400> SEQUENCE: 103

```
nnnnnnnnnn nnnnnnnnnn nnnnnnnnnn ngnnnnnnnn taacggccgc cagtgtgctg     60
gaattcgccc ttgcctctgc tccaacttca ttgctctttg gaatcaagag cttcatgttc    120
aggaatagcc accattggat gactcagctt gttgcatgcg ttgtgactga ggagggtgtg    180
agaattctcc tgttcatcac tcaaggagaa ggacagatga ctgaagggtc ctggggcaag    240
acagtcagca tgtgagaggg tctgtggatg cagcagtgac ttagcaggag gatagagttt    300
agtctgatat aaaggatgga gcgagacagg cttgggaggg actgttacat cctgttcaga    360
aaagaggtcg ctgttatctt ccaagtattt actgaaaggg ttgggttcat agacctcctc    420 ctctttttc agtaatattc tggattttac aggtactggg cgaattactc caggcttagt     480
cagctgactc tcagatactg tagaagttgg tgaggagaga tttgcatatt tggtttctcg    540
accagctgct cttggaagag ttgtaggagt                                     570
```

<210> SEQ ID NO 104
<211> LENGTH: 970
<212> TYPE: DNA
<213> ORGANISM: Homo sapiens
<220> FEATURE:
<221> NAME/KEY: misc_feature
<222> LOCATION: (1)..(30)
<223> OTHER INFORMATION: n = any nucleotide
<220> FEATURE:
<221> NAME/KEY: misc_feature
<222> LOCATION: (32)..(32)
<223> OTHER INFORMATION: n = any nucleotide
<220> FEATURE:
<221> NAME/KEY: misc_feature
<222> LOCATION: (45)..(45)
<223> OTHER INFORMATION: n = any nucleotide
<220> FEATURE:
<221> NAME/KEY: misc_feature
<222> LOCATION: (908)..(908)
<223> OTHER INFORMATION: n = any nucleotide
<220> FEATURE:
<221> NAME/KEY: misc_feature
<222> LOCATION: (923)..(923)
<223> OTHER INFORMATION: n = any nucleotide
<220> FEATURE:
<221> NAME/KEY: misc_feature
<222> LOCATION: (954)..(955)
<223> OTHER INFORMATION: n = any nucleotide

```
<400> SEQUENCE: 104
nnnnnnnnnn nnnnnnnnnn nnnnnnnnnn cnctagtaac ggccngccag tgtgctggaa      60
ttcgcccttg cctctgctcc aacttcattg ctctttggaa tcaagagctt catgttcagg     120
aatagccacc attggatgac tcagcttgtt gcatgcgttg tgactgagga gggtgtgaga     180
attctcctgt tcatcactca aggagaagga cagatgactg aagggtcctg gggcaagaca     240
gtcagcatgt gagagggtct gtggatgcag cagtgactta gcaggaggat agagtttagt     300
ctgatataaa ggatggagcg agacaggctt gggagggact gttacatcct gttcagaaaa     360
gaggtcgctg ttatcttcca agtatttact gaaaggggttg ggttcataga cttcctcctc     420
ttttttcagt aatattctgg attttacagg tactgggcga attactccag gcttagtcag     480
ctgactctca gatactgtag aagttggtga ggagagattt gcatatttgg tttctcgacc     540
agctgctctt ggaagagttg taggagtctg cccatgcttt tgctgagggg ccatcccatg     600
aagcatttca ggatgtgatg aggtcttgag atcagtcccc tgtgttttgg gacgcactac     660
atcagagacc agactggacg agatagctag agacttgggc cggacagctg cggtgccaat     720
cccccctggg gggccttgtt caacttttct gcttgcagcc tcatcttccc cttcggagtc     780
cacaataagg acatattcag ctttgaagag gtcactttgc tgcatccctt gaagtttgtt     840
tgcttcgaat tccctttctt gtaaaatcgt tccactgacc tctgaaggac aagtcaattt     900
cgcttggnct ctctcttgtt ggntcccagc attcaaggtc aagtagtcat tggnnttaga     960
cctatttaca                                                           970

<210> SEQ ID NO 105
<211> LENGTH: 513
<212> TYPE: DNA
<213> ORGANISM: Homo sapiens
<220> FEATURE:
<221> NAME/KEY: misc_feature
<222> LOCATION: (509)..(513)
<223> OTHER INFORMATION: n = any nucleotide

<400> SEQUENCE: 105
gactaagcct ggagtaattc gcccagtacc tgtaaaatcc agaatattac tgaaaaaga      60 ggaggaagtc tatgaaccca acccctttcag taaatacttg gaagataaca gcgacctctt    120
ttctgaacag gatgtaacag tccctcccaa gcctgtctcg ctccatcctt tatatcagac    180
taaactctat cctcctgcta agtcactgct gcatccacag accctctcac atgctgactg    240
tcttgcccca ggacccttca gtcatctgtc cttctccttg agtgatgaac aggagaattc    300
tcacaccctc ctcagtcaca acgcatgcaa caagctgagt catccaatgg tggctattcc    360
tgaacatgaa gctcttgatt ccaaagagca atgaagttgg agcagaggca agggcgaatt    420
ctgcagatat ccatcacact ggcggccgct cgagcatgca tctagagggc ccaattcgcc    480
ctatagtgag tcgtattaca attcactgnn nnn                                 513

<210> SEQ ID NO 106
<211> LENGTH: 676
<212> TYPE: DNA
<213> ORGANISM: Homo sapiens
<220> FEATURE:
<221> NAME/KEY: misc_feature
<222> LOCATION: (3)..(36)
<223> OTHER INFORMATION: n = any nucleotide
<220> FEATURE:
<221> NAME/KEY: misc_feature
<222> LOCATION: (38)..(39)
<223> OTHER INFORMATION: n = any nucleotide
<220> FEATURE:
```

```
<221> NAME/KEY: misc_feature
<222> LOCATION: (49)..(50)
<223> OTHER INFORMATION: n = any nucleotide
<220> FEATURE:
<221> NAME/KEY: misc_feature
<222> LOCATION: (664)..(671)
<223> OTHER INFORMATION: n = any nucleotide
<220> FEATURE:
<221> NAME/KEY: misc_feature
<222> LOCATION: (676)..(676)
<223> OTHER INFORMATION: n = any nucleotide

<400> SEQUENCE: 106
ggnnnnnnnn nnnnnnnnnn nnnnnnnnnn nnnnnngnna cggccgccnn gtgtgctgga      60
attcgccctt tctctttctc attctctttc aatatggaac ttgaaaagcg tgaaaaaaga     120
agcttattaa acaagaattt agaggagaaa ctgacgacta agcctggagt aattcgccca     180
gtacctgtaa aatccagaat attactgaaa aaagaggagg aagtctatga acccaaccct     240
ttcagtaaat acttggaaga taacagcgac ctcttttctg aacaggatgt aacagtccct     300
cccaagcctg tctcgctcca tcctttatat cagactaaac tctatcctcc tgctaagtca     360
ctgctgcatc cacagaccct ctcacatgct gactgtcttg ccccaggacc cttcagtcat     420
ctgtccttct ccttgagtga tgaacaggag aattctcaca ccctcctcag tcacaacgca     480
tgcaacaagc tgagtcatcc aatggtggct attcctgaac atgaagctct tgattccaaa     540
gagcaatgaa gttggagcag aggcaagggc gaattctgca gatatccatc acactggcag     600
ccgctcgagc atgcatctag agggcccaat tcgccctata gtgagtcgta ttacaattca     660
ctgnnnnnnn ntttan                                                    676
```